United States Patent
Xue et al.

(10) Patent No.: US 7,125,870 B2
(45) Date of Patent: Oct. 24, 2006

(54) ISOXAZOLINE DERIVATIVES AS INHIBITORS OF MATRIX METALLOPROTEINASES AND/OR TNF-α CONVERTING ENZYME

(75) Inventors: Chu-Biao Xue, Hockessin, DE (US); Thomas P. Maduskuie, Wilmington, DE (US); Stephen E. Mercer, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 330 days.

(21) Appl. No.: 10/697,545

(22) Filed: Oct. 30, 2003

(65) Prior Publication Data

US 2004/0122005 A1    Jun. 24, 2004

Related U.S. Application Data

(60) Provisional application No. 60/424,293, filed on Nov. 6, 2002.

(51) Int. Cl.
 *A01N 47/40* (2006.01)
(52) U.S. Cl. .............. 514/235.2; 514/253.07; 514/307; 514/339; 514/378; 544/60; 544/128; 544/363; 546/175; 548/240
(58) Field of Classification Search ........... 514/235.2, 514/253.07, 339, 378; 544/60, 128, 363; 546/175; 548/240
See application file for complete search history.

(56) References Cited

U.S. PATENT DOCUMENTS 4,769,461 A    9/1988  Musser et al.
5,716,967 A    2/1998  Kleinman
5,869,511 A    2/1999  Cohan et al.
6,114,367 A    9/2000  Cohan et al.
6,211,216 B1   4/2001  Willms et al.

OTHER PUBLICATIONS

Kleinman, E.F. et al., "Striking Effect of Hydroxamic Acid Substitution on the Phosphodiesterase Type 4 (PDE4) and TNFα Inhibitory Activity of Two Series of Rolipram Analogues: Implications for a New Active Site Model of PDE4", J. Med. Chem., vol. 41, pp. 266-270 (1998).

*Primary Examiner*—Golam M. M. Shameem
*Assistant Examiner*—Ebenezer Sackey
(74) *Attorney, Agent, or Firm*—Jing G. Sun

(57) ABSTRACT

The present application describes novel isoxazoline of formula I or II:

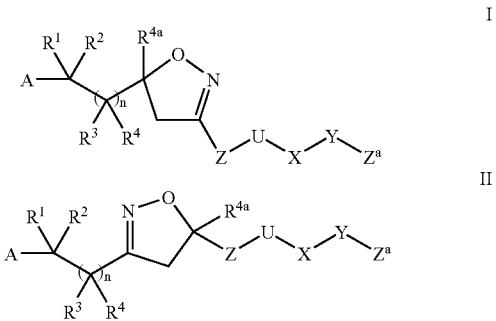

or pharmaceutically acceptable salt or prodrug forms thereof, wherein A, $R^1$, $R^2$, $R^3$, $R^4$, Z, U, X, Y, $Z^a$, and n are defined in the present specification, which are useful as inhibitors of matrix metalloproteinases (MMP), TNF-α converting enzyme (TACE), or a combination thereof.

28 Claims, No Drawings

ISOXAZOLINE DERIVATIVES AS INHIBITORS OF MATRIX METALLOPROTEINASES AND/OR TNF-α CONVERTING ENZYME

CROSS-REFERENCE TO RELATED APPLICATIONS

The present application claims the priority benefit of U.S. Provisional Application No. 60/424,293, filed Nov. 6, 2002, which is expressly incorporated fully herein by reference.

FIELD OF THE INVENTION

This invention relates generally to novel isoxazoline derivatives as inhibitors of matrix metalloproteinases (MMP), TNF-α converting enzyme (TACE), or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity though the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthitis Rheum.* 1978, 21, 761–766, Woessner et al. *Arthitis Rheum.* 1983, 26, 63–68 and Woessner et al. *Arthitis Rheum.* 1984, 27, 305–312).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthitis (Feldman et al. *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds that inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

U.S. Pat. No. 4,769,461 depicts leukotriene inhibitors of the formula:

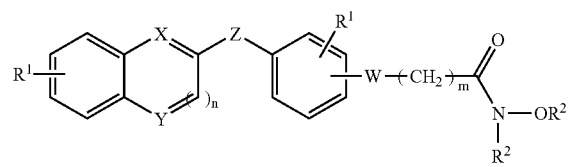

wherein X and Y can be carbon or nitrogen, Z can be a variety of linking groups, W can be CH(OH), and $R^2$ can be H. MMP and/or TACE inhibition is not mentioned. Compounds specifically described in U.S. Pat. No. 4,769,461 are not considered to be part of the present invention.

It is desirable to find new compounds with improved pharmacological characteristics compared with known MMP and/or TACE inhibitors. For example, it is preferred to find new compounds with improved MMP and/or TACE inhibitory activity and selectivity for an MMP and/or TACE versus other metalloproteases (e.g., specificity for one MMP versus another). It is also desirable and preferable to find compounds with advantageous and improved characteristics in one or more of the following categories: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

The compounds of the present invention act as inhibitors of MPs, in particular TACE, MMPs, or a combination thereof. These novel molecules are provided as anti-inflammatory compounds and cartilage protecting therapeutics. The inhibition of TACE and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, the present invention provides novel isoxazoline derivatives useful as MMP and/or TACE inhibitors or pharmaceutically acceptable salts or prodrugs thereof.

The present invention provides pharmaceutical compositions, comprising: a pharmaceutically acceptable carrier and a therapeutically effective amount of at least one of the compounds of the present invention or a pharmaceutically acceptable salt or prodrug form thereof.

The present invention provides a method for treating inflammatory disorders, comprising: administering to a host, in need of such treatment, a therapeutically effective amount of at least one of the compounds of the present invention or a pharmaceutically acceptable salt or prodrug form thereof.

The present invention provides a method of treating a condition or disease mediated by MMPs, TACE, or a combination thereof in a mammal, comprising: administering to the mammal in need of such treatment a therapeutically effective amount of a compound of the present invention or a pharmaceutically acceptable salt or prodrug form thereof.

The present invention provides a method comprising: administering a compound of the present invention or a pharmaceutically acceptable salt or prodrug form thereof in an amount effective to treat a condition or disease mediated by MMPs, TACE, or a combination thereof.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides novel compounds of the present invention for use in therapy.

The present invention provides the use of novel compounds of the present invention for the manufacture of a medicament for the treatment of a condition or disease mediated by MMPs, TACE, or a combination thereof.

These and other objects, which will become apparent during the following detailed description, have been achieved by the inventors' discovery that compounds of formulae I or II:

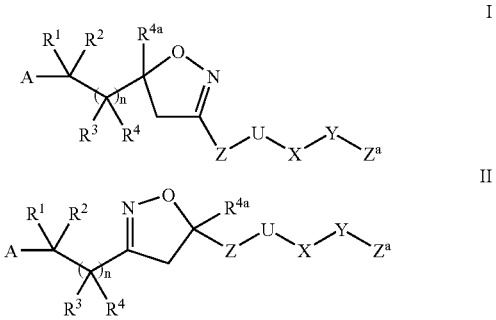

or a stereoisomer or pharmaceutically acceptable salt or prodrug forms thereof, wherein A, $R^1$, $R^2$, $R^3$, $R^4$, Z, U, X, Y, $Z^a$, and n are defined below, are effective as MMP and/or TACE inhibitors.

DETAILED DESCRIPTION OF PREFERRED EMBODIMENTS

In a first embodiment, the present invention provides a novel compound of formula I or II:

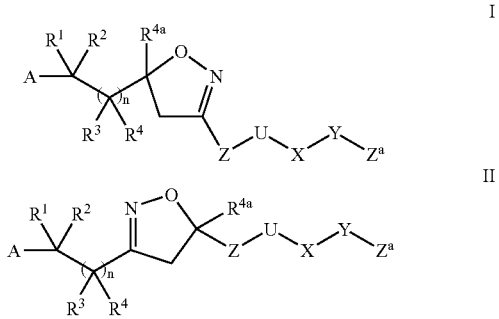

or a stereoisomer or pharmaceutically acceptable salt form thereof, wherein;

A is —C(O)NHOH, —C(O)NHOR$^5$, —C(O)NHOR$^6$, —N(OH)COR$^5$, or —N(OH)CHO;

U is absent or is O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X is absent or is $C_{1-10}$ alkylene, $C_{2-10}$ alkenylene, or $C_{2-10}$ alkynylene;

Y is absent or is O, NR$^{a1}$, S(O)$_p$, or C(O);

Z is a $C_{3-13}$ carbocycle substituted with 1–5 R$^b$, or a 5–14 membered heterocycle consisting of carbon atoms and 1–4 heteroatoms selected from N, O, and S(O)$_p$, and substituted with 1–5 R$^b$;

$Z^a$ is H, $C_{3-13}$ carbocycle substituted with 1–5 R$^c$, or a 5–14 membered heterocycle consisting of carbon atoms and 1–4 heteroatoms selected from N, O, and S(O)$_p$, and substituted with 1–5 R$^c$;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)O(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rNR^aC(O)NR^a(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, —$(CR^aR^{a1})_rNR^aSO_2(CR^aR^{a1})_s$-Q, or —$(CR^aR^{a1})_rNR^aSO_2NR^a(CR^aR^{a1})_s$-Q;

Q is, independently at each occurrence, H, $CHF_2$, $CH_2F$, $CF_3$, a $C_{3-13}$ carbocycle substituted with 0–5 $R^d$, or a 5–14 membered heterocycle consisting of carbon atoms and 1–4 heteroatoms selected from N, O, and $S(O)_p$, and substituted with 0–5 $R^d$;

$R^2$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rC(O)NR^aR^{a1}$, or —$(CR^aR^{a1})_rC(O)NR^a(CR^aR^{a1})_s$-$Q^1$;

$Q^1$ is, independently at each occurrence, H, a $C_{3-13}$ carbocycle substituted with 0–5 $R^d$, or a 5–14 membered heterocycle consisting of carbon atoms and 1–4 heteroatoms selected from N, O, and $S(O)_p$, and substituted with 0–5 $R^d$;

alternatively, $R^1$ and $R^2$ combine, along with the carbon atom to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

$R^3$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rNR^aC(O)NR^a(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, —$(CR^aR^{a1})_rNR^aSO_2(CR^aR^{a1})_s$-Q, or —$(CR^aR^{a1})_rNR^aSO_2NR^a(CR^aR^{a1})_s$-Q;

alternatively, $R^1$ and $R^3$ combine, along with the carbon atom to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

alternatively, when $R^1$ and $R^3$ combine to form a carbocyclic or heterocyclic ring, the $R^2$ and $R^4$ combine to form a double bond;

$R^4$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rC(O)NR^aR^{a1}$, or —$(CR^aR^{a1})_rC(O)NR^a(CR^aR^{a1})_s$-$Q^1$;

alternatively, $R^3$ and $R^4$ combine, along with the carbon atom to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

$R^{4a}$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^aOR^a$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rNR^aC(O)O(CR^aR^{a1})_s$-Q, —$(CR^aR^{a1})_rS(O)_p(CR^aR^{a1})_s$-Q, or —$(CR^aR^{a1})_rSO_2NR^a(CR^aR^{a1})_s$-Q;

alternatively, $R^1$ and $R^{4a}$ in Formula I combine, along with the carbon atoms to which they are attached, to form a 3–7 membered carbocyclic or heterocyclic ring consisting of: carbon atoms and 0–3 heteroatoms selected from the group consisting of N, O, and $S(O)_p$ and substituted with 0–3 $R^d$, provided that n is 0;

alternatively, $R^3$ and $R^{4a}$ in Formula I combine, along with the carbon atoms to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

$R^a$ is, independently at each occurrence, H, $C_{1-6}$ alkyl, phenyl, or benzyl;

$R^{a1}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

$R^{a2}$ is, independently at each occurrence, $C_{1-4}$ alkyl, phenyl, or benzyl;

$R^{a3}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^b$ is, independently at each occurrence, H, $C_{1-6}$ alkyl substituted with 0–1 $R^{c1}$, $OR^a$, $SR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, $CF_3$, $CF_2CF_3$, $CHF_2$, $CH_2F$, or phenyl;

$R^c$ is, independently at each occurrence, H, $OR^a$, Cl, F, Br, I, =O, CN, $NO_2$, $CF_3$, $CF_2CF_3$, $CH_2F$, $CHF_2$, —$(CR^aR^{a1})_rNR^aR^{a1}$, —$(CR^aR^{a1})_rC(=NCN)NR^aR^{a1}$, —$(CR^aR^{a1})_rC(=NR^a)NR^aR^{a1}$, —$(CR^aR^{a1})_rC(=NOR^a)NR^aR^{a1}$, —$(CR^aR^{a1})_rC(O)NR^aOH$, —$(CR^aR^{a1})_rC(O)R^{a1}$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$-$C_{3-10}$ carbocycle substituted with 0–2 $R^{c1}$, or —$(CR^aR^{a1})_r$-5–14 membered heterocycle consisting of carbon atoms and 1–4 heteroatoms selected from N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

$R^{c1}$ is, independently at each occurrence, H, $C_{1-4}$ alkyl, $OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, $OR^a$, Cl, F, Br, I, =O, CN, $NO_2$, —$NR^aR^{a1}$, —$C(O)R^a$, —$C(O)OR^a$, —$C(O)NR^aR^{a1}$, —$C(O)NR^aOR^a$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, $CF_3$, $CF_2CF_3$, $C_{3-10}$ carbocycle, or a 5–14 membered heterocycle consisting of carbon atoms and 1–4 heteroatoms selected from N, O, and $S(O)_p$;

$R^5$ is, independently at each occurrence, $C_{1-10}$ alkyl substituted with 0–2 $R^b$, or $C_{1-8}$ alkyl substituted with 0–2 $R^e$;

$R^e$ is phenyl substituted with 0–2 $R^b$, or biphenyl substituted with 0–2 $R^b$;

$R^6$ is, phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, or —$CH(R^8)OC(=O)OR^9$;

$R^7$ is H, $C_{1-10}$ alkyl, $C_{2-6}$ alkenyl, $C_{3-6}$ cycloalkyl-$C_{1-3}$ alkyl-, or phenyl-$C_{1-6}$ alkyl-;

$R^{7a}$ is H, $C_{1-10}$ alkyl, $C_{2-6}$ alkenyl, $C_{3-6}$ cycloalkyl-$C_{1-3}$ alkyl-, or phenyl-$C_{1-6}$ alkyl-;

$R^8$ is H or $C_{1-4}$ linear alkyl;

$R^9$ is H, $C_{1-8}$ alkyl substituted with 1–2 $R^f$, $C_{3-8}$ cycloalkyl substituted with 1–2 $R^f$, or phenyl substituted with 0–2 $R^b$;

$R^f$ is, independently at each occurrence, $C_{1-4}$ alkyl, $C_{3-8}$ cycloalkyl, $C_{1-5}$ alkoxy, or phenyl substituted with 0–2 $R^b$;

n is 0 or 1;

p, at each occurrence, is selected from 0, 1, and 2;

r, at each occurrence, is selected from 0, 1, 2, 3, and 4; and s, at each occurrence, is selected from 0, 1, 2, 3, and 4.

In a second embodiment, the present invention provides a novel compound of formula I, wherein:

U is absent or is O, $NR^{a1}$, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$;

X is absent or is $C_{1-3}$ alkylene or $C_{3-4}$ alkynylene;

Y is absent or is O, $NR^{a1}$, $S(O)_p$, or C(O);

Z is a $C_{5-10}$ carbocycle substituted with 1–3 $R^b$, or a 5–10 membered heterocycle consisting of carbon atoms and 1–4 heteroatoms selected from N, O, and $S(O)_p$, and substituted with 1–3 $R^b$;

$Z^a$ is H, $C_{3-13}$ carbocycle substituted with 1–3 $R^c$, or a 5–14 membered heterocycle consisting of carbon atoms and 1–4 heteroatoms selected from N, O, and $S(O)_p$, and substituted with 1–3 $R^c$;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)O(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q;

Q is, independently at each occurrence, H, $CHF_2$, $CH_2F$, $CF_3$, a $C_{3-13}$ carbocycle substituted with 0–3 $R^d$, or a 5–14 membered heterocycle consisting of carbon atoms and 1–4 heteroatoms selected from N, O, and $S(O)_p$, and substituted with 0–3 $R^d$;

$R^2$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, or —$(CR^aR^{a1})_rC(O)NR^a(CR^aR^{a1})_s$-$Q^1$;

$Q^1$ is, independently at each occurrence, H, a $C_{3-10}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

alternatively, $R^1$ and $R^2$, when attached to the same carbon atom, combine to form a 5–6 membered carbocyclic or heterocyclic ring consisting of: carbon atoms and 0–3 heteroatoms selected from the group consisting of N, O, and $S(O)_p$ and substituted with 0–2 $R^d$;

$R^3$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rNR^aC(O)NR^a(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, —$(CR^aR^{a1})_rNR^aSO_2(CR^aR^{a1})_s$-Q, or —$(CR^aR^{a1})_rNR^aSO_2NR^a(CR^aR^{a1})_s$-Q;

alternatively, $R^1$ and $R^3$ combine, along with the carbon atom to which they are attached, to form a 4–7 membered carbocyclic or heterocyclic ring consisting of: carbon atoms and 0–3 heteroatoms selected from the group consisting of N, O, and $S(O)_p$ and substituted with 0–2 $R^d$;

alternatively, when $R^1$ and $R^3$ combine to form a carbocyclic or heterocyclic ring, the $R^2$ and $R^4$ combine to form a double bond;

$R^4$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, or —$(CR^aR^{a1})_rC(O)NR^a(CR^aR^{a1})_s$-$Q^1$;

alternatively, $R^3$ and $R^4$ combine, along with the carbon atom to which they are attached, to form a 4–7 membered carbocyclic or heterocyclic ring consisting of: carbon atoms and 0–3 heteroatoms selected from the group consisting of N, O, and $S(O)_p$ and substituted with 0–2 $R^d$;

$R^{4a}$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^aOR^a$, —$(CR^aR^{a1})_rC(O)NR^a(CR^aR^{a1})_s$-Q, —$(CR^aR^{a1})_rNR^aC(O)(CR^aR^{a1})_s$-Q, or —$(CR^aR^{a1})_rSO_2NR^a(CR^aR^{a1})_s$-Q;

alternatively, $R^1$ and $R^{4a}$ in Formula I combine, along with the carbon atoms to which they are attached, to form a 4–7 membered carbocyclic or heterocyclic ring consisting of: carbon atoms and 0–3 heteroatoms selected from the group consisting of N, O, and $S(O)_p$ and substituted with 0–3 $R^d$, provided that n is 0;

alternatively, $R^3$ and $R^{4a}$ in Formula I combine, along with the carbon atoms to which they are attached, to form a 4–7 membered carbocyclic or heterocyclic ring consisting of: carbon atoms and 0–3 heteroatoms selected from the group consisting of N, O, and $S(O)_p$ and substituted with 0–2 $R^d$;

$R^a$ is, independently at each occurrence, H, $C_{1-6}$ alkyl, phenyl, or benzyl;

$R^{a1}$ is, independently at each occurrence, H, $C_{1-6}$ alkyl, $C_{2-6}$ alkenyl, $C_{2-6}$ alkynyl, or $-(CH_2)_r$-3–8 membered carbocyclic or heterocyclic ring consisting of carbon atoms and 0–2 ring heteroatoms selected from N, $NR^{a2}$, O, and $S(O)_p$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

$R^c$ is, independently at each occurrence, H, $OR^a$, Cl, F, Br, $=O$, CN, $NO_2$, $CF_3$, $CH_2F$, $CHF_2$, $CF_2CF_3$, $-(CR^aR^{a1})_r NR^aR^{a1}$, $-(CR^aR^{a1})_r C(O)R^{a1}$, $-(CR^aR^{a1})_r C(O)OR^{a1}$, $-(CR^aR^{a1})_r C(O)NR^aR^{a1}$, $-(CR^aR^{a1})_r NR^aC(O)R^{a1}$, $-(CR^aR^{a1})_r S(O)_p R^{a3}$, $-(CR^aR^{a1})_r SO_2 NR^aR^{a1}$, $-(CR^aR^{a1})_r NR^a SO_2 R^{a3}$, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, $-(CH_2)_r$-$C_{3-6}$ carbocycle substituted with 0–2 $R^{c1}$, or $-(CH_2)_r$-5–6 membered heterocycle consisting of carbon atoms and 1–4 heteroatoms selected from N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

$R^d$ is, independently at each occurrence, $C_{1-6}$ alkyl, $OR^a$, Cl, F, Br, $=O$, CN, $NO_2$, $-NR^aR^{a1}$, $-C(O)R^a$, $-C(O)OR^a$, $-C(O)NR^aR^{a1}$, $-S(O)_2 NR^aR^{a1}$, $-NR^a S(O)_2 R^{a3}$, $-S(O)_p R^{a3}$, $CF_3$, $C_{3-6}$ carbocycle, or a 5–6 membered heterocycle consisting of carbon atoms and 1–4 heteroatoms selected from N, O, and $S(O)_p$;

$R^5$ is, independently at each occurrence, $C_{1-6}$ alkyl substituted with 0–2 $R^b$, or $C_{1-4}$ alkyl substituted with 0–2 $R^e$; and $R^f$ is, independently at each occurrence, $C_{1-4}$ alkyl, $C_{3-6}$ cycloalkyl, $C_{1-5}$ alkoxy, or phenyl substituted with 0–2 $R^b$.

In a third embodiment, the present invention provides a novel compound of formula I, wherein;

A is $-C(O)NHOH$ or $-N(OH)CHO$;

U is absent or is O, $NR^{a1}$, $C(O)$, $CR^a(OH)$, $C(O)NR^{a1}$, $NR^{a1}C(O)$, $S(O)_p$, $S(O)_p NR^{a1}$, or $NR^{a1}S(O)_p$;

X is absent or is methylene, ethylene, propynylene, or butynylene;

Z is a $C_{5-10}$ carbocycle substituted with 1–2 $R^b$, or a 5–10 membered heterocycle consisting of carbon atoms and 1–4 heteroatoms selected from N, O, and $S(O)_p$, and substituted with 1–2 $R^b$;

$Z^a$ is H, $C_{5-10}$ carbocycle substituted with 1–3 $R^c$, or a 5–10 membered heterocycle consisting of carbon atoms and 1–4 heteroatoms selected from N, O, and $S(O)_p$, and substituted with 1–3 $R^c$;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, $C_{2-6}$ alkenylene-Q, $C_{2-6}$ alkynylene-Q, $-(CR^aR^{a1})_r O(CR^aR^{a1})_s$-Q, $-(CR^aR^{a1})_r NR^a (CR^aR^{a1})_s$-Q, $-(CR^aR^{a1})_r C(O)(CR^aR^{a1})_s$-Q, $-(CR^aR^{a1})_r C(O)O(CR^aR^{a1})_s$-Q, $-(CR^aR^{a1})_r C(O)NR^aR^{a1}$, $-(CR^aR^{a1})_r C(O)NR^a (CR^aR^{a1})_s$-Q, $-(CR^aR^{a1})_r NR^a C(O)(CR^aR^{a1})_s$-Q, $-(CR^aR^{a1})_r OC(O)NR^a (CR^aR^{a1})_s$-Q, $-(CR^aR^{a1})_r NR^a C(O)O(CR^aR^{a1})_s$-Q, $-(CR^aR^{a1})_r S(O)_p (CR^aR^{a1})_s$-Q, $-(CR^aR^{a1})_r SO_2 NR^a (CR^aR^{a1})_s$-Q, or $-(CR^aR^{a1})_r NR^a SO_2 (CR^aR^{a1})_s$-Q;

Q is, independently at each occurrence, H, a $C_{3-8}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

$R^2$ is $Q^1$, $C_{1-6}$ alkylene-$Q^1$, $C_{2-6}$ alkenylene-$Q^1$, $-(CR^aR^{a1})_r O(CR^aR^{a1})_s$-$Q^1$, $-(CR^aR^{a1})_r NR^a (CR^aR^{a1})_s$-$Q^1$, or $-(CR^aR^{a1})_r C(O)(CR^aR^{a1})_s$-$Q^1$, $Q^1$ is, independently at each occurrence, H, a $C_{5-10}$ carbocycle substituted with 0–2 $R^d$, or a 5–10 membered heterocycle consisting of carbon atoms and 1–4 heteroatoms selected from N, O, and $S(O)_p$, and substituted with 0–2 $R^d$;

$R^3$ is Q, $C_{1-6}$ alkylene-Q, $C_{2-6}$ alkenylene-Q, $C_{2-6}$ alkynylene-Q, $-(CR^aR^{a1})_r O(CR^aR^{a1})_s$-Q, $-(CR^aR^{a1})_r NR^a (CR^aR^{a1})_s$-Q, $-(CR^aR^{a1})_r C(O)(CR^aR^{a1})_s$-Q, $-(CR^aR^{a1})_r NR^a C(O)(CR^aR^{a1})_s$-Q, $-(CR^aR^{a1})_r NR^a C(O)O(CR^aR^{a1})_s$-Q, $-(CR^aR^{a1})_r NR^a C(O)NR^a (CR^aR^{a1})_s$-Q, $-(CR^aR^{a1})_r S(O)_p (CR^aR^{a1})_s$-Q, $-(CR^aR^{a1})_r SO_2 NR^a (CR^aR^{a1})_s$-Q, or $-(CR^aR^{a1})_r NR^a SO_2 (CR^aR^{a1})_s$-Q;

$R^4$ is $Q^1$, $C_{1-6}$ alkylene-$Q^1$, $C_{2-6}$ alkenylene-$Q^1$, $-(CR^aR^{a1})_r O(CR^aR^{a1})_s$-$Q^1$, $-(CR^aR^{a1})_r NR^a (CR^aR^{a1})_s$-$Q^1$, or $-(CR^aR^{a1})_r C(O)(CR^aR^{a1})_s$-$Q^1$, $R^{4a}$ is Q, $C_{1-4}$ alkylene-Q, $-(CH_2)_r O(CH_2)_s$-Q, $-(CH_2)_r NR^a (CH_2)_s$-Q, $-(CH_2)_r C(O)(CH_2)_s$-Q, $-(CH_2)_r C(O)(CH_2)_s$-Q, $-(CH_2)_r C(O)NR^aR^{a1}$, $-(CH_2)_r C(O)NR^a OR^a$, $-(CH_2)_r C(O)NR^a (CH_2)_s$-Q, $-(CH_2)_r NR^a C(O)(CH_2)_s$-Q, or $-(CH_2)_r NR^a C(O)O(CH_2)_s$-Q;

$R^{a3}$ is, independently at each occurrence, H, $C_{1-6}$ alkyl, $C_{2-6}$ alkenyl, or $-(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^c$ is, independently at each occurrence, H, $OR^a$, Cl, F, Br, $=O$, $CF_3$, $CH_2F$, $CHF_2$, $-(CR^aR^{a1})_r NR^aR^{a1}$, $-(CR^aR^{a1})_r C(O)R^{a1}$, $-(CR^aR^{a1})_r C(O)OR^{a1}$, $-(CR^aR^{a1})_r C(O)NR^aR^{a1}$, $-(CR^aR^{a1})_r NR^a C(O)R^{a1}$, $-(CR^aR^{a1})_r S(O)_p R^{a3}$, $-(CR^aR^{a1})_r SO_2 NR^aR^{a1}$, $-(CR^aR^{a1})_r NR^a SO_2 R^{a3}$, $C_{1-6}$ alkyl, $C_{2-6}$ alkenyl, $C_{2-6}$ alkynyl, $C_{3-6}$ cycloalkyl substituted with 0–1 $R^{c1}$, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

$R^d$ is, independently at each occurrence, $C_{1-6}$ alkyl, $OR^a$, Cl, F, Br, $=O$, $-NR^aR^{a1}$, $-C(O)R^a$, $-C(O)OR^a$, $-C(O)NR^aR^{a1}$, $-S(O)_2 NR^aR^{a1}$, $-NR^a S(O)_2 R^{a3}$, $-S(O)_p R^{a3}$, $CF_3$, or phenyl;

$R^5$ is, independently at each occurrence, $C_{1-4}$ alkyl substituted with 0–2 $R^b$, or $C_{1-4}$ alkyl substituted with 0–2 $R^e$;

r, at each occurrence, is selected from 0, 1, 2, and 3; and s, at each occurrence, is selected from 0, 1, 2, and 3.

In a fourth embodiment, the present invention provides a novel compound wherein:

A is —C(O)NHOH;

Z is phenyl substituted with 1–2 $R^b$, naphthyl substituted with 1–2 $R^b$, or pyridyl substituted with 1–2 $R^b$;

$Z^a$ is phenyl substituted with 1–3 $R^c$, naphthyl substituted with 1–3 $R^c$, or a heterocycle substituted with 1–3 $R^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, and pyrazolo[1,5-a]pyridinyl;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is selected from Q, $C_{1-6}$ alkylene-Q, —$(CR^aR^{a1})_r$O $(CR^aR^{a1})_s$-Q, —$(CR^aR^{a1})_r$NR$^a$$(CR^aR^{a1})_s$-Q, —$(CR^aR^{a1})_r$C(O)$(CR^aR^{a1})_s$-Q, —$(CR^aR^{a1})_r$C(O)O$(CR^aR^{a1})_s$-Q, —$(CR^aR^{a1})_r$C(O)NR$^a$R$^{a1}$, —$(CR^aR^{a1})_r$C(O)NR$^a$$(CR^aR^{a1})_s$-Q, —$(CR^aR^{a1})_r$NR$^a$C(O) $(CR^aR^{a1})_s$-Q, or —$(CR^aR^{a1})_r$NR$^a$C(O)O$(CR^aR^{a1})_s$-Q;

Q is, independently at each occurrence, H, a $C_{3-6}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

$R^2$ is $Q^1$ or $C_{1-6}$ alkylene-$Q^1$, $Q^1$ is, independently at each occurrence, H, phenyl substituted with 0–2 $R^d$, or a 5–6 membered heterocycle consisting of carbon atoms and 1–4 heteroatoms selected from N, O, and $S(O)_p$, and substituted with 0–2 $R^d$;

$R^3$ is Q, $C_{1-4}$ alkylene-Q, $C_{2-4}$ alkenylene-Q, $C_{2-4}$ alkynylene-Q, —$(CR^aR^{a1})_r$NR$^a$$(CR^aR^{a1})_s$-Q, —$(CR^aR^{a1})_r$NR$^a$C(O)$(CR^aR^{a1})_s$-Q, —$(CR^aR^{a1})_r$NR$^a$C(O)O$(CR^aR^{a1})_s$-Q, —$(CR^aR^{a1})_r$NR$^a$C(O)NR$^a$$(CR^aR^{a1})_s$-Q, —$(CR^aR^{a1})_r$S(O)$_p$$(CR^aR^{a1})_s$-Q, —$(CR^aR^{a1})_r$SO$_2$NR$^a$$(CR^aR^{a1})_s$-Q, or —$(CR^aR^{a1})_r$NR$^a$SO$_2$$(CR^aR^{a1})_s$-Q;

$R^4$ is $Q^1$ or $C_{1-6}$ alkylene-$Q^1$;

$R^{4a}$ is Q, —CH$_2$-Q, —CH$_2$O(CH$_2$)$_s$-Q, —CH$_2$NR$^a$(CH$_2$)$_s$-Q, —CH$_2$C(O)(CH$_2$)$_s$-Q, —CH$_2$C(O)O (CH$_2$)$_s$-Q, —CH$_2$C(O)NR$^a$R$^{a1}$, —(CH$_2$)$_r$C(O)NR$^a$OR$^a$, —CH$_2$C(O)NR$^a$(CH$_2$)$_s$-Q, —CH$_2$NR$^a$C(O)(CH$_2$)$_s$-Q, or —CH$_2$NR$^a$C(O)O(CH$_2$)$_s$-Q;

$R^{a1}$ is, independently at each occurrence, H, $C_{1-6}$ alkyl, phenyl, or benzyl;

$R^{a3}$ is, independently at each occurrence, H, $C_{1-6}$ alkyl, phenyl, or benzyl;

$R^c$ is, independently at each occurrence, H, OR$^a$, Cl, F, Br, =O, CF$_3$, CH$_2$F, CHF$_2$, —NR$^a$R$^{a1}$, —$(CR^aR^{a1})_r$NR$^a$R$^{a1}$, —$(CR^aR^{a1})_r$C(O)R$^{a1}$, —$(CR^aR^{a1})_r$C(O)OR$^{a1}$, —$(CR^aR^{a1})_r$C(O)NR$^a$R$^{a1}$, —$(CR^aR^{a1})_r$NR$^a$C(O)R$^{a1}$, —$(CR^aR^{a1})_r$S(O)$_p$R$^{a3}$, —$(CR^aR^{a1})_r$SO$_2$NR$^a$R$^{a1}$, —$(CR^aR^{a1})_r$NR$^a$SO$_2$R$^{a3}$, $C_{1-6}$ alkyl, $C_{2-6}$ alkenyl, $C_{2-6}$ alkynyl, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$; and alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of: carbon atoms and 0–2 heteroatoms selected from N, O, and $S(O)_p$.

In a fifth embodiment, the present invention provides a novel compound of formula I, wherein;

U is absent or is O, NR$^{a1}$, C(O), CR$^a$(OH), C(O)NR$^{a1}$, or NR$^{a1}$C(O);

X is absent or is methylene or butynylene;

Y is absent or is 0;

Z is phenyl substituted with 1–2 $R^b$;

$Z^a$ is naphthyl substituted with 1–3 $R^c$, or a heterocycle substituted with 1–3 $R^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, pyranyl, pyrazinyl, pyrazolyl, pyridoimidazolyl, pyrrolidinyl, pyrrolyl, quinolinyl, tetrahydroquinolinyl, isoquinolinyl, tetrahydro-isoquinolinyl, imidazolyl, benzimidazolyl, benzothiazinyl, benzofuranyl, benzothiophenyl, benzoxazolyl, benzthiazolyl, benztriazolyl, benzisoxazolyl, benzisothiazolyl, indolyl, indolinyl, indazolyl, isobenzofuranyl, isoindazolyl, isoindolinyl, isoindolyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, and pyrazolo[1,5-a]pyridinyl;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, —$(CR^aR^{a1})_r$NR$^a$$(CR^aR^{a1})_s$-Q, or —$(CR^aR^{a1})_r$NR$^a$C(O)O$(CR^aR^{a1})_s$-Q;

Q is, independently at each occurrence, H, a $C_{3-6}$ carbocycle substituted with 0–3 $R^d$, or a 5–6 membered heterocycle consisting of carbon atoms and 1–4 heteroatoms selected from N, O, and $S(O)_p$, and substituted with 0–3 $R^d$;

$R^2$ is H or $C_{1-6}$ alkylene-$Q^1$, $R^3$ is Q, $C_{1-4}$ alkylene-Q, $C_{2-4}$ alkenylene-Q, $C_{2-4}$ alkynylene-Q, —(CH$_2$)$_r$NR$^a$(CH$_2$)$_s$-Q, —(CH$_2$)$_r$NR$^a$C(O)(CH$_2$)$_s$-Q, —(CH$_2$)$_r$NR$^a$C(O)O$(CR^aR^{a1})_s$-Q, —(CH$_2$)$_r$NR$^a$C(O)NR$^a$(CH$_2$)$_s$-Q, —(CH$_2$)$_r$S(O)$_p$(CH$_2$)$_s$-Q, or —(CH$_2$)$_r$NR$^a$SO$_2$(CH$_2$)$_s$-Q;

$R^4$ is H or $C_{1-6}$ alkylene-$Q^1$;

$R^{4a}$ is Q, —CH$_2$-Q, —CH$_2$O-Q, —CH$_2$NR$^a$-Q, —CH$_2$C (O)$_s$-Q, —CH$_2$C(O)O-Q, —CH$_2$C(O)NR$^a$R$^{a1}$, —C(O) NR$^a$OR$^a$, —CH$_2$C(O)NR$^a$-Q, or —CH$_2$NR$^a$C(O)O-Q;

$R^a$ is, independently at each occurrence, H, or $C_{1-4}$ alkyl;

$R^{a1}$ is, independently at each occurrence, H, or $C_{1-4}$ alkyl;

$R^{a3}$ is, independently at each occurrence, H, $C_{1-4}$ alkyl, phenyl, or benzyl;

$R^c$ is, independently at each occurrence, $C_{1-6}$ alkyl, $C_{2-6}$ alkenyl, $C_{2-6}$ alkynyl, OR$^a$, Cl, F, Br, =O, CF$_3$, CH$_2$F, CHF$_2$, —NR$^a$R$^{a1}$, —$(CR^aR^{a1})_r$C(O)R$^{a1}$, —$(CR^aR^{a1})_r$C(O)OR$^{a1}$, —$(CR^aR^{a1})_r$C(O)NR$^a$R$^{a1}$, —$(CR^aR^{a1})_r$NR$^a$C(O)R$^{a1}$, —$(CR^aR^{a1})_r$S(O)$_p$R$^{a3}$, —$(CR^aR^{a1})_r$SO$_2$NR$^a$R$^{a1}$, —$(CR^aR^{a1})_r$NR$^a$SO$_2$R$^{a3}$, or phenyl; and alternatively, when two $R^c$ groups are attached to adjacent carbon atoms, together with the carbon atoms to which they are attached they form a 5–6 membered carbocyclic or heterocyclic ring D substituted with 0–1 $R^{c1}$ and consisting of: carbon atoms and 0–2 heteroatoms selected from N, O, and $S(O)_p$.

In a sixth embodiment, the present invention provides a novel compound wherein:

U is absent or is O, $NR^{a1}$, C(O), or $CR^a(OH)$;

Y is absent;

$R^1$ is H, $C_{1-4}$ alkylene-Q, $-(CH_2)_rNR^a(CH_2)_s$-Q, or $-(CH_2)_rNR^aC(O)O(CR^aR^{a1})_s$-Q;

$R^2$ is H, $CH_3$, $CH_2CH_3$, $CH_2CH_2CH_3$, or $CH(CH_3)_2$;

$R^3$ is Q, $C_{1-4}$ alkylene-Q, $-(CH_2)_rNR^a(CH_2)_s$-Q, $-(CH_2)_rNR^aC(O)(CH_2)_s$-Q, $-(CH_2)_rNR^aC(O)O(CR^aR^{a1})_s$-Q, $-(CH_2)_rNR^aC(O)NR^a(CH_2)_s$-Q, $-(CH_2)_rS(CH_2)_s$-Q, or $-(CH_2)_rNR^aSO_2(CH_2)_s$-Q;

$R^4$ is H, $CH_3$, $CH_2CH_3$, $CH_2CH_2CH_3$, or $CH(CH_3)_2$;

$R^{4a}$ is Q, $-CH_2$-Q, $-CH_2O$-Q, $-CH_2NR^a$-Q, $-CH_2C(O)_s$-Q, $-CH_2C(O)O$-Q, $-CH_2C(O)NR^aR^{a1}$, $-C(O)NR^aOR^a$, or $-CH_2C(O)NR^a$-Q;

r, at each occurrence, is selected from 0, 1, and 2; and s, at each occurrence, is selected from 0, 1, and 2.

In a seventh embodiment, the present invention provides a novel compound, wherein:

U is O, $NR^{a1}$, or $CR^a(OH)$;

$Z^a$ is naphthyl substituted with 1–3 $R^c$, or a heterocycle substituted with 1–3 $R^c$ and selected from pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, pyrazolyl, and pyrazolo[1,5-a]pyridinyl;

$R^1$ is H, $CH_3$, $CH_2CH_3$, $CH_2CH_2CH_3$, $CH(CH_3)_2$, $NH_2$, or $-NHC(O)OC(CH_3)_3$;

$R^2$ is H or $CH_3$;

$R^3$ is Q, $C_{1-4}$ alkylene-Q, $-NR^a(CH_2)_s$-Q, $-NR^aC(O)(CH_2)_s$-Q, $-NR^aC(O)O(CR^aR^{a1})_s$-Q, $-NR^aC(O)NR^a(CH_2)_s$-Q, $-S(CH_2)_s$-Q, or $-NR^aSO_2(CH_2)_s$-Q;

$R^{4a}$ is Q, $-CH_2$-Q, $-CH_2O$-Q, $-CH_2NR^a$-Q, or $-C(O)NR^aOR^a$;

Q is, independently at each occurrence, H, phenyl substituted with 0–3 $R^d$, or a 5–6 membered heterocycle consisting of carbon atoms and 1–2 heteroatoms selected from N, O, and $S(O)_p$, and substituted with 0–3 $R^d$;

$R^b$ is, independently at each occurrence, H, $C_{1-6}$ alkyl, $OR^a$, Cl, F, Br, $-NR^aR^{a1}$, $-C(O)R^a$, $-C(O)OR^a$, $-C(O)NR^aR^{a1}$, $-S(O)_2NR^aR^{a1}$, $-NR^aS(O)_2R^{a3}$, $-S(O)_pR^{a3}$, or $CF_3$;

$R^c$ is, independently at each occurrence, $C_{1-6}$ alkyl, $C_{2-6}$ alkenyl, $C_{2-6}$ alkynyl, $OR^a$, Cl, F, Br, =O, $CF_3$, $-NR^aR^{a1}$, $-(CR^aR^{a1})_rC(O)R^{a1}$, $-(CR^aR^{a1})_rC(O)OR^{a1}$, $-(CR^aR^{a1})_r$ $C(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, or $-(CR^aR^{a1})_rNR^aSO_2R^{a3}$; and alternatively, when two $R^c$ groups are attached to adjacent carbon atoms, together with the carbon atoms to which they are attached they form a 5–6 membered saturated ring consisting of: carbon atoms and 0–1 heteroatoms selected from N, O, and $S(O)_p$.

In an eighth embodiment, the present invention provides a novel compound selected from Examples 1–43 or a stereoisomer or pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, or a combination thereof in a mammal, comprising: administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, or a combination thereof.

In another embodiment, the present invention provides a novel method of treating a disease or condition selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthopathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthosis, Lyme disease, meningitis, multiple sclerosis, myasthenia gravis, mycobacterial infection, neovascular glaucoma, osteoarthitis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, or a combination thereof.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat an inflammatory disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "independently selected from", "independently, at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

It is understood by one skilled in the art that in Formula I, once $R^2$ and $R^3$ together with the carbon atom to which they are attached combine to form a ring, $R^3$ is not available to form a ring with $R^4$. Similarly, once $R^3$ and $R^4$ together with the carbon atom to which they are attached combine to form a ring, $R^4$ is not available to form a ring with $R^5$.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ wherein v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached though an oxygen bridge.

$C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chomanyl, chomenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochomanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthidinyl, phenantholinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

The phase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e, =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

The compounds of Formula I may be prepared as outlined in Scheme 1 below. An appropriately substituted aldehyde of formula 1, wherein R is a protecting group or alternatively the requisite terminal group, can be reacted with hydroxylamine under a variety of conditions well known in the literature for conversion of an aldehyde to an oxime, e.g., hydroxylamine and sodium methoxide in methanol. The oxime compound of formula 2 can be combined in a solvent like THF or methylene chloride with an appropriately substituted olefin of formula 3 and reacted with Clorox®, to give the isoxazoline compound of formula 4. Alternatively the oxime compound of formula 2 can be reacted with NCS to give a chlorooxime, which can be combined with the appropriate olefin compound of formula 3 and a base like triethylamine to give the isoxazoline compound of formula 4. When the protecting group R is a benzyl group, it may be removed by catalytic hydrogenation with Pd/C to give the intermediate compound of formula 5. Compound 5 can be reacted with an appropriately substituted terminal group, Za-CH$_2$X where X is Cl, Br, or mesylate (e.g., 2-methyl-4-chloromethyl quinoline), in acetonitrile with potassium carbonate at reflux or DMSO with cesium carbonate to give compounds of formula 6. The ester of compound formula 6 can be converted to the corresponding hydroxamic acid in a solution of KOH/MeOH/NH$_2$OH or NaOMe/MeOH/NH$_2$OH at an appropriate temperature to give the compound of formula 7. Alternatively the ester of formula 4 may be saponified with an aqueous base like lithium hydroxide in methanol/water combinations to give the carboxylic acid compound of formula 8. The hydroxamic acid compound of formula 7 can be prepared from the carboxylic acid compound of formula 8 by making an activated acid with reagents such as BOP, isobutylchloroformate, or acid chloride, well known in the peptide literature, and reacting with hydroxylamine. The diasteromers may be separated by HPLC chromatography at any step in the synthesis where separation is reasonable.

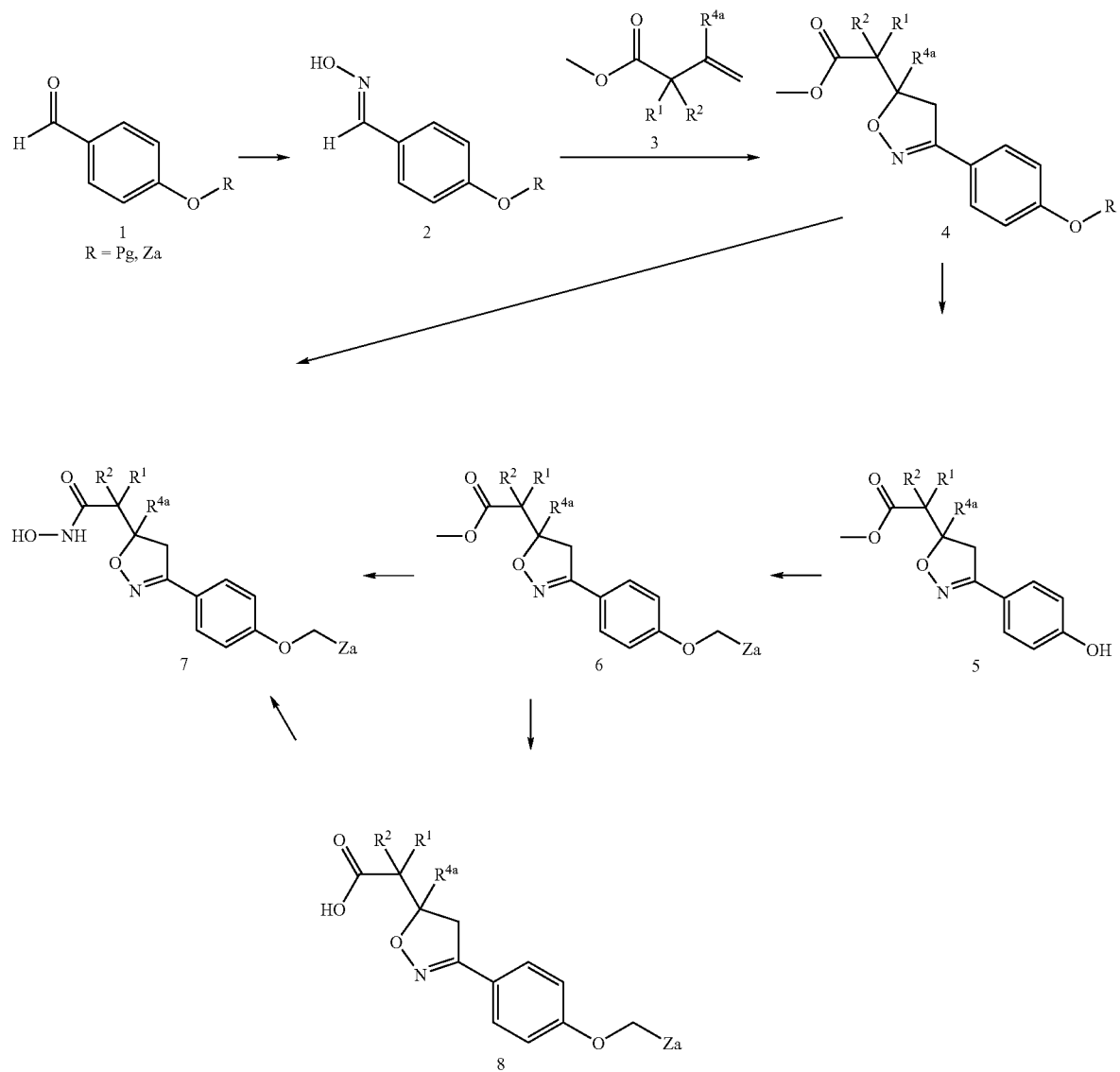

Scheme 1

The compound of formula 10 may be prepared as outlined in Scheme 2 below. The appropriately substituted diene compound of formula 9 may be be reacted with the oxime compound of formula 2 by methods previously described (e.g., Clorox® in THF), to give the isoxazoline compound of formula 10. Alternatively, the isoxazoline compound of formula 10 may be prepared by reacting a protected propenal compound of formula 13 with the oxime compound of formula 2 by methods previously described, to give the isoxazoline compound of formula 14. The aldehyde-protecting group may be removed with conditions appropriate for the group, e.g., 6 N HCl when the dimethyl acetal is used, to give compound of formula 15. The crotonate compound of formula 10 may be prepared from the aldehyde compound of formula 15 by methods well known in the literature, for example, methyl(triphenylphosphoranylidene)acetate or trimethyl phosphonoacetate with a base (e.g., sodium hydride) in solvents such as DMF or THF. The substituted isoxazoline compound of formula 11, may be prepared by reaction of a nuclophile (e.g., ammonia, substituted amines, thioacetate, and substituted thios) solvents and temperatures appropriate to carry out the Michael-like reactions on compounds of formula 10. When the nucleophile is ammonia, the nitrogen can be further modified by reaction of compounds of formula 11 with acid chlorides, activated esters, or isocyanates. Alternatively the amine of formula 11 wherein Nu is $NH_2$ may be reductively alkylated with appropriate aldehydes and reducing agents (e.g., sodium triacetoxyborohydride) in solvents such as THF or 1,2-dichloroethane.

Scheme 2
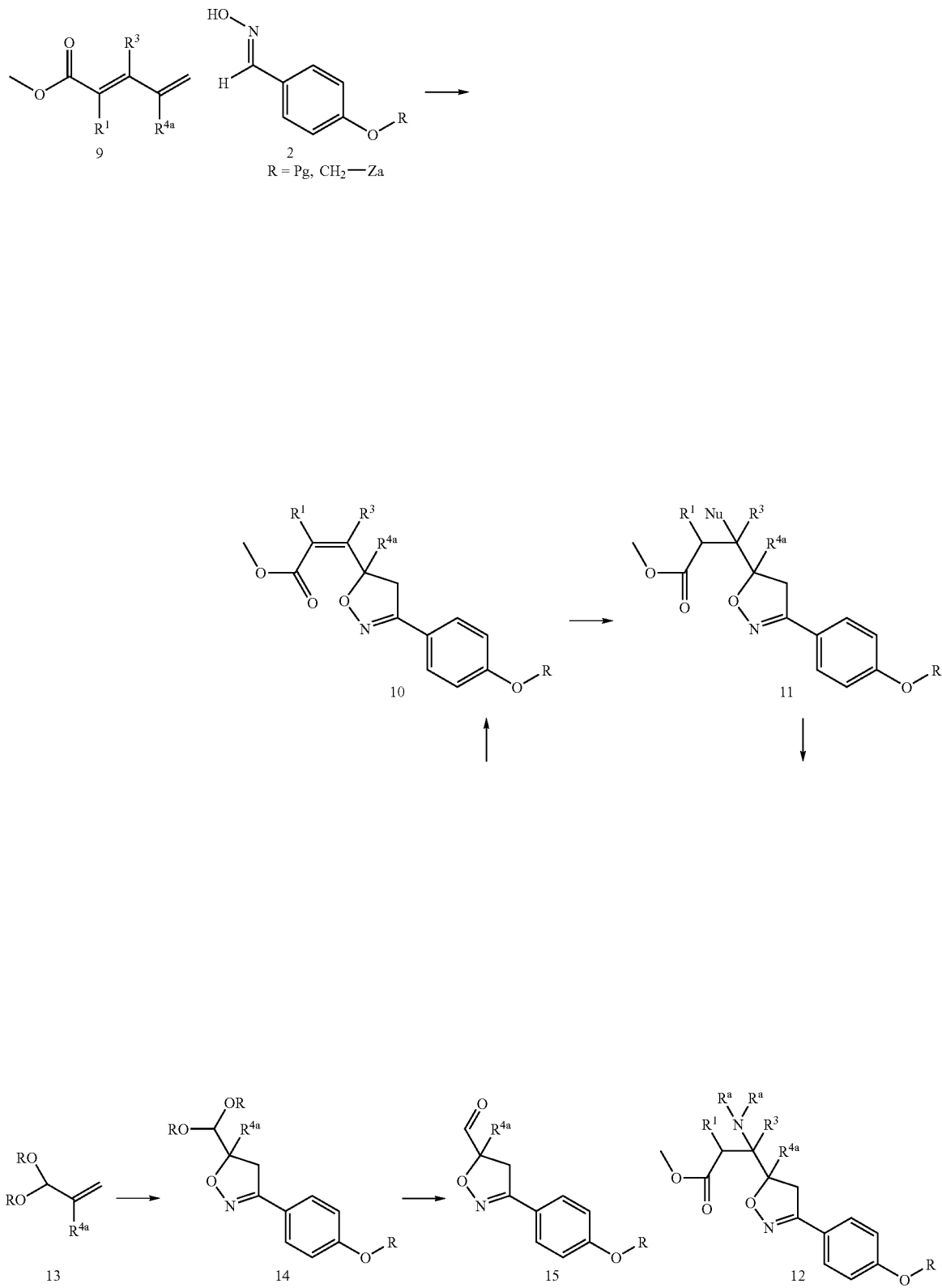

The spiro isoxazoline compound of formula 19, may be prepared as outlined in Scheme 3. The appropriately substituted cyclic ketone compound of formula 16 can be reacted with the phosphonium ylid generated from methyl triphenylphosphonium bromide and a base (e.g., sodium hydride) in a solvent (e.g., DMF or THF) to give the olefin compound of formula 17. The olefin compound of formula 17 can be reacted with the oxime compound of formula 2 by methods previously described, to give the Spiro isoxazoline compound of formula 18. The ester of compound formula 18 may be converted to the corresponding hydroxamic acid in a solution of KOH/MeOH/NH$_2$OH or NaOMe/MeOH/NH$_2$OH at an appropriate temperature to give the compound of formula 19. The diasteromers may be separated by HPLC chromatography at any step in the synthesis where separation is reasonable.

tube at an elevated temperature. The olefin compound of formula 22 can be reacted with the oxime compound of formula 2 by methods previously described, to give the isoxazoline compound of formula 23.

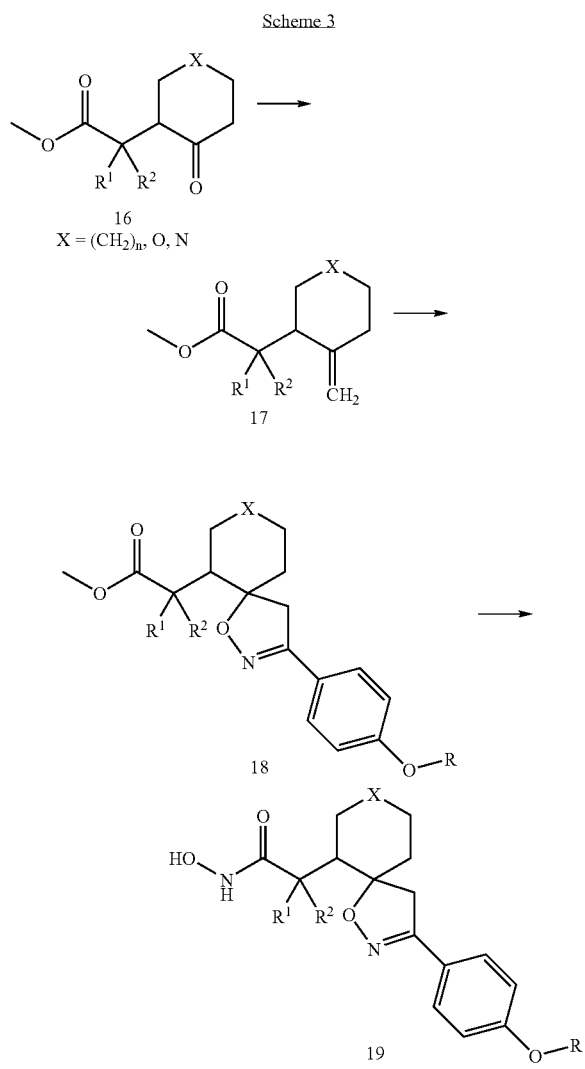

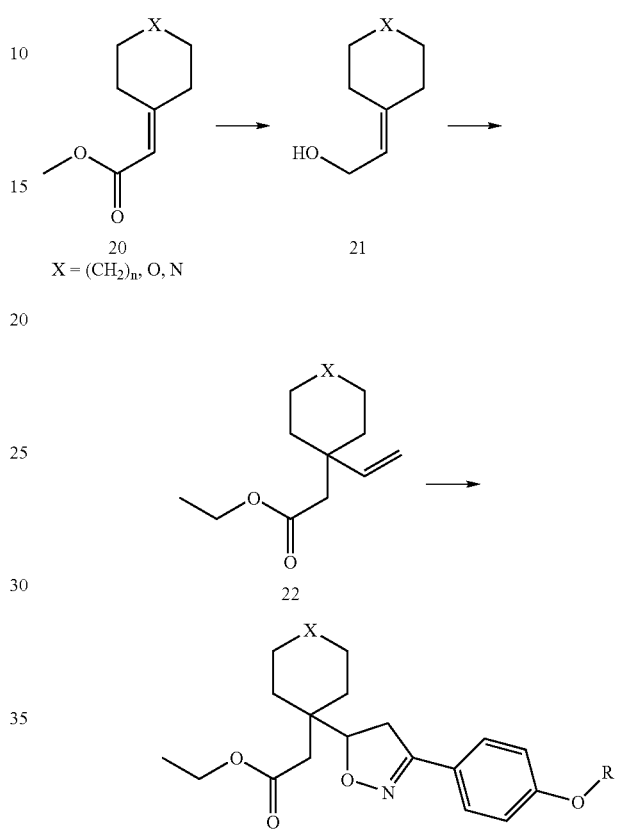

The isoxazoline compounds of formula 23 can be prepared as outlined in Scheme 4. The crotonate compound of formula 20 may be reacted with DIBAL in an appropriate solvent like THF at low temperature to give the allylic alcohol compound of formula 21. The olefin compound of formula 22 can be prepared by reaction of triethylorthoacteate and a catalytic amount of propionic acid in a sealed The compound of formula 24 can be prepared as outlined in Scheme 5. The triflate compound of formula 26 may be prepared from the appropriately substituted cyclic ketone compound of formula 25 with triflic anhydride and a base (e.g., diisopropylethyl amine) in THF. The olefin compound of formula 27 may be prepared by palladium mediated olefination using tributyl(vinyl)tin and palladium (II) acetate with triphenyl phosphine in an appropriate solvent. The olefin compound of formula 27 may be reacted with the oxime compound of formula 2 by methods previously described, to give the isoxazoline compound of formula 28. The double bond compound of formula 28 may be hydrogenated with Pd/C at elevated hydrogen pressure in solvents like methanol to give the reduced phenol compound of formula 29. The phenol compound 29 may be reacted with an appropriately substituted terminal group Za-CH$_2$X, where X is Cl, Br, or mesylate (e.g., 2-methyl-4-chloromethyl quinoline), in acetonitrile with potassium carbonate at reflux or DMSO with cesium carbonate to give compounds of formula 30. The ester of compound formula 30 may be converted to the hydroxamic acid in a solution of KOH/MeOH/NH$_2$OH or NaOMe/MeOH/NH$_2$OH at an appropriate temperature to give the compound of formula 24.

Scheme 5

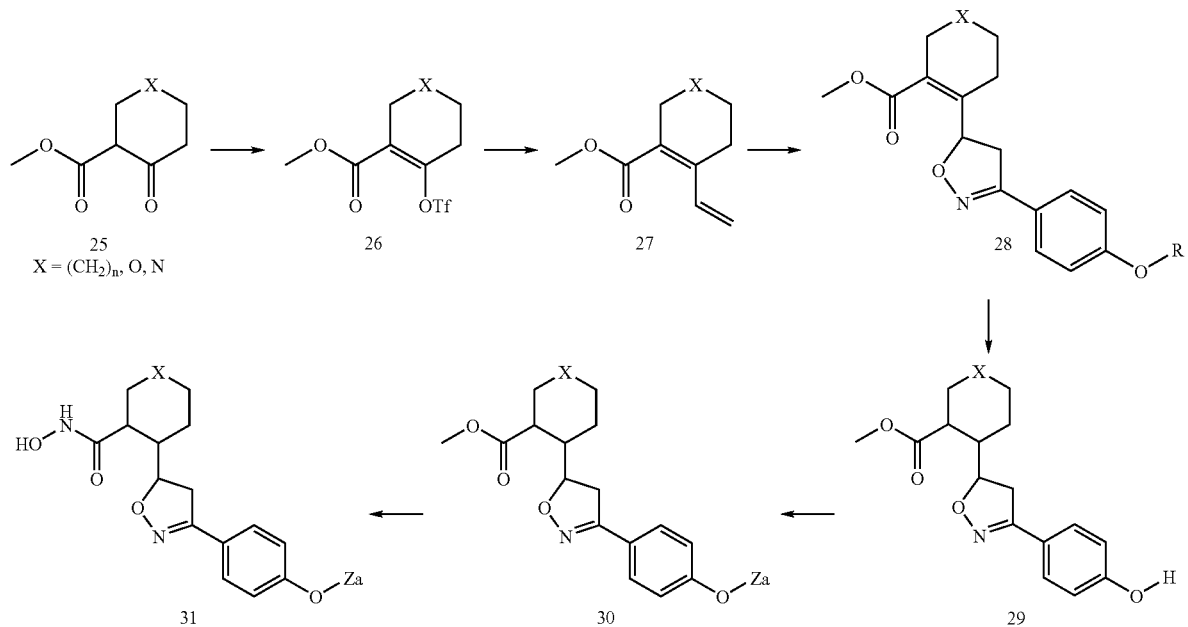

The compounds of formula 38 can be prepared as outlined in Scheme 6. The compound of formula 32 can be mono-protected with a variety of alcohol protecting groups well known in the literature, such as t-butyldimethyl silyl (TBS) in THF with sodium hydride, to give the compound of formula 33. The olefin compound of formula 33 can be reacted with the oxime compound of formula 2 by methods previously described, to give a mixture of hydroxymethylene isoxazoline compounds of formula 34 and aldehyde isoxazoline compounds of formula 35. The hydroxymethylene isoxazoline compounds of formula 34 can be converted to the aldehyde isoxazoline compounds of formula 35, by a variety of methods known in the literature for the oxidation of alcohols to aldehydes, for example, the Dess-Martin Periodinane or chrominium trioxide in an appropriate solvent (e.g., methylene chloride). The crotonate compound of formula 36 may be prepared from the aldehyde compound of formula 35 by methods well known in the literature, such as methyl(triphenylphosphoranylidene)acetate or trimethyl phosphonoacetate with a base (e.g., sodium hydride) in solvents like DMF or THF. The double bond compound of formula 36 may be hydrogenated with Rh/C at elevated hydrogen pressure in a solvent (e.g., methanol) to give the saturated compound of formula 37. The ester of compound formula 37 may be converted to the corresponding hydroxamic acid in a solution of KOH/MeOH/NH$_2$OH or NaOMe/MeOH/NH$_2$OH at an appropriate temperature to give the compound of formula 38; when Pg is the TBS group it is also removed by this process to give the corresponding hydroxymethylene.

Scheme 6

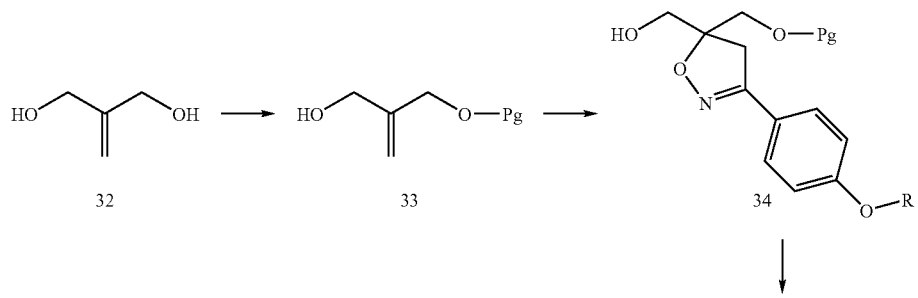

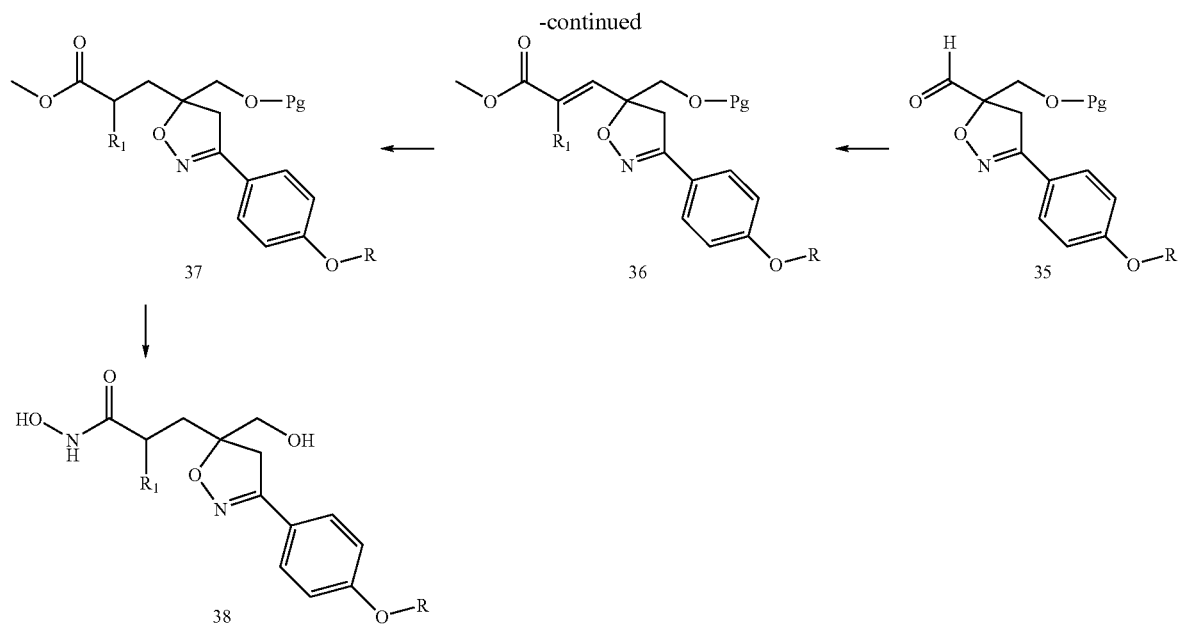

Alternatively, compounds of formula 36 may be reacted with a variety of nucleophiles well known in the literature for Michael-like additions to give compounds of formula 39. Wherein the Nu is an amine, it may be further reacted with acid chlorides, activated ester well known in the peptide literature, or isocyantes. Alternatively, the amine can be reacted with aldehydes under reductive conditions (e.g., sodium triacetoxyborohydride and benzaldehyde) in a solvent (e.g., 1,2-dichloroethane) as previously described. The ester of compound formula 39 can be converted to the hydroxamic acid in a solution of KOH/MeOH/NH$_2$OH or NaOMe/MeOH/NH$_2$OH at an appropriate temperature to give the compound of formula 41. When Pg is a TBS group, is will also be removed by this process to give the hydroxymethylene.

Scheme 7

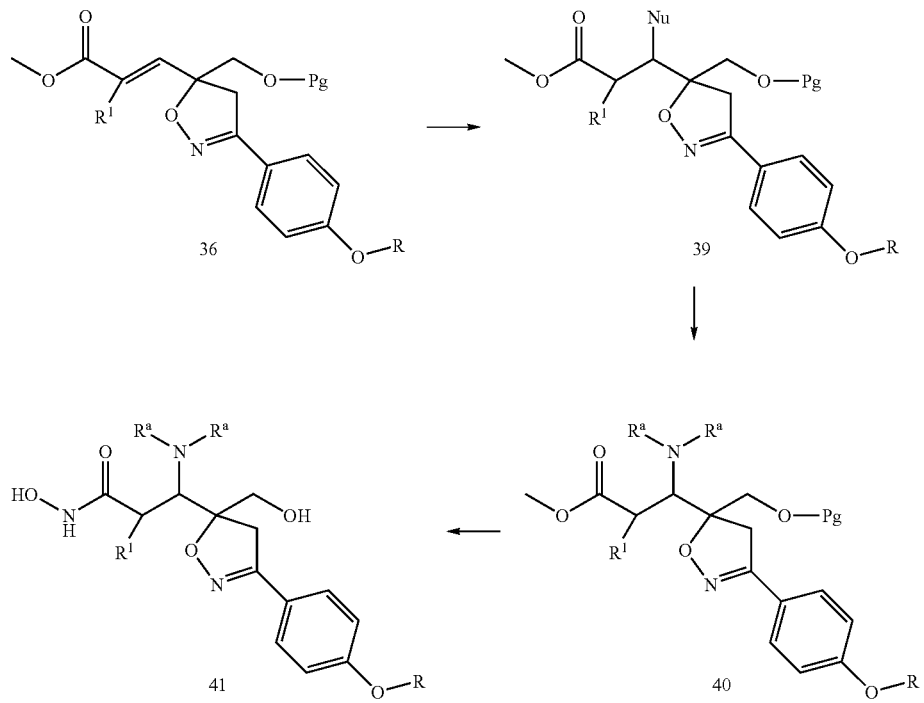

Alternatively, the protected hydroxymethylene group of formula 37 may be removed with known conditions appropriate for the protecting group used (e.g., when PG is TBS, tetrabutylammonium floride in THF) to give compounds of formula 42. The hydroxymethylene isoxazoline compounds of formula 42 can be converted to the aldehyde isoxazoline compounds of formula 43, by a variety of methods known in the literature for the oxidation of alcohols to aldehydes, for example, Dess-Martin Periodinane or chrominium trioxide in an appropriate solvent (e.g., methylene chloride). The aldehyde isoxazoline compounds of formula 43 may be reacted with a variety of amines (e.g., morpholine, methyl amine, or ammonia) to give the intermediate imine which can be reduced with a reagent such as sodium triacetoxyborohydride in an appropriate solvent (e.g., methylene chloride) to give the amino methylene compound of formula 44. The ester of compound formula 39 may be converted to the hydroxamic acid in a solution of KOH/MeOH/NH$_2$OH or NaOMe/MeOH/NH$_2$OH at an appropriate temperature to give the compound of formula 45.

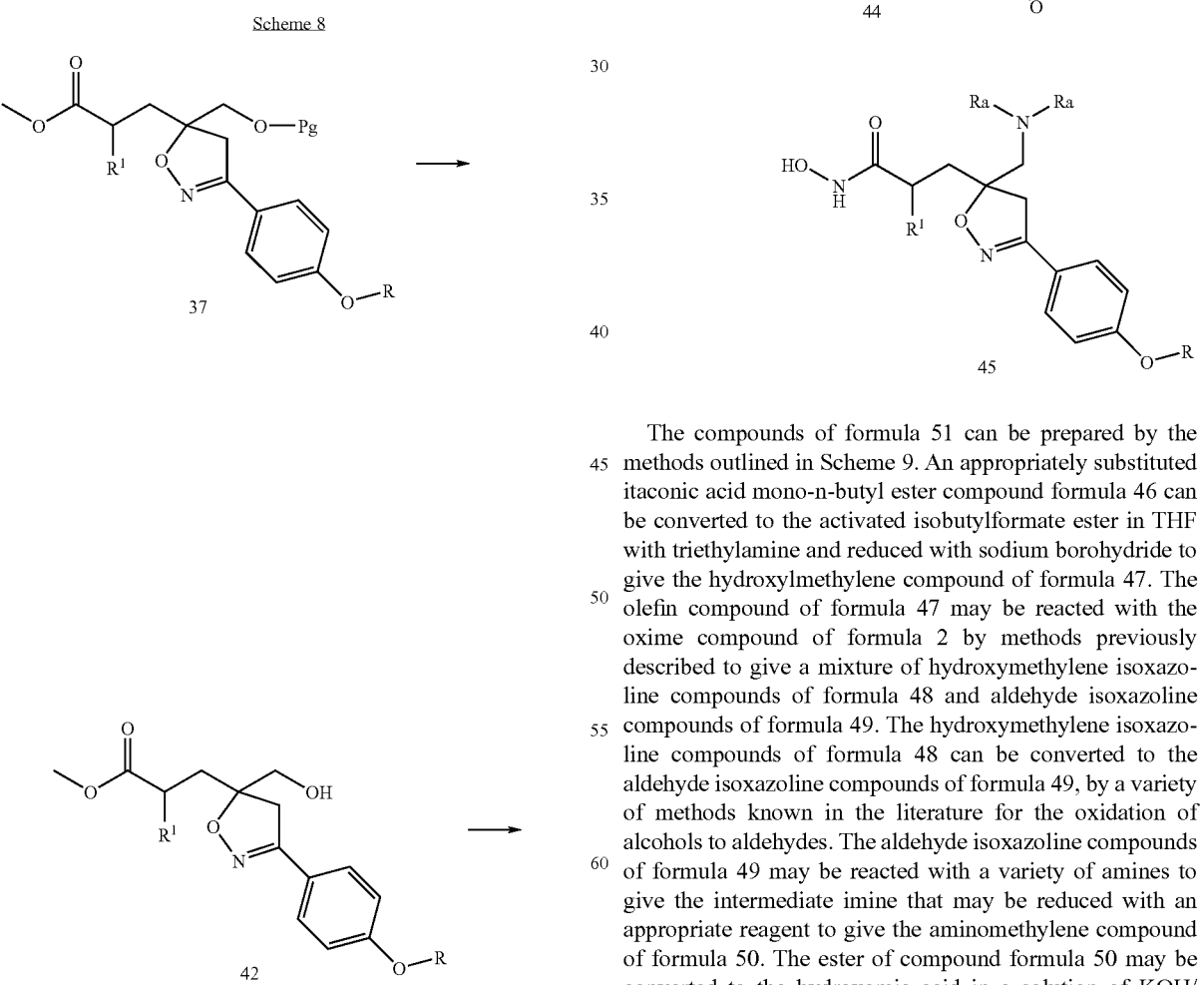

The compounds of formula 51 can be prepared by the methods outlined in Scheme 9. An appropriately substituted itaconic acid mono-n-butyl ester compound formula 46 can be converted to the activated isobutylformate ester in THF with triethylamine and reduced with sodium borohydride to give the hydroxylmethylene compound of formula 47. The olefin compound of formula 47 may be reacted with the oxime compound of formula 2 by methods previously described to give a mixture of hydroxymethylene isoxazoline compounds of formula 48 and aldehyde isoxazoline compounds of formula 49. The hydroxymethylene isoxazoline compounds of formula 48 can be converted to the aldehyde isoxazoline compounds of formula 49, by a variety of methods known in the literature for the oxidation of alcohols to aldehydes. The aldehyde isoxazoline compounds of formula 49 may be reacted with a variety of amines to give the intermediate imine that may be reduced with an appropriate reagent to give the aminomethylene compound of formula 50. The ester of compound formula 50 may be converted to the hydroxamic acid in a solution of KOH/MeOH/NH$_2$OH or NaOMe/MeOH/NH$_2$OH at an appropriate temperature to give the compound of formula 51.

Scheme 9
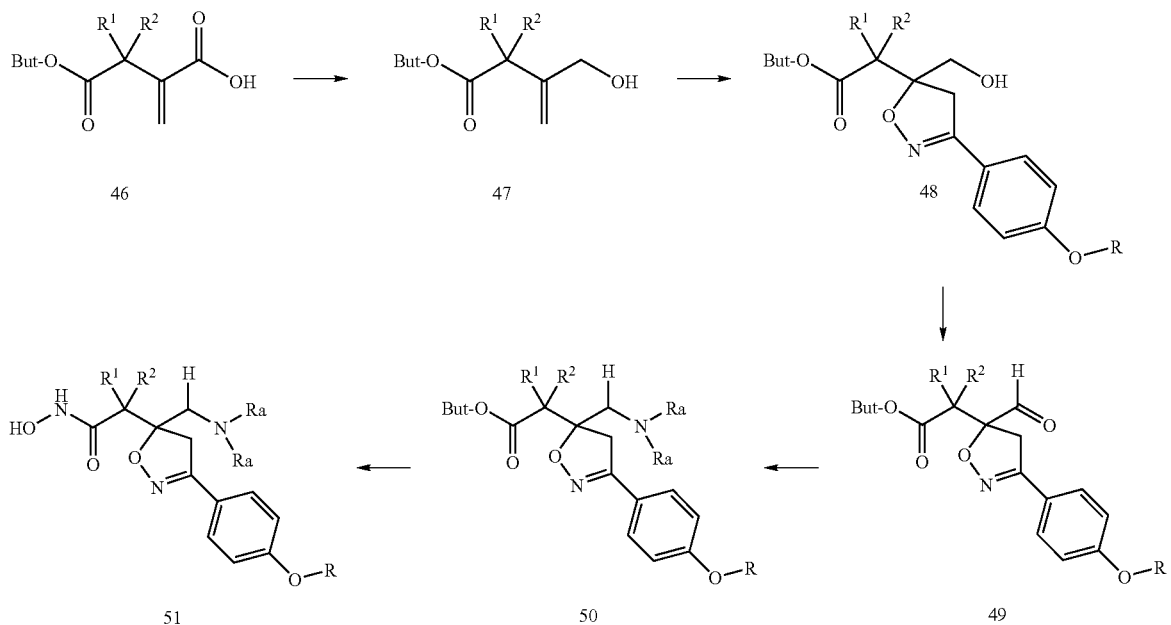
One stereoisomer of a compound of Formula I may display superior activity compared with the others. Thus, the following stereochemistries are considered to be a part of the present invention.
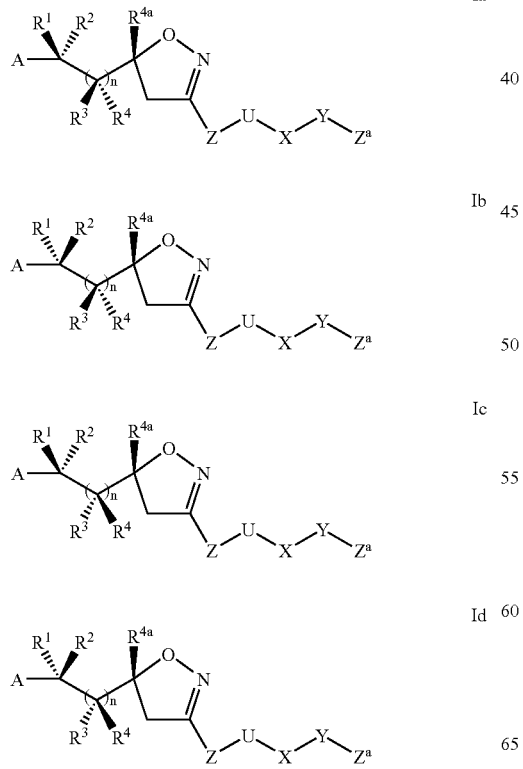
-continued
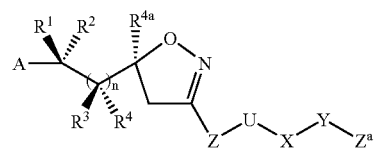
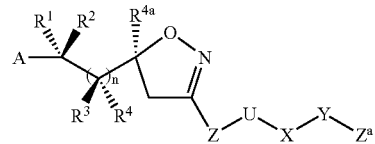
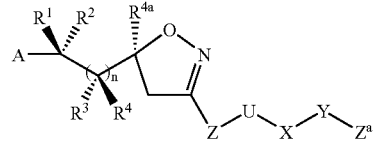
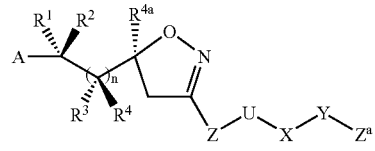
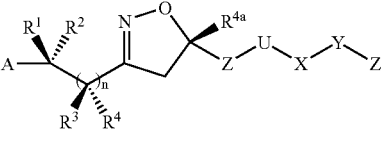

-continued

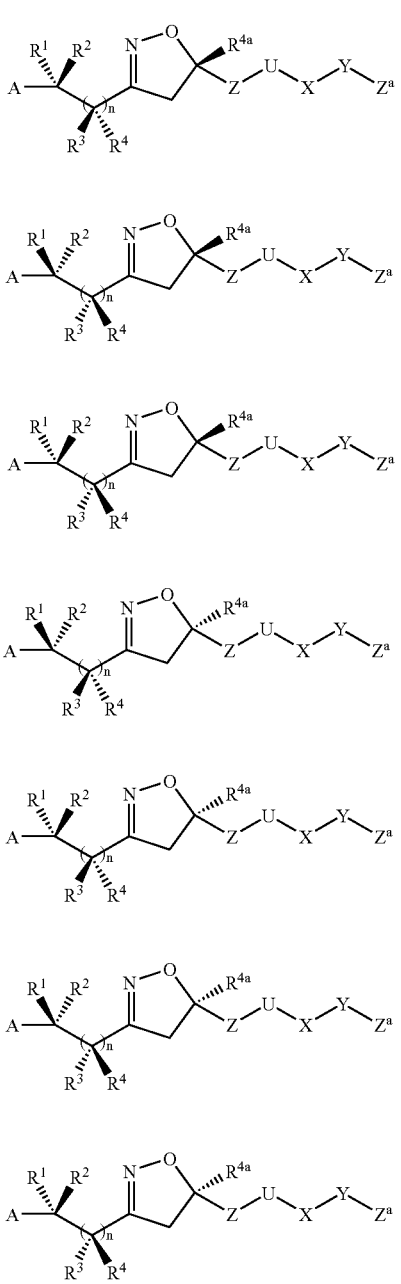

When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula I may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

Example 1

N-Hydroxy-2-{3-[4-(2-methyl-quinolin-4-yl-methoxy)-phenyl]-4,5-dihydro-isoxazol-5-yl}-acetamide 1a)

p-Hydroxybenzaldehyde (3.18 g, 26.1 mmol), 4-chloromethyl-2-methyl-quinoline (5.0 g, 26.1 mmol), and potassium carbonate (7.2 g, 52 mmol) were combined in acetonitrile (100 mL) and heated to reflux overnight. The reaction was allowed to cool to room temperature, diluted with ethyl acetate, filtered to remove the solids, and concentrated to give a semi-solid residue. The crude product was crystallized from ethyl ether to give 4-(2-methyl-quinolin-4-yl-methoxy)-benzaldehyde (6.5 g, 90%) as an off white precipitate. MS found: $(M+H)^+=278$.

1b)

A solution of sodium methoxide/hydroxylamine hydrochloride/methanol (~1.4 M)(10.4 mL) was added to 4-(2-methyl-quinolin-4-ylmethoxy)-benzaldehyde (2.0 g, 7.2 mmol) in methanol (20 mL) under a nitrogen atmosphere at room temperature. The reaction was stirred for 3 h and concentrated in vacuo to give a solid. This was triturated with water saturated $KH_2PO_4$ solution and water and dried in vacuo to give 4-(2-methyl-quinolin-4-ylmethoxy)-benzaldehyde oxime (1.75 g, 83%) as an off white solid. MS found: $(M+H)^+=293$.

1c)

A solution of Clorox® was added dropwise (1 mL) to a solution of vinyl acetic acid (0.071 g, 0.8 mmol) and 4-(2-methyl-quinolin-4-ylmethoxy)-benzaldehyde oxime (0.12 g, 0.40 mmol) in THF (4 mL) under nitrogen atmosphere at room temperature. The reaction was stirred overnight, partitioned between ethyl acetate and water saturated $KH_2PO_4$ solution. The organic layer was washed with brine, dried over magnesium sulfate and concentrated to give {3-[4-(2-methyl-quinolin-4-ylmethoxy)-phenyl]-4,5-dihydro-isoxazol-5-yl}-acetic acid (0.15 g, 100%) as a crude solid. MS found: $(M+H)^+=377$.

1d)

The {3-[4-(2-methyl-quinolin-4-ylmethoxy)-phenyl]-4,5-dihydro-isoxazol-5-yl}-acetic acid (0.15 g, 0.4 mmol) was combined with BOP (0.265 g, 0.6 mmol) and diisopropylethylamine (0.5 mL) in DMF (5 mL) under nitrogen atmosphere at room temperature. The reaction was stirred for 15 minutes, and then hydroxylamine hydrochloride (0.042 g, 0.6 mmol) was added. The reaction was stirred overnight, concentrated in vacuo, and triturated with water saturated $KH_2PO_4$ solution to give a precipitate. The crude product was purified by HPLC on a C-18 column eluting with an acetonitrile/water/TFA gradient to give the title compound (0.05 g, 25%) as an amorphous solid. MS found: $(M+H)^+=392$.

Example 2

N-Hydroxy-2-{3-[4-(2-methyl-quinolin-4-yl-methoxy)-phenyl]-4,5-dihydro-isoxazol-5-yl}-propionamide 2a)

Following a procedure analogous to that used in Example step 1c, but using 2-methyl-but-3-enoic acid methyl ester and 4-(2-methyl-quinolin-4-ylmethoxy)-benzaldehyde oxime from step 1b, the crude product was prepared. The crude product was purified by FCC (flash column chromatography) on silica gel to give 2-{3-[4-(2-methyl-quinolin-4-ylmethoxy)-phenyl]-4,5-dihydro-isoxazol-5-yl}-propionic acid methyl ester (0.13 g, 55%) as a solid residue. MS found: $(M+H)^+=405$.

2b)

The product from 2a (0.13 g, 0.32 mmol) was added to a solution of potassium hydroxide/hydroxylamine hydrochloride/methanol (~1.7 M) (3 mL) under nitrogen atmosphere at room temperature. The reaction was stirred for 1 h, neutralized with TFA, and concentrated in vacuo to give the crude product. The crude product was purified by HPLC on a C-18 column eluting with an acetonitrile:water:TFA gradient to give the title compound (0.075 g, 57%) as an amorphous solid. MS found: $(M+H)^+=406$.

Example 3

N-Hydroxy-2-{3-[4-(2-methyl-quinolin-4-yl-methoxy)-phenyl]-5-morpholin-4-ylmethyl-4,5-dihydro-isoxazol-5-yl}-acetamide 3a)

iso-Butylchloroformate (6.83 g, 50.0 mmol) was added to a solution of itaconic acid mono-n-butyl ester (9.31 g, 50.0 mmol) and triethylamine (5.06 g, 50.0 mmol) in THF (40 mL) under a nitrogen atmosphere and cooled to 0° C. The reaction was stirred for 0.5 h, filtered to remove the solids, added to a solution of sodium borohydride (3.78 g, 100.0 mmol) in water (20 mL), and cooled to 10° C. The reaction was stirred for 2 h, made acidic with 3 N HCl and extracted with ethyl ether (3×). The combined organic layers were washed with brine, dried over magnesium sulfate, and concentrated to give an oil. The product was purified by FCC on silica gel, eluting ethyl acetate:hexanes (1:2) to give 3-hydroxymethyl-but-3-enoic acid butyl ester (2.56 g, 30%) as an oil. MS found: $(M+H)^+=173$.

3b)

Following a procedure analogous to that used in step 1c, but using 3-hydroxymethyl-but-3-enoic acid butyl ester from step 3a and 4-(2-methyl-quinolin-4-ylmethoxy)-benzaldehyde oxime from step 1b, the crude product was prepared. The product was purified by FCC on silica gel to give {5-formyl-3-[4-(2-methyl-quinolin-4-ylmethoxy)-phenyl]-4,5-dihydro-isoxazol-5-yl}-acetic acid butyl ester (0.13 g, 36%) as an oil. MS found: $(M+H)^+=461$.

3c)

Sodium triacetoxyborohydride (0.084 g, 0.4 mmol) was added to a solution of the product from 3b (0.13 g, 0.28 mmol), morpholine (0.18 g, 2.8 mmol), and THF (5 mL) at room temperature. The reaction was stirred for 3 days and partitioned between ethyl acetate and water. The combined organic layers were washed with brine, dried over magnesium sulfate, and concentrated to give an oil. The product was purified by FCC on silica gel to give {3-[4-(2-methyl-quinolin-4-ylmethoxy)-phenyl]-5-morpholin-4-ylmethyl-4,5-dihydro-isoxazol-5-yl}-acetic acid butyl ester (0.054 g, 36%) as an oil. MS found: $(M+H)^+=532$.

3d)

The product from 3c (0.054 g, 0.10 mmol) was added to a solution of potassium hydroxide/hydroxylamine hydrochloride/methanol (~1.7 M)(3 mL) under a nitrogen atmosphere at room temperature. The reaction was stirred for 1 h, neutralized with TFA, and concentrated in vacuo to give the crude product. The crude product was purified by HPLC on a C-18 column eluting with an acetonitrile:water:TFA gradient to give the title compound (0.022 g, 44%) as an amorphous solid. MS found: $(M+H)^+=491$.

Example 4

N-Hydroxy-2-{3-[4-(2-methyl-quinolin-4-yl-methoxy)-phenyl]-5-piperazin-1-ylmethyl-4,5-dihydro-isoxazol-5-yl}-acetamide 4a)

Following a procedure analogous to that used in Example 3, but using piperazine-1-carboxylic acid tert-butyl ester, the crude product was prepared. The product was purified by FCC on silica gel to give 4-{5-hydroxycarbamoylmethyl-3-[4-(2-methyl-quinolin-4-ylmethoxy)-phenyl]-4,5-dihydro-isoxazol-5-ylmethyl}-piperazine-1-carboxylic acid tert-butyl ester (0.0086 g, 40%) as a residue.

4b)

The product from 4a (0.0086 g, 0.015 mmol) was dissolved in methylene chloride (1 mL) and TFA (1 mL) at room temperature, stirred for 1 h, concentrated in vacuo to give the crude product. The crude product was purified by HPLC on a C-18 column eluting with an acetonitrile:water:TFA gradient to give the title compound (0.006 g, 80%) as an amorphous solid. MS found: $(M+H)^+=490$.

Example 5

2-{5-Dimethylaminomethyl-3-[4-(2-methyl-quinolin-4-ylmethoxy)-phenyl]-4,5-dihydro-isoxazol-5-yl}-N-hydroxy-acetamide Following a procedure analogous to that used in Example 3, but using dimethylamine, the crude product was prepared. The crude product was purified by HPLC on a C-18 column eluting with an acetonitrile:water:TFA gradient to give the title compound (0.005 g, 37%) as an amorphous solid. MS found: $(M+H)^+=449$.

Example 6

N-Hydroxy-3-{3-[4-(2-methyl-quinolin-4-yl-methoxy)-phenyl]-4,5-dihydro-isoxazol-5-yl}-propionamide Following a procedure analogous to that used in Example 1, but using pent-4-enoic acid and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.03 g, 21%). MS found: $(M+H)^+=406$.

Example 7

N-Hydroxy-3-methyl-3-{3-[4-(2-methyl-quinolin-4-ylmethoxy)-phenyl]-4,5-dihydro-isoxazol-5-yl}-butyramide 7a)

Following a procedure analogous to that used in Example step 1c, but using 3,3-dimethyl-pent-4-enoic acid methyl ester and 4-(2-methyl-quinolin-4-ylmethoxy)-benzaldehyde oxime from step 1b, the crude reaction was partitioned between ethyl acetate and water and the organic layer was washed with brine, dried over magnesium sulfate, and concentrated to give 3-methyl-3-{3-[4-(2-methyl-quinolin-4-ylmethoxy)-phenyl]-4,5-dihydro-isoxazol-5-yl}-butyric acid methyl ester (0.14 g, 100%) as a crude oil. MS found: $(M+H)^+=433$.

7b)

The product from 7a (0.14 g, 0.34 mmol) was added to a solution of sodium methoxide/hydroxylamine hydrochloride/methanol (~1.4 M) (3 mL) under a nitrogen atmosphere at room temperature. The reaction was stirred for 1 h, neutralized with TFA, and concentrated in vacuo to give the crude product. The crude product was purified by HPLC on a C-18 column eluting with an acetonitrile:water:TFA gradient to give the title compound (0.065 g, 44%) as an amorphous solid. MS found: $(M+H)^+=434$.

Example 8

(1-Hydroxycarbamoyl-2-{3-[4-(2-methyl-quinolin-4-ylmethoxy)-phenyl]-4,5-dihydro-isoxazol-5-yl}-ethyl)-carbamic acid tert-butyl ester 8a)

HCl (g) was bubbled through a solution of DL-allylglycine (2.0 g, 17.4 mmol) in methanol (50 mL) at room temperature. The reaction was stirred overnight, concentrated in vacuo, taken up in acetonitrile (50 mL), and re-concentrated to give 2-amino-pent-4-enoic acid methyl ester hydrochloride salt (2.8 g, 100%) as an oil. MS found: $(M+CH_3CN)^+=171$.

8b)

The product from 8a (2.8 g, 17.4 mmol) was combined with triethylamine (10 mL) and di-tert-butyl dicarbonate (4.7 g, 22 mmol) in methylene chloride (70 mL) under a nitrogen atmosphere at room temperature. The reaction was stirred for 4.5 h and partitioned between methylene chloride and water. The organic layer was washed with water, 1 N HCl (2×), brine, dried over magnesium sulfate, and concentrated to give an oil. The product was purified by FCC on silica gel eluting ethyl ether:hexane (5:95) to give 2-tert-butoxycarbonylamino-pent-4-enoic acid methyl ester (4.5 g, 51%) as an oil. MS found: $(M+H)^+=230$.

8c)

Following a procedure analogous to that used in Example step 1c, but using the product from step 8b and 4-(2-methyl-quinolin-4-ylmethoxy)-benzaldehyde oxime from step 1b, the crude product was prepared and purified by FCC on silica gel eluting ethyl acetate:hexanes (gradient) to give 2-tert-butoxycarbonylamino-3-{3-[4-(2-methyl-quinolin-4-ylmethoxy)-phenyl]-4,5-dihydro-isoxazol-5-yl}-propionic acid methyl ester (1.15 g, 65%) as an oil. MS found: $(M+H)^+=520$.

8d)

Following a procedure analogous to that used in Example step 7b, but using the product from step 8c, the crude product was prepared. The product was purified by HPLC on a C-18 column eluting with an acetonitrile:water:TFA gradient to give the title compound (0.065 g, 69%) as an amorphous solid. MS found: $(M+H)^+=521$.

Example 9

2-Amino-N-hydroxy-3-{3-[4-(2-methyl-quinolin-4-ylmethoxy)-phenyl]-4,5-dihydro-isoxazol-5-yl}-propionamide 9a)

Trifluoroacetic acid (1 mL) was added to a solution of 2-tert-butoxycarbonylamino-3-{3-[4-(2-methyl-quinolin-4-ylmethoxy)-phenyl]-4,5-dihydro-isoxazol-5-yl}-propionic acid methyl ester from Example step 8c in methylene chloride at room temperature. After stirring for 1 h, the reaction was concentrated in vacuo to give 2-amino-3-{3-[4-(2-methyl-quinolin-4-ylmethoxy)-phenyl]-4,5-dihydro-isoxazol-5-yl}-propionic acid methyl ester trifluoroacetate salt (0.1 g, 100%) as an oil. MS found: $(M+H)^+=420$.

9b)

Following a procedure analogous to that used in Example step 7b, but using the product from step 9a, the crude product was prepared. The product was purified by HPLC on a C-18 column eluting with an acetonitrile:water:TFA gradient to give the title compound (0.085 g, 68%) as an amorphous solid. MS found: $(M+H)^+=421$.

Example 10

3-Amino-N-hydroxy-3-{3-[4-(2-methyl-quinolin-4-ylmethoxy)-phenyl]-4,5-dihydro-isoxazol-5-yl}-propionamide 10a)

Following a procedure analogous to that used in Example step 1c, but using 3,3-dimethoxy-propene and 4-(2-methyl-quinolin-4-ylmethoxy)-benzaldehyde oxime from step 1b, the crude reaction was partitioned between ethyl acetate and water and the organic layer was washed with brine, dried over magnesium sulfate, and concentrated to give 4-[4-(5-dimethoxymethyl-4,5-dihydro-isoxazol-3-yl)-phenoxymethyl]-2-methyl-quinoline (0.4 g, 100%) as a crude oil. MS found: $(M+H)^+=393$.

10b)

The product from step 10a (0.4 g, 1.0 mmol) was dissolved in THF (5 mL) and 6 N HCl (5 mL) and heated to 60° C. for 2.5 h. The reaction was cooled and concentrated, and the aqueous layer was neutralized with NaOH and then extracted with ethyl acetate. The organic layer was washed with brine, dried over magnesium sulfate, and concentrated to give an oil. The oil was purified with FCC eluting ethyl acetate:methylene chloride (80:20) to give 3-[4-(2-methyl-quinolin-4-ylmethoxy)-phenyl]-4,5-dihydro-isoxazole-5-carbaldehyde (0.1 g, 72%) as an oil. MS found: $(M+H)^+=347$.

10c)

t-Butyl dimethylphosphonoacetate (0.31 g, 1.38 mmol) was added to a suspension of sodium hydride (washed with hexanes) (0.061 g @60%, 1.5 mmol) in DMF (3 mL) cooled in an ice bath, under a nitrogen atmosphere. The reaction was stirred for 0.5 h and the product from step 10b (0.31 g, 1.38 mmol) in DMF (3 mL) was added. The reaction was stirred for 2 h at 0° C. and was complete. This was partitioned between ethyl acetate and water. The organic layer was washed with brine, dried over magnesium sulfate, and concentrated to give an oil. The product was purified by FCC on silica gel eluting methylene chloride:ethyl acetate (70:30) to give 3-{3-[4-(2-methyl-quinolin-4-ylmethoxy)- phenyl]-4,5-dihydro-isoxazol-5-yl}-acrylic acid tert-butyl ester (0.38 g, 61%) as an oil. MS found: $(M+H)^+=445$.

10d)

The product from step 10c (0.3 g, 0.67 mmol) was dissolved in methanol (10 mL) and condensed ammonia (10 mL) in a stainless steel pressure reactor and heated to 60° C. for 5 h. The reaction was complete and was concentrated to give 3-amino-3-{3-[4-(2-methyl-quinolin-4-ylmethoxy)-phenyl]-4,5-dihydro-isoxazol-5-yl}-propionic acid tert-butyl ester (0.3 g, 97%) as an oil. MS found: $(M+H)^+=462$.

10e)

HCl (g) was bubbled through a solution of the product from step 10d (0.3 g, 0.65 mmol) in methanol (20 mL) at room temperature for 5 minutes and the reaction was stirred for 3 h. This was complete, concentrated in vacuo to give a solid which was triturated into a powder with ethyl ether to give 3-amino-3-{3-[4-(2-methyl-quinolin-4-ylmethoxy)-phenyl]-4,5-dihydro-isoxazol-5-yl}-propionic acid methyl ester di-hydrochloride salt (0.21 g, 64%) as a off white solid. MS found: $(M+H)^+=420$.

10f)

Following a procedure analogous to that used in Example step 7b, but using the product from step 10e, the crude product was prepared. The product was purified by HPLC on a C-18 column eluting with an acetonitrile:water:TFA gradient to give the title compound (0.030 g, 31%) as an amorphous solid. MS found: $(M+H)^+=421$.

Example 11

N-Hydroxy-3-{3-[4-(2-methyl-quinolin-4-yl-methoxy)-phenyl]-4,5-dihydro-isoxazol-5-yl}-3-methylsulfanyl-propionamide 11a)

Following a procedure analogous to that used in Example step 1c, but using penta-2,4-dienoic acid methyl ester and 4-(2-methyl-quinolin-4-ylmethoxy)-benzaldehyde oxime from step 1b, the crude reaction was partitioned between ethyl acetate and water, and the organic layer was washed with brine, dried over magnesium sulfate, and concentrated to give 3-{3-[4-(2-methyl-quinolin-4-ylmethoxy)-phenyl]-4,5-dihydro-isoxazol-5-yl}-acrylic acid methyl ester (2.57 g, 73%) as a white powder. MS found: $(M+H)^+=403$.

11b)

A suspension of the product from step 11a (1.0 g, 2.5 mmol), thioacetic acid (3.0 mL), and triethylamine (0.25 mL, 1.8 mmol) was stirred for 6 h at room temperature while slowly becoming a clear solution. The reaction was partitioned between ethyl acetate and water. The organic layer was washed with aqueous sodium bicarbonate (2×), brine, dried over magnesium sulfate, and concentrated to give the crude product. This was purified by FCC on silica gel eluting ethyl acetate:hexanes (gradient) to give 3-acetylsulfanyl-3-{3-[4-(2-methyl-quinolin-4-ylmethoxy)-phenyl]-4,5-dihydro-isoxazol-5-yl}-propionic acid methyl ester (0.74 g, 63%) as an oil. MS found: $(M+H)^+=479$.

11c)

Sodium methoxide (28% in methanol) (0.050 mL, 0.22 mmol) was added to a suspension of the product from step 11b (0.085 g, 0.18 mmol) in methanol (1.5 mL) at room temperature. The reaction turned clear and was stirred for 45 minutes, and then methyl iodide (0.05 mL, 0.80 mmol) was added. The reaction was stirred an additional 45 minutes, quenched with aqueous ammonium chloride, concentrated to remove the methanol, and partitioned between ethyl acetate and water. The organic layer was washed with brine, dried with magnesium sulfate, and concentrated to give 3-{3-[4-(2-methyl-quinolin-4-ylmethoxy)-phenyl]-4,5-dihydro-isoxazol-5-yl}-3-methylsulfanyl-propionic acid methyl ester (0.08 g, 99%) as an oil. MS found: $(M+H)^+=451$.

11d)

Following a procedure analogous to that used in Example step 7b, but using the product from step 11c, the crude product was prepared. The product was purified by HPLC on a C-18 column eluting with an acetonitrile:water:TFA gradient to give the title compound (0.038 g, 40%) as an amorphous solid. MS found: $(M+H)^+=452$.

Example 12

N-Hydroxy-3-{3-[4-(2-methyl-quinolin-4-yl-methoxy)-phenyl]-4,5-dihydro-isoxazol-5-yl}-3-morpholin-4-yl-propionamide Following a procedure analogous to that used in Example 10, but using morpholine and acetonitrile in step 10d, the crude product was prepared. The product was purified by HPLC on a C-18 column eluting with an acetonitrile:water:TFA gradient to give the title compound (0.055 g, 66%) as an amorphous solid. MS found: $(M+H)^+=491$.

Example 13

3-Amino-N-hydroxy-3-{3-[4-(2-methyl-quinolin-4-ylmethoxy)-phenyl]-4,5-dihydro-isoxazol-5-yl}-butyramide 13a)

Following a procedure analogous to that used in Example step 1c, but using 3-methyl-penta-2,4-dienoic acid ethyl ester and 4-(2-methyl-quinolin-4-ylmethoxy)-benzaldehyde oxime from step 1b, the crude reaction was partitioned between ethyl acetate and water, and the organic layer was washed with brine, dried over magnesium sulfate, and concentrated to give an oil. The product was purified by FCC on silica gel eluting ethyl acetate:hexane (gradient) to give 3-{3-[4-(2-methyl-quinolin-4-ylmethoxy)-phenyl]-4,5-dihydro-isoxazol-5-yl}-but-2-enoic acid ethyl ester (0.93 g, 84%) as a mixture of diasteromers. MS found: $(M+H)^+=431$.

13b)

Following a procedure analogous to that used in Example step 10d, but using the product from step 13a, the 3-amino-3-{3-[4-(2-methyl-quinolin-4-ylmethoxy)-phenyl]-4,5-dihydro-isoxazol-5-yl}-butyric acid ethyl ester (0.89 g, 94%) was prepared as a glass. MS found: $(M+H)^+=448$.

13c)

Following a procedure analogous to that used in Example step 7b, but using the product from step 13b, the crude product was prepared. The product was purified by HPLC on a C-18 column eluting with an acetonitrile:water:TFA gradient to give the title compound (0.080 g, 62%) as an amorphous solid. MS found: $(M+H)^+=435$.

Example 14

Furan-2-carboxylic acid (2-hydroxycarbamoyl-1-{3-[4-(2-methyl-quinolin-4-ylmethoxy)-phenyl]-4,5-dihydro-isoxazol-5-yl}-ethyl)-amide 14a)
Furan-2-carbonyl chloride ((0.07 g, 0.54 mmol) was added to a mixture of 3-amino-3-{3-[4-(2-methyl-quinolin-4-ylmethoxy)-phenyl]-4,5-dihydro-isoxazol-5-yl}-propionic acid methyl ester di-hydrochloride salt (0.22 g, 0.45 mmol) from step 10e, methylene chloride (10 mL) and aqueous sodium carbonate (5 mL) under a nitrogen atmosphere at room temperature. The reaction was stirred vigorously for 2 h, and partitioned between ethyl acetate and water. The organic layer was washed with brine, dried over magnesium sulfate, and concentrated to give 3-[(furan-2-carbonyl)-amino]-3-{3-[4-(2-methyl-quinolin-4-ylmethoxy)-phenyl]-4,5-dihydro-isoxazol-5-yl}-propionic acid methyl ester (0.23 g, 100%) as an oil. MS found: $(M+H)^+=514$.

14b)
Following a procedure analogous to that used in Example step 7b, but using the product from step 14a, the crude product was prepared. The product was purified by HPLC on a C-18 column eluting with an acetonitrile:water:TFA gradient to give the title compound (0.14 g, 60%) as an amorphous solid. MS found: $(M+H)^+=515$.

Example 15

N-Hydroxy-3-{3-[4-(2-methyl-quinolin-4-ylmethoxy)-phenyl]-4,5-dihydro-isoxazol-5-yl}-3-pyrrolidin-1-yl-propionamide Following a procedure analogous to that used in Example 10, but using pyrrolidine in step 10d, the crude product was prepared. The product was purified by HPLC on a C-18 column eluting with an acetonitrile:water:TFA gradient to give the title compound (0.095 g, 62%) as an amorphous solid. MS found: $(M+H)^+=475$.

Example 16

3-Acetylamino-N-hydroxy-3-{3-[4-(2-methyl-quinolin-4-ylmethoxy)-phenyl]-4,5-dihydro-isoxazol-5-yl}-propionamide Following a procedure analogous to that used in Example 14, but using acetic anhydride in step 14a, the crude product was prepared. The product was purified by HPLC on a C-18 column eluting with an acetonitrile:water:TFA gradient to give the title compound (0.037 g, 26%) as an amorphous solid. MS found: $(M+H)^+=463$.

Example 17

3-Dimethylamino-N-hydroxy-3-{3-[4-(2-methyl-quinolin-4-ylmethoxy)-phenyl]-4,5-dihydro-isoxazol-5-yl}-propionamide 17a)
Formaldehyde (37% in water) (0.120 mL, 1.48 mmol) was added to a solution of 3-amino-3-{3-[4-(2-methyl-quinolin-4-ylmethoxy)-phenyl]-4,5-dihydro-isoxazol-5-yl}-propionic acid methyl ester di-hydrochloride salt (0.15 g, 0.30 mmol) from step 10e, 1,2-dichloroethane (2 mL), and diisopropylethylamine (0.20 mL) under a nitrogen atmosphere at room temperature. The reaction was stirred for 0.5 h and sodium triacetoxyborohydride (0.45 g, 2.1 mmol) was added. The reaction stirred an additional 2 h, quenched with water and extracted with methylene chloride (2×). The combined organic layers were washed with brine, dried over magnesium sulfate, and concentrated to give 3-dimethylamino-3-{3-[4-(2-methyl-quinolin-4-ylmethoxy)-phenyl]-4,5-dihydro-isoxazol-5-yl}-propionic acid methyl ester (0.125 g, 93%) as a crude oil. MS found: $(M+H)^+=448$.

17b)
Following a procedure analogous to that used in Example step 7b, but using the product from step 17a, the crude product was prepared. The product was purified by HPLC on a C-18 column eluting with an acetonitrile:water:TFA gradient to give the title compound (0.12 g, 58%) as an amorphous solid. MS found: $(M+H)^+=449$.

Example 18

3-(3-Ethyl-ureido)-N-hydroxy-3-{3-[4-(2-methyl-quinolin-4-ylmethoxy)-phenyl]-4,5-dihydro-isoxazol-5-yl}-propionamide Following a procedure analogous to that used in Example 14, but using ethyl isocyanate in step 14a, the crude product was prepared. The product was purified by HPLC on a C-18 column eluting with an acetonitrile:water:TFA gradient to give the title compound (0.040 g, 26%) as an amorphous solid. MS found: $(M+H)^+=492$.

Example 19

N-Hydroxy-3-methanesulfonylamino-3-{3-[4-(2-methyl-quinolin-4-ylmethoxy)-phenyl]-4,5-dihydro-isoxazol-5-yl}-propionamide Following a procedure analogous to that used in Example 14, but using methane sulfonyl chloride in step 14a, the crude product was prepared. The product was purified by HPLC on a C-18 column eluting with an acetonitrile:water:TFA gradient to give the title compound (0.063 g, 43%) as an amorphous solid. MS found: $(M+H)^+=499$.

Example 20

3-[(Furan-2-ylmethyl)-amino]-N-hydroxy-3-{3-[4-(2-methyl-quinolin-4-ylmethoxy)-phenyl]-4,5-dihydro-isoxazol-5-yl}-propionamide Following a procedure analogous to that used in Example 17, but using furan-2-carbaldehyde in step 17a, the crude product was prepared. The product was purified by HPLC on a C-18 column eluting with an acetonitrile:water:TFA gradient to give the title compound (0.055 g, 32%) as an amorphous solid. MS found: $(M+H)^+=501$.

Example 21

3-Benzylamino-N-hydroxy-3-{3-[4-(2-methyl-quinolin-4-ylmethoxy)-phenyl]-4,5-dihydro-isoxazol-5-yl}-propionamide Following a procedure analogous to that used in Example 17, but using benzaldehyde in step 17a, the crude product was prepared. The product was purified by HPLC on a C-18 column eluting with an acetonitrile:water:TFA gradient to give the title compound (0.05 g, 32%) as an amorphous solid. MS found: (M+H)$^+$=511.

Example 22

(2-Hydroxycarbamoyl-1-{3-[4-(2-methyl-quinolin-4-ylmethoxy)-phenyl]-4,5-dihydro-isoxazol-5-yl}-ethyl)-carbamic acid isobutyl ester Following a procedure analogous to that used in Example 14, but using isobutylchloroformate in step 14a, the crude product was prepared. The product was purified by HPLC on a C-18 column eluting with an acetonitrile:water:TFA gradient to give the title compound (0.023 g, 26%) as an amorphous solid. MS found: (M+H)$^+$=521.

Example 23

N-Hydroxy-3-{5-methyl-3-[4-(2-methyl-quinolin-4-ylmethoxy)-phenyl]-4,5-dihydro-isoxazol-5-yl}-propionamide Following a procedure analogous to that used in Example 7, but using 4-methyl-pent-4-enoic acid ethyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.3 g, 35%). MS found: (M+H)$^+$=420.

Example 24

N-Hydroxy-3-{5-hydroxymethyl-3-[4-(2-methyl-quinolin-4-ylmethoxy)-phenyl]-4,5-dihydro-isoxazol-5-yl}-propionamide 24a)

2-Methylene-propane-1,3-diol (3.0 g, 34.05 mmol) was added slowly to a suspension of sodium hydride (washed free of oil with hexanes) (1.36 g, 60% in oil, 34.05 mmol) in THF (50 mL) under a nitrogen atmosphere at room temperature. The reaction was stirred vigorously for 1 h to give a thick slurry. t-Butyldimethylsilyl chloride (5.13 g, 34.05 mmol) was added, and the reaction was stirred for 1 h and then partitioned between ethyl acetate and water saturated with sodium bicarbonate. The organic layer was washed with water and brine, dried over magnesium sulfate, and concentrated to give an oil. The product was purified by FCC on silica gel eluting hexane:ethyl acetate (80:20) to give 2-(tert-butyl-dimethyl-silanyloxymethyl)-prop-2-en-1-ol (3.2 g, 47%) as an oil. MS found: (M+H)$^+$=203.

24b)

A solution of Clorox® was added dropwise (1 mL) to a solution of the product from step 24a (0.52 g, 2.56 mmol) and 4-(2-methyl-quinolin-4-ylmethoxy)-benzaldehyde oxime (0.5 g, 1.71 mmol) from step 1b in THF (4 mL) under nitrogen atmosphere at room temperature. The reaction was stirred overnight, partitioned between ethyl acetate and water saturated with KH$_2$PO$_4$. The organic layer was washed with brine, dried over magnesium sulfate, and concentrated to give an oil. The product was purified by FCC on silica gel eluting methylene chloride:ethyl acetate (50:50) to give {5-(tert-butyl-dimethyl-silanyloxymethyl)-3-[4-(2-methyl-quinolin-4-ylmethoxy)-phenyl]-4,5-dihydro-isoxazol-5-yl}-methanol (0.51 g, 61%) as an oil. MS found: (M+H)$^+$=493.

24c)

Dess-Martin Periodinate reagent (0.47 g, 1.1 mmol) was added to a solution of the product from step 24b, in methylene chloride (10 mL) under a nitrogen atmosphere at room temperature. The reaction was stirred for 1 h and then partitioned between ethyl acetate and aqueous 10% NaHSO$_4$. The organic layer was washed with water and brine, dried over magnesium sulfate, and concentrated to give 5-(tert-butyl-dimethyl-silanyloxymethyl)-3-[4-(2-methyl-quinolin-4-ylmethoxy)-phenyl]-4,5-dihydro-isoxazole-5-carbaldehyde as a crude oil. MS found: (M+H)$^+$=491.

24d)

Trimethyl phosphonoacetate (0.4 g, 2.2 mmol) was added to a suspension of sodium hydride (hexane washed) (0.088 g, 60% in oil, 2.2 mmol) in DMF (7 mL) under a nitrogen atmosphere at 0° C. The reaction was stirred for 0.5 h and the aldehyde from step 24c was added. The reaction was stirred for 1 h and then partitioned between ethyl acetate and water. The organic layer was washed with brine, dried over magnesium sulfate, and concentrated to give an oil. The product was purified by FCC on silica gel eluting methylene chloride:ethyl acetate (60:50) to give 3-{5-(tert-butyl-dimethyl-silanyloxymethyl)-3-[4-(2-methyl-quinolin-4-ylmethoxy)-phenyl]-4,5-dihydro-isoxazol-5-yl}-acrylic acid methyl ester (0.24 g, 20%) as an oil. MS found: (M+H)$^+$=547.

24e)

The product from step 24d (0.24 g, 0.44 mmol) was dissolved in methanol (15 mL), degassed by bubbling nitrogen through the solution, charged with Rh/C and hydrogen gas (40 PSI), and shaken for 2 h. The reaction was filtered and concentrated to give 3-{5-(tert-butyl-dimethyl-silanyloxymethyl)-3-[4-(2-methyl-quinolin-4-ylmethoxy)-phenyl]-4,5-dihydro-isoxazol-5-yl}-propionic acid methyl ester as a crude oil. MS found: (M+H)$^+$=549.

24f)

Following a procedure analogous to that used in Example step 7b, but using the product from step 24e, the crude product was prepared. The product was purified by HPLC on a C-18 column eluting with an acetonitrile:water:TFA gradient to give the title compound (0.080 g, 42%) as an amorphous solid. MS found: (M+H)$^+$=436.

Example 25

5-(2-Hydroxycarbamoyl-ethyl)-3-[4-(2-methyl-quinolin-4-ylmethoxy)-phenyl]-4,5-dihydro-isoxazole-5-carboxylic acid methyl ester Following a procedure analogous to that used in Example 7, but using 2-methylene-pentanedioic acid dimethyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.035 g, 75%). MS found: (M+H)$^+$=464.

Example 26

5-(2-Hydroxycarbamoyl-ethyl)-3-[4-(2-methyl-quinolin-4-ylmethoxy)-phenyl]-4,5-dihydro-isoxazole-5-carboxylic acid hydroxyamide Following a procedure analogous to that used in Example step 7b, but using 5-(2-methoxycarbonyl-ethyl)-3-[4-(2-methyl-quinolin-4-ylmethoxy)-phenyl]-4,5-dihydro-isoxazole-5-carboxylic acid methyl ester from Example 25, the title compound was prepared and purified by HPLC on a C-18 column eluting with an acetonitrile:water:TFA gradient to give an amorphous solid (0.011 g, 36%). MS found: $(M+H)^+= 465$.

Example 27

2-{3-[4-(2-Methyl-quinolin-4-ylmethoxy)-phenyl]-4,5-dihydro-isoxazol-5-yl}-cyclopent-1-enecarboxylic acid hydroxyamide 27a)
Trifluoromethanesulfonic anhydride (1.5 mL, 8.9 mmol) was slowly added to a solution of methyl 2-oxocyclopentanecarboxylate (1.0 mL, 8.1 mmol) and N,N-diisopropylethylamine (2.2 mL, 13.0 mmol) in methylene chloride (30 mL) under a nitrogen atmosphere at room temperature. The reaction was stirred for 72 h, and then partitioned between methylene chloride and water. The organic layer was washed with 1 N HCl, aqueous $NaHCO_3$, and brine; dried over magnesium sulfate; and concentrated to give an oil. The product was purified by FCC on silica gel eluting ethyl ether:hexane (5:95) to give 2-trifluoromethanesulfonyloxy-cyclopent-1-enecarboxylic acid methyl ester (1.62 g, 73%) as a yellow oil.

27b)
Palladium (II) acetate (0.095 g) was added to a solution of the product from step 27a (1.62 g, 5.9 mmol), tributyl(vinyl) tin (1.72 mL, 5.9 mmol), and triphenylphosphine (0.215 g, 0.82 mmol) in THF (20 mL) under a nitrogen atmosphere. The reaction was heated to 50° C. for 3 h, cooled to room temperature and concentrated. The residue was purified by FCC on silica gel eluting ethyl ether:hexanes (2:98) to give 2-vinyl-cyclopent-1-enecarboxylic acid methyl ester (0.53 g, 59%) as an oil.

27c)
Following a procedure analogous to that used in Example 7, but using the product step 27b and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.065 g, 40%). MS found: $(M+H)^+= 444$.

Example 28 cis-2-{3-[4-(2-Methyl-quinolin-4-ylmethoxy)-phenyl]-4,5-dihydro-isoxazol-5-yl}-cyclopentanecarboxylic acid hydroxyamide 28a)
2-{3-[4-(2-Methyl-quinolin-4-ylmethoxy)-phenyl]-4,5-dihydro-isoxazol-5-yl}-cyclopent-1-enecarboxylic acid methyl ester intermediate from Example 27, was dissolved in ethyl acetate:methanol (1:1) (20 mL), degassed with nitrogen, and charged with 10% palladium on carbon and 50 PSI hydrogen. The reaction was shaken for 3 h, filtered, and concentrated to give cis-2-[3-(4-hydroxy-phenyl)-4,5-dihydro-isoxazol-5-yl]-cyclopentanecarboxylic acid methyl ester (0.127 g, 100%) as an oil. MS found: $(M+H)^+=290$.

28b)
The product from step 28a (0.31 g, 1.1 mmol) was combined with 4-chloromethyl-2-methylquinoline (0.20 g, 1.0 mmol), potassium carbonate (0.22 g, 1.6 mmol) and potassium iodide (0.05 g, 0.3 mmol) in acetontrile (5 mL) under a nitrogen atmosphere and heated to 50° C. for 18 h. The reaction was filtered, concentrated, and purified by FCC on silica gel eluting ethyl an acetate:hexanes gradient to give cis-2-{3-[4-(2-methyl-quinolin-4-ylmethoxy)-phenyl]-4,5-dihydro-isoxazol-5-yl}-cyclopentanecarboxylic acid methyl ester (0.19 g, 47%) as an oil. MS found: $(M+H)^+=445$.

28c)
Following a procedure analogous to that used in Example step 7b, but using the product from step 28b, the title compound was prepared and purified by HPLC on a C-18 column eluting with an acetonitrile:water:TFA gradient to give an amorphous solid (0.085 g, 38%). MS found: $(M+H)^+= 446$.

Example 29 cis-4-{3-[4-(2-Methyl-quinolin-4-ylmethoxy)-phenyl]-4,5-dihydro-isoxazol-5-yl}-pyrrolidine-3-carboxylic acid hydroxyamide Following a procedure analogous to that used in Example 28, but using 4-oxo-pyrrolidine-1,3-dicarboxylic acid 1-tert-butyl ester 3-methyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give the title compound (0.007 g, 20%) as an amorphous solid. MS found: $(M+H)^+=447$.

Example 30 cis-4-{3-[4-(2-Methyl-quinolin-4-ylmethoxy)-phenyl]-4,5-dihydro-isoxazol-5-yl}-tetrahydro-furan-3-carboxylic acid hydroxyamide Following a procedure analogous to that used in Example 28, but using 4-oxo-tetrahydro-furan-3-carboxylic acid methyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.025 g, 68%). MS found: $(M+H)^+=448$.

Example 31

N-Hydroxy-2-{3-[4-(2-methyl-quinolin-4-ylmethoxy)-phenyl]-1-oxa-2-aza-spiro[4.5]dec-2-en-6-yl}-acetamide 31a)
Triphenylphosphoniummethyl bromide (6.9 g, 19.5 mmol) was added to a suspension of sodium hydride (0.78 g, 60% oil dispersion, 19.5 mmol) (hexane washed) in DMF (50 mL) cooled to 0° C. under a nitrogen atmosphere. The reaction was stirred for 1 h, and then (2-oxo-cyclohexyl)- acetic acid ethyl ester (3.0 g, 16.2 mmol) was added. The reaction was allowed to warm to room temperature and stirred for 18 h. The reaction was partitioned between ethyl acetate and water. The organic layer was washed with brine, dried over magnesium sulfate, and concentrated to give a residue. The product was purified by FCC on silica gel eluting with hexane:ethyl acetate (95:5) to give (2-methylene-cyclohexyl)-acetic acid ethyl ester (1.5 g, 50%) as an oil.

31b)

Following a procedure analogous to that used in Example 7, but using the product from step 31a and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.15 g, 32%). MS found: $(M+H)^+=460$.

Example 32

N-Hydroxy-2-{3-[4-(2-methyl-quinolin-4-yl-methoxy)-phenyl]-1,8-dioxa-2-aza-spiro[4.5]dec-2-en-6-yl}-acetamide Following a procedure analogous to that used in Example 31, but using (4-oxo-tetrahydro-pyran-3-yl)-acetic acid ethyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.14 g, 61%). MS found: $(M+H)^+=462$.

Example 33

6-Hydroxycarbamoylmethyl-3-[4-(2-methyl-quinolin-4-ylmethoxy)-phenyl]-1-oxa-2,8-diaza-spiro[4.5]dec-2-ene-8-carboxylic acid tert-butyl ester Following a procedure analogous to that used in Example 31, but using 3-methoxycarbonylmethyl-4-oxo-piperidine-1-carboxylic acid tert-butyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.054 g, 56%). MS found: $(M+H)^+=561$.

Example 34

N-Hydroxy-2-{3-[4-(2-methyl-quinolin-4-yl-methoxy)-phenyl]-1-oxa-2,8-diaza-spiro[4.5]dec-2-en-6-yl}-acetamide 34a)

The intermediate 6-methoxycarbonylmethyl-3-[4-(2-methyl-quinolin-4-ylmethoxy)-phenyl]-1-oxa-2,8-diaza-spiro[4.5]dec-2-ene-8-carboxylic acid tert-butyl ester from Example 33 (0.43 g, 1.87 mmol) was dissolved in methylene chloride (12 mL) and TFA (12 mL) at room temperature under a nitrogen atmosphere. The reaction was stirred for 1 h and concentrated in vacuo to give {3-[4-(2-methyl-quinolin-4-ylmethoxy)-phenyl]-1-oxa-2,8-diaza-spiro[4.5]dec-2-en-6-yl}-acetic acid methyl ester (1.2 g, 100%) crude product. MS found: $(M+H)^+=460$.

34b)

Following a procedure analogous to that used in Example step 7b, but using the product from step 34a, the title compound was prepared and purified by HPLC on a C-18 column eluting with an acetonitrile:water:TFA gradient to give an amorphous solid (0.062 g, 77%). MS found: $(M+H)^+=461$.

Example 35

N-Hydroxy-2-{8-methyl-3-[4-(2-methyl-quinolin-4-ylmethoxy)-phenyl]-1-oxa-2,8-diaza-spiro[4.5]dec-2-en-6-yl}-acetamide Following a procedure analogous to that used in Example 17, but using {3-[4-(2-methyl-quinolin-4-ylmethoxy)-phenyl]-1-oxa-2,8-diaza-spiro[4.5]dec-2-en-6-yl}-acetic acid methyl ester from step 34a, the title compound was prepared and purified by HPLC on a C-18 column eluting with an acetonitrile:water:TFA gradient to give an amorphous solid (0.084 g, 52%). MS found: $(M+H)^+=475$.

Example 36

2-{8-Acetyl-3-[4-(2-methyl-quinolin-4-ylmethoxy)-phenyl]-1-oxa-2,8-diaza-spiro[4.5]dec-2-en-6-yl}-N-hydroxy-acetamide Following a procedure analogous to that used in Example 16, but using {3-[4-(2-methyl-quinolin-4-ylmethoxy)-phenyl]-1-oxa-2,8-diaza-spiro[4.5]dec-2-en-6-yl}-acetic acid methyl ester from step 34a, the title compound was prepared and purified by HPLC on a C-18 column eluting with an acetonitrile:water:TFA gradient to give an amorphous solid (0.077 g, 67%). MS found: $(M+H)^+=503$.

Example 37

7-Methyl-3-[4-(2-methyl-quinolin-4-ylmethoxy)-phenyl]-6-oxo-1-oxa-2,7-diaza-spiro[4.4]non-2-ene-9-carboxylic acid hydroxyamide Following a procedure analogous to that used in Example 31, but using 1-methyl-4-methylene-5-oxo-pyrrolidine-3-carboxylic acid methyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.01 g, 21%). MS found: $(M+H)^+=461$.

Example 38

7-Methyl-3-[4-(2-methyl-quinolin-4-ylmethoxy)-phenyl]-6-oxo-1-oxa-2,7-diaza-spiro[4.5]dec-2-ene-10-carboxylic acid hydroxyamide Following a procedure analogous to that used in Example 31, but using 1-methyl-3-methylene-2-oxo-piperidine-4-carboxylic acid methyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.02 g, 23%). MS found: $(M+H)^+=475$.

Example 39

N-Hydroxy-2-(4-{3-[4-(2-methyl-quinolin-4-yl-methoxy)-phenyl]-4,5-dihydro-isoxazol-5-yl}-tetrahydro-pyran-4-yl)-acetamide 39a)
DIBAL 1 M in methylene chloride (76.9 mL, 76.9 mmol) was added to a solution of (tetrahydro-pyran-4-ylidene)-acetic acid methyl ester (4.0 g, 25.6 mmol) in methylene chloride (100 mL) under nitrogen atmosphere cooled to −78° C. The reaction was stirred for 1 h, allowed to warm to room temperature, and stirred for an additional 2 h. The reaction was cooled to 0° C. and slowly quenched with methanol (35 mL). The reaction was vigorously stirred with water (35 mL) and $Na_2SO_4$ (170 g) for 30 minutes at room temperature. The resulting slurry was filtered and concentrated to give 2-(tetrahydro-pyran-4-ylidene)-ethanol (3.2 g, 97%) as a colorless oil.

39b)
The 2-(tetrahydro-pyran-4-ylidene)-ethanol (3.2 g, 24.9 mmol) was combined with triethylorthoacetate (12 mL) and catalytic propionic acid (0.3 mL) in a sealed tube reactor. The reaction was heated to 170° C. for 18 h, allowed to cool to room temperature, and partitioned between ethyl acetate and aqueous $NaHCO_3$. The organic layer was washed with water, brine, dried over magnesium sulfate, and concentrated to give a crude oil. The product was purified by FCC on silica gel eluting hexane:ethyl acetate (70:30) to give (4-vinyl-tetrahydro-pyran-4-yl)-acetic acid ethyl ester 2.1 g, 42%) as an oil.

39c)
Following a procedure analogous to that used in Example 7, but using (4-vinyl-tetrahydro-pyran-4-yl)-acetic acid ethyl ester from step 39b and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.025 g, 8%). MS found: $(M+H)^+$= 476.

Example 40

2-(1-Acetyl-4-{3-[4-(2-methyl-quinolin-4-yl-methoxy)-phenyl]-4,5-dihydro-isoxazol-5-yl}-piperidin-4-yl)-N-hydroxy-acetamide Following a procedure analogous to that used in Example 39, but using (1-acetyl-piperidin-4-ylidene)-acetic acid ethyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.120 g, 20%). MS found: $(M+H)^+$=517.

Example 41

3-Hydroxycarbamoylmethyl-3-{3-[4-(2-methyl-quinolin-4-ylmethoxy)-phenyl]-4,5-dihydro-isoxazol-5-yl}-pyrrolidine-1-carboxylic acid tert-butyl ester Following a procedure analogous to that used in Example 39, but using 3-methoxycarbonylmethylene-pyrrolidine-1-carboxylic acid tert-butyl ester and 4-(2-methyl-quinolin-4-ylmethoxy)-benzaldehyde oxime from step 1b, the title compound was prepared and purified by HPLC on a C-18 column eluting with an acetonitrile:water:TFA gradient to give an amorphous solid (0.065 g, 72%). MS found: $(M+H)^+$= 561.

Example 42

N-Hydroxy-2-(3-{3-[4-(2-methyl-quinolin-4-yl-methoxy)-phenyl]-4,5-dihydro-isoxazol-5-yl}-pyrrolidin-3-yl)-acetamide 42a)
The intermediate 3-ethoxycarbonylmethyl-3-{3-[4-(2-methyl-quinolin-4-ylmethoxy)-phenyl]-4,5-dihydro-isoxazol-5-yl}-pyrrolidine-1-carboxylic acid tert-butyl ester (0.35 g, 0.61 mmol) from example 41 was dissolved in methylene chloride (5 mL) and TFA (3 mL) under nitrogen atmosphere at room temperature. The reaction was stirred for 2 h and was concentrated in vacuo to give (3-{3-[4-(2-methyl-quinolin-4-ylmethoxy)-phenyl]-4,5-dihydro-isoxazol-5-yl}-pyrrolidin-3-yl)-acetic acid ethyl ester as a crude oily residue. MS found: $(M+H)^+$=474.

42b)
Following a procedure analogous to that used in Example step 7b, but using the product from step 42a, the title compound was prepared and purified by HPLC on a C-18 column eluting with an acetonitrile:water:TFA gradient to give an amorphous solid (0.045 g, 89%). MS found: $(M+H)^+$= 461.

Example 43

N-Hydroxy-2-(1-methyl-3-{3-[4-(2-methyl-quinolin-4-ylmethoxy)-phenyl]-4,5-dihydro-isoxazol-5-yl}-pyrrolidin-3-yl)-acetamide Following a procedure analogous to that used in Example 17, but using (3-{3-[4-(2-methyl-quinolin-4-ylmethoxy)-phenyl]-4,5-dihydro-isoxazol-5-yl}-pyrrolidin-3-yl)-acetic acid ethyl ester from step 42a, the title compound was prepared and purified by HPLC on a C-18 column eluting with an acetonitrile:water:TFA gradient to give an amorphous solid (0.045 g, 53%). MS found: $(M+H)^+$=475.

Tables 1–6 below provide representative Examples, the synthesis of which is described above, of the compounds of the present invention.

TABLE 1

| Ex | $R^1$ | $R^2$ | $R^{4a}$ | MS [M + H] |
|---|---|---|---|---|
| 1 | H | H | H | 392 |
| 2 | $CH_3$ | H | H | 406 |
| 3 | H | H | morpholin-4-ylmethyl | 491 |
| 4 | H | H | piperazin-ylmethyl | 490 |
| 5 | H | H | dimethylaminomethyl | 449 |

TABLE 2

[Structure: hydroxamic acid - CR¹R² - CR³R⁴ - isoxazoline - phenyl - OCH₂ - 2-methylquinoline]

| Ex | R¹ | R² | R³ | R⁴ | MS [M + H] |
|----|----|----|----|----|------------|
| 6 | H | H | H | H | 406 |
| 7 | H | H | CH₃ | CH₃ | 434 |
| 8 | —NBoc | H | H | H | 521 |
| 9 | NH₂ | H | H | H | 421 |
| 10 | H | H | NH₂ | H | 421 |
| 11 | H | H | —SCH₃ | H | 452 |
| 12 | H | H | morpholin-4-yl | H | 491 |
| 13 | H | H | CH₃ | NH₂ | 435 |
| 14 | H | H | —NHCO-2-furan | H | 515 |
| 15 | H | H | pyrrolidin-1-yl | H | 475 |
| 16 | H | H | —NHCOCH₃ | H | 463 |
| 17 | H | H | —N(CH₃)₂ | H | 449 |
| 18 | H | H | —NHCONHCH₂CH₃ | H | 492 |
| 19 | H | H | —NHSO₂CH₃ | H | 499 |
| 20 | H | H | —NHCH₂-2-furan | H | 501 |
| 21 | H | H | —NH-benzyl | H | 511 |
| 22 | H | H | —NHCOOCH₂(CH₃)₂ | H | 521 |

TABLE 3

| Ex | R⁴ᵃ | MS [M + H] |
|----|-----|------------|
| 23 | CH₃ | 420 |
| 24 | —CH₂OH | 436 |
| 25 | —COOCH₃ | 464 |
| 26 | —CONHOH | 465 |

TABLE 4

| Ex | —CR¹R²—CR³R⁴— | MS [M + H] |
|----|---------------|------------|
| 27 | cyclopentene-diyl | 444 |

TABLE 4-continued

| Ex | —CR¹R²—CR³R⁴— | MS [M + H] |
|----|---------------|------------|
| 28 | cyclopentane-diyl | 446 |
| 29 | pyrrolidine-3,4-diyl (NH) | 447 |
| 30 | tetrahydrofuran-3,4-diyl | 448 |
| 39 | tetrahydropyran-4,4-diyl | 476 |
| 40 | 1-acetylpiperidine-4,4-diyl | 517 |
| 41 | 1-Boc-pyrrolidine-3,3-diyl | 561 |
| 42 | pyrrolidine-3,3-diyl (NH) | 461 |
| 43 | 1-methylpyrrolidine-3,3-diyl | 475 |

TABLE 5

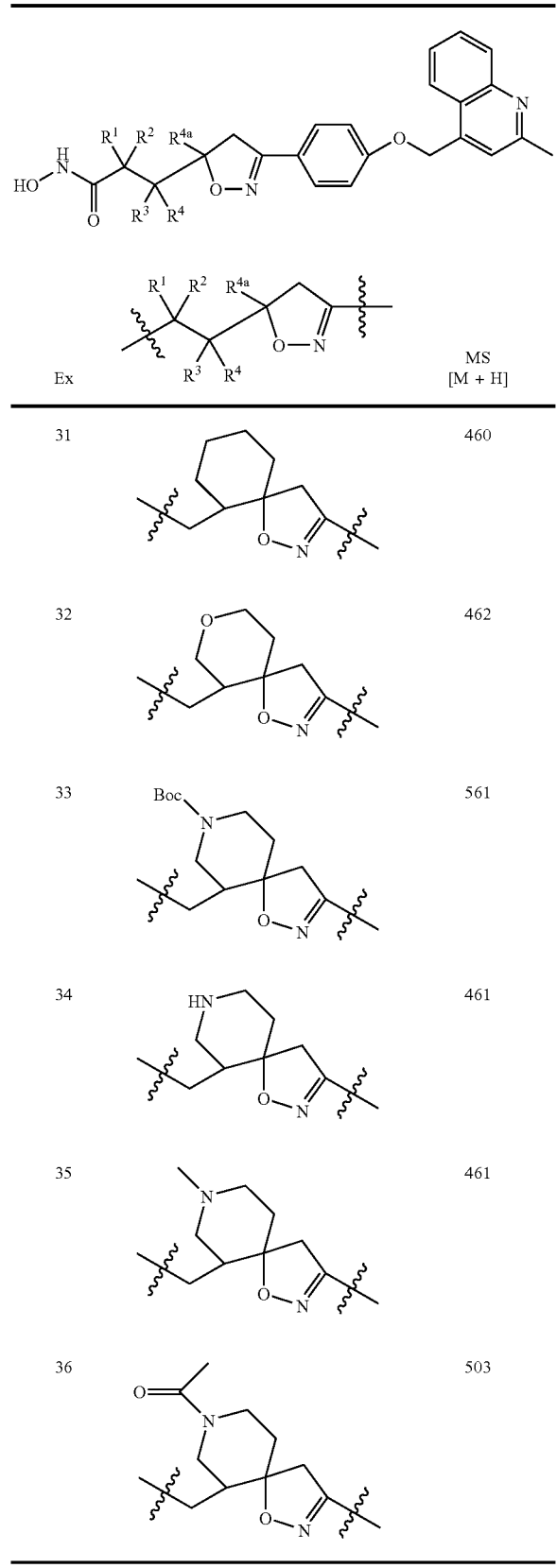

| Ex | R¹ R² R⁴ᵃ / R³ R⁴ structure | MS [M + H] |
|---|---|---|
| 31 | (cyclohexane spiro) | 460 |
| 32 | (tetrahydropyran spiro) | 462 |
| 33 | (Boc-piperidine spiro) | 561 |
| 34 | (HN-piperidine spiro) | 461 |
| 35 | (N-methyl piperidine spiro) | 461 |
| 36 | (N-acetyl piperidine spiro) | 503 |

TABLE 6

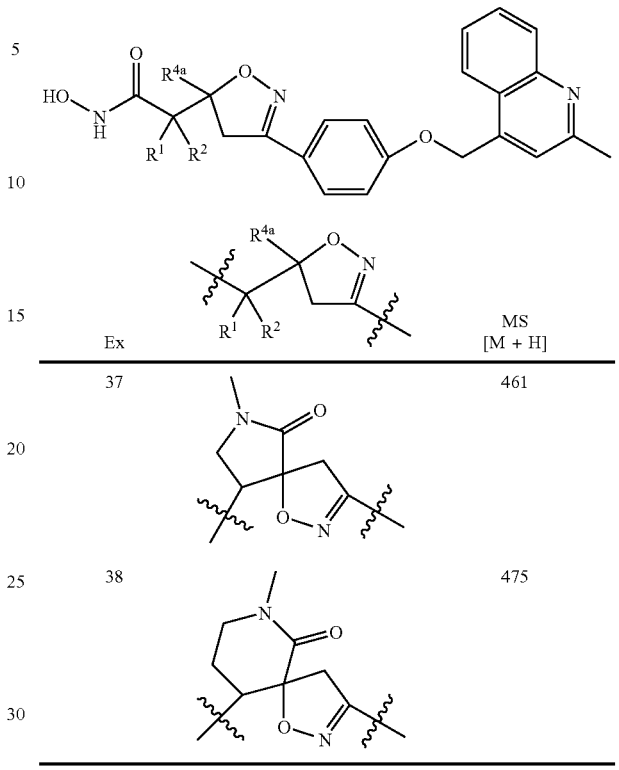

| Ex | R¹ R² R⁴ᵃ structure | MS [M + H] |
|---|---|---|
| 37 | (N-methyl pyrrolidinone spiro) | 461 |
| 38 | (N-methyl piperidinone spiro) | 475 |

Utility

The compounds of formula I are expected to possess matrix metalloprotease and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TACE and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthopathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denotes agents that selectively inhibit COX-2 function. Such agents include, but are not limited to, celecoxib (Celebrex), rofecoxib (Vioxx), meloxicam (Movicox), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel), infliximab (Remicade), adalimumab (D2E7), CDP-571 (Humicade), and CDP-870.

Other anti-inflammatory agents that may be used in combination with the compounds of this invention, include, but are not limited to, methotrexate, interleukin-1 antagonists (e.g., anakinra (Kineret)), dihydroorotate synthase inhibitors (e.g., leflunomide (Arava)), and p38 MAP kinase inhibitors.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 μM for the inhibition of a desired MP. Preferred compounds of the present invention have $K_i$'s or $IC_{50}$'s of $\leq 1$ μM. More preferred compounds of the present invention have $K_i$'s or $IC_{50}$'s of $\leq 0.1$ μM. Even more preferred compounds of the present invention have $K_i$'s or $IC_{50}$'s of $\leq 0.01$ μM.

TNF PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2 \times 10^6$ cells/mL in 96 well polystyrene plates. Cells were preincubated 10 minutes with compound, then stimulated with 1 μg/mL LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 minutes before the addition of 100 ng/mL LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-α production by a standard sandwich ELISA. The ability of compounds to inhibit TNF-α production by 50% compared to DMSO treated cultures is given by the $IC_{50}$ value.

TNF Induction In Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibiton, the IC50 values were converted to Ki values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM.

Using the methodology described above, a number of compounds of the present invention were found to exhibit $K_i$'s of $\leq 10$ μM, thereby confirming the utility of the compounds of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder (as defined previously). In another embodiment, the package insert states that the pharmaceutical composition can be used in combination (as defined previously) with a second therapeutic agent to treat an inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthitic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, thee, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant thoughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

The compounds of the present invention may be administered in combination with a second therapeutic agent, especially non-steroidal anti-inflammatory drugs (NSAID's). The compound of Formula I and a second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material that affects a sustained-release thoughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I or II:

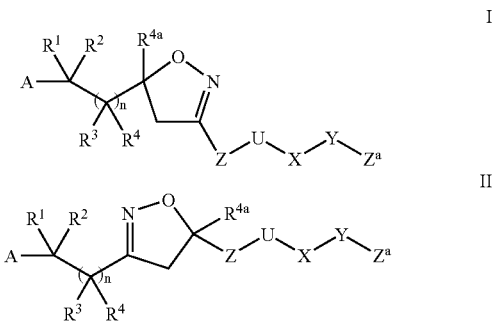

or a stereoisomer or pharmaceutically acceptable salt form thereof, wherein;

A is —C(O)NHOH, —C(O)NHOR$^5$, —C(O)NHOR$^6$, —N(OH)COR$^5$, or —N(OH)CHO;

U is absent or is O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X is absent or is $C_{1-10}$ alkylene, $C_{2-10}$ alkenylene, or $C_{2-10}$ alkynylene;

Y is absent or is O, NR$^{a1}$, S(O)$_p$, or C(O);

Z is a $C_{3-13}$ carbocycle substituted with 1–5 R$^b$, or a 5–14 membered heterocycle consisting of carbon atoms and 1–4 heteroatoms selected from N, O, and S(O)$_p$, and substituted with 1–5 R$^b$;

Z$^a$ is H, $C_{3-13}$ carbocycle substituted with 1–5 R$^c$, or a 5–14 membered heterocycle consisting of carbon atoms and 1–4 heteroatoms selected from N, O, and S(O)$_p$, and substituted with 1–5 R$^c$;

provided that U, Y, Z, and Z$^a$ do not combine to form a N—N, N—O, O—N, O—O, S(O)$_p$—O, O—S(O)$_p$, or S(O)$_p$—S(O)$_p$ group;

R$^1$ is Q, $C_{1-6}$ alkylene-Q, $C_{2-6}$ alkenylene-Q, $C_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$OC(O)

$(CR^aR^{a1})_s$-Q, $-(CR^aR^{a1})_rC(O)NR^aR^{a1}$, $-(CR^aR^{a1})_rC(O)NR^a(CR^aR^{a1})_s$-Q, $-(CR^aR^{a1})_rNR^aC(O)(CR^aR^{a1})_s$-Q, $-(CR^aR^{a1})_rOC(O)O(CR^aR^{a1})_s$-Q, $-(CR^aR^{a1})_rOC(O)NR^a(CR^aR^{a1})_s$-Q, $-(CR^aR^{a1})_rNR^aC(O)O(CR^aR^{a1})_s$-Q, $-(CR^aR^{a1})_rNR^aC(O)NR^a(CR^aR^{a1})_s$-Q, $-(CR^aR^{a1})_rS(O)_p(CR^aR^{a1})_s$-Q, $-(CR^aR^{a1})_rSO_2NR^a(CR^aR^{a1})_s$-Q, $-(CR^aR^{a1})_rNR^aSO_2(CR^aR^{a1})_s$-Q, or $-(CR^aR^{a1})_rNR^aSO_2NR^a(CR^aR^{a1})_s$-Q;

Q is, independently at each occurrence, H, $CHF_2$, $CH_2F$, $CF_3$, a $C_{3-13}$ carbocycle substituted with 0–5 $R^d$, or a 5–14 membered heterocycle consisting of carbon atoms and 1–4 heteroatoms selected from N, O, and $S(O)_p$, and substituted with 0–5 $R^d$;

$R^2$ is $Q^1$, $C_{1-6}$ alkylene-$Q^1$, $C_{2-6}$ alkenylene-$Q^1$, $C_{2-6}$ alkynylene-$Q^1$, $-(CR^aR^{a1})_rO(CR^aR^{a1})_s$-Q, $-(CR^aR^{a1})_rNR^a(CR^aR^{a1})_s$-$Q^1$, $-(CR^aR^{a1})_rC(O)(CR^aR^{a1})_s$-$Q^1$, $-(CR^aR^{a1})_rC(O)O(CR^aR^{a1})_s$-$Q^1$, $-(CR^aR^{a1})_rC(O)NR^aR^{a1}$, or $-(CR^aR^{a1})_rC(O)NR^a(CR^aR^{a1})_s$-$Q^1$, $Q^1$ is, independently at each occurrence, H, a $C_{3-13}$ carbocycle substituted with 0–5 $R^d$, or a 5–14 membered heterocycle consisting of carbon atoms and 1–4 heteroatoms selected from N, O, and $S(O)_p$, and substituted with 0–5 $R^d$;

alternatively, $R^1$ and $R^2$ combine, along with the carbon atom to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

$R^3$ is Q, $C_{1-6}$ alkylene-Q, $C_{2-6}$ alkenylene-Q, $C_{2-6}$ alkynylene-Q, $-(CR^aR^{a1})_rO(CR^aR^{a1})_s$-Q, $-(CR^aR^{a1})_rNR^a(CR^aR^{a1})_s$-Q, $-(CR^aR^{a1})_rC(O)(CR^aR^{a1})_s$-Q, $-(CR^aR^{a1})_rC(O)O(CR^aR^{a1})_s$-Q, $-(CR^aR^{a1})_rOC(O)(CR^aR^{a1})_s$-Q, $-(CR^aR^{a1})_rC(O)NR^aR^{a1}$, $-(CR^aR^{a1})_rC(O)NR^a(CR^aR^{a1})_s$-Q, $-(CR^aR^{a1})_rNR^aC(O)(CR^aR^{a1})_s$-Q, $-(CR^aR^{a1})_rOC(O)O(CR^aR^{a1})_s$-Q, $-(CR^aR^{a1})_rOC(O)NR^a(CR^aR^{a1})_s$-Q, $-(CR^aR^{a1})_rNR^aC(O)O(CR^aR^{a1})_s$-Q, $-(CR^aR^{a1})_rNR^aC(O)NR^a(CR^aR^{a1})_s$-Q, $-(CR^aR^{a1})_rS(O)_p(CR^aR^{a1})_s$-Q, $-(CR^aR^{a1})_rSO_2NR^a(CR^aR^{a1})_s$-Q, $-(CR^aR^{a1})_rNR^aSO_2(CR^aR^{a1})_s$-Q, or $-(CR^aR^{a1})_rNR^aSO_2NR^a(CR^aR^{a1})_s$-Q;

alternatively, $R^1$ and $R^3$ combine, along with the carbon atom to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

alternatively, when $R^1$ and $R^3$ combine to form a carbocyclic or heterocyclic ring, the $R^2$ and $R^4$ combine to form a double bond;

$R^4$ is $Q^1$, $C_{1-6}$ alkylene-$Q^1$, $C_{2-6}$ alkenylene-$Q^1$, $C_{2-6}$ alkynylene-$Q^1$, $-(CR^aR^{a1})_rO(CR^aR^{a1})_s$-$Q^1$, $-(CR^aR^{a1})_rNR^a(CR^aR^{a1})_s$-$Q^1$, $-(CR^aR^{a1})_rC(O)(CR^aR^{a1})_s$-$Q^1$, $-(CR^aR^{a1})_rC(O)O(CR^aR^{a1})_s$-$Q^1$, $-(CR^aR^{a1})_rC(O)NR^aR^{a1}$, or $-(CR^aR^{a1})_rC(O)NR^a(CR^aR^{a1})_s$-$Q^1$, alternatively, $R^3$ and $R^4$ combine, along with the carbon atom to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

$R^{4a}$ is Q, $C_{1-6}$ alkylene-Q, $C_{2-6}$ alkenylene-Q, $C_{2-6}$ alkynylene-Q, $-(CR^aR^{a1})_rO(CR^aR^{a1})_s$-Q, $-(CR^aR^{a1})_rNR^a(CR^aR^{a1})_s$-Q, $-(CR^aR^{a1})_rC(O)(CR^aR^{a1})_s$-Q, $-(CR^aR^{a1})_rC(O)O(CR^aR^a)_s$-Q, $-(CR^aR^{a1})_rC(O)NR^aR^{a1}$, $-(CR^aR^{a1})_rC(O)NR^aOR^a$, $-(CR^aR^{a1})_rC(O)NR^a(CR^aR^{a1})_s$-Q, $-(CR^aR^{a1})_rNR^aC(O)(CR^aR^{a1})_s$-Q, $-(CR^aR^{a1})_rNR^aC(O)O(CR^aR^{a1})_s$-Q, $-(CR^aR^{a1})_rS(O)_p(CR^aR^{a1})_s$-Q, or $-(CR^aR^{a1})_rSO_2NR^a(CR^aR^{a1})_s$-Q;

alternatively, $R^1$ and $R^{4a}$ in Formula I combine, along with the carbon atoms to which they are attached, to form a 3–7 membered carbocyclic or heterocyclic ring consisting of: carbon atoms and 0–3 heteroatoms selected from the group consisting of N, O, and $S(O)_p$ and substituted with 0–3 $R^d$, provided that n is 0;

alternatively, $R^3$ and $R^{4a}$ in Formula I combine, along with the carbon atoms to which they are attached, to form a 3–7 membered carbocyclic or heterocyclic ring consisting of: carbon atoms and 0–3 heteroatoms selected from the group consisting of N, O, and $S(O)_p$ and substituted with 0–2 $R^d$;

$R^a$ is, independently at each occurrence, H, $C_{1-6}$ alkyl, phenyl, or benzyl;

$R^{a1}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or $-(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

$R^{a2}$ is, independently at each occurrence, $C_{1-4}$ alkyl, phenyl, or benzyl;

$R^{a3}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or $-(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^b$ is, independently at each occurrence, H, $C_{1-6}$ alkyl substituted with 0–1 $R^{c1}$, $OR^a$, $SR^a$, Cl, F, Br, I, =O, CN, $NO_2$, $-NR^aR^{a1}$, $-C(O)R^a$, $-C(O)OR^a$, $-C(O)NR^aR^{a1}$, $-C(S)NR^aR^{a1}$, $-NR^aC(O)NR^aR^{a1}$, $-OC(O)NR^aR^{a1}$, $-NR^aC(O)OR^a$, $-S(O)_2NR^aR^{a1}$, $-NR^aS(O)_2R^{a3}$, $-NR^aS(O)_2NR^aR^{a1}$, $-OS(O)_2NR^aR^{a1}$, $-S(O)_pR^{a3}$, $CF_3$, $CF_2CF_3$, $CHF_2$, $CH_2F$, or phenyl;

$R^c$ is, independently at each occurrence, H, $OR^a$, Cl, F, Br, I, =O, CN, $NO_2$, $CF_3$, $CF_2CF_3$, $CH_2F$, $CHF_2$, $-(CR^aR^{a1})_rNR^aR^{a1}$, $-(CR^aR^{a1})_rC(=NCN)NR^aR^{a1}$, $-(CR^aR^{a1})_rC(=NR^a)NR^aR^{a1}$, $-(CR^aR^{a1})_rC(=NOR^a)NR^aR^{a1}$, $-(CR^aR^{a1})_rC(O)NR^aOH$, $-(CR^aR^{a1})_rC(O)R^{a1}$, $-(CR^aR^{a1})_rC(O)OR^{a1}$, $-(CR^aR^{a1})_rC(S)OR^{a1}$, $-(CR^aR^{a1})_rC(O)NR^aR^{a1}$, $-(CR^aR^{a1})_rNR^aC(O)R^{a1}$, $-(CR^aR^{a1})_rC(S)NR^aR^{a1}$, $-(CR^aR^{a1})_rOC(O)NR^aR^{a1}$, $-(CR^aR^{a1})_rNR^aC(O)OR^{a1}$, $-(CR^aR^{a1})_rNR^aC(O)NR^aR^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, $-(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, $-(CR^aR^{a1})_r$-$C_{3-10}$ carbocycle substituted with 0–2 $R^{c1}$, or $-(CR^aR^{a1})_r$-5–14 membered heterocycle consisting of carbon atoms and 1–4 heteroatoms selected from N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of: carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

$R^{c1}$ is, independently at each occurrence, H, $C_{1-4}$ alkyl, $OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, $OR^a$, Cl, F, Br, I, =O, CN, $NO_2$, —$NR^aR^{a1}$, —$C(O)R^a$, —$C(O)OR^a$, —$C(O)NR^aR^{a1}$, —$C(O)NR^aOR^a$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, $CF_3$, $CF_2CF_3$, $C_{3-10}$ carbocycle, or a 5–14 membered heterocycle consisting of carbon atoms and 1–4 heteroatoms selected from N, O, and $S(O)_p$;

$R^5$ is, independently at each occurrence, $C_{1-10}$ alkyl substituted with 0–2 $R^b$, or $C_{1-8}$ alkyl substituted with 0–2 $R^e$;

$R^e$ is phenyl substituted with 0–2 $R^b$, or biphenyl substituted with 0–2 $R^b$;

$R^6$ is, phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, or —$CH(R^8)OC(=O)OR^9$;

$R^7$ is H, $C_{1-10}$ alkyl, $C_{2-6}$ alkenyl, $C_{3-6}$ cycloalkyl-$C_{1-3}$ alkyl-, or phenyl-$C_{1-6}$ alkyl-;

$R^{7a}$ is H, $C_{1-10}$ alkyl, $C_{2-6}$ alkenyl, $C_{3-6}$ cycloalkyl-$C_{1-3}$ alkyl-, or phenyl-$C_{1-6}$ alkyl-;

$R^8$ is H or $C_{1-4}$ linear alkyl;

$R^9$ is H, $C_{1-8}$ alkyl substituted with 1–2 $R^f$, $C_{3-8}$ cycloalkyl substituted with 1–2 $R^f$, or phenyl substituted with 0–2 $R^b$;

$R^f$ is, independently at each occurrence, $C_{1-4}$ alkyl, $C_{3-8}$ cycloalkyl, $C_{1-5}$ alkoxy, or phenyl substituted with 0–2 $R^b$;

n is 0 or 1;

p, at each occurrence, is selected from 0, 1, and 2;

r, at each occurrence, is selected from 0, 1, 2, 3, and 4; and s, at each occurrence, is selected from 0, 1, 2, 3, and 4.

2. A compound according to claim 1, wherein:

U is absent or is O, $NR^{a1}$, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$;

X is absent or is $C_{1-3}$ alkylene or $C_{3-4}$ alkynylene;

Y is absent or is O, $NR^{a1}$, $S(O)_p$, or C(O);

Z is a $C_{5-10}$ carbocycle substituted with 1–3 $R^b$, or a 5–10 membered heterocycle consisting of carbon atoms and 1–4 heteroatoms selected from N, O, and $S(O)_p$, and substituted with 1–3 $R^b$;

$Z^a$ is H, $C_{3-13}$ carbocycle substituted with 1–3 $R^c$, or a 5–14 membered heterocycle consisting of carbon atoms and 1–4 heteroatoms selected from N, O, and $S(O)_p$, and substituted with 1–3 $R^c$;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)O(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q;

Q is, independently at each occurrence, H, $CHF_2$, $CH_2F$, $CF_3$, a $C_{3-13}$ carbocycle substituted with 0–3 $R^d$, or a 5–14 membered heterocycle consisting of carbon atoms and 1–4 heteroatoms selected from N, O, and $S(O)_p$, and substituted with 0–3 $R^d$;

$R^2$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, or —$(CR^aR^{a1})_rC(O)NR^a(CR^aR^{a1})_s$-$Q^1$, $Q^1$ is, independently at each occurrence, H, a $C_{3-10}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

alternatively, $R^1$ and $R^2$, when attached to the same carbon atom, combine to form a 5–6 membered carbocyclic or heterocyclic ring consisting of: carbon atoms and 0–3 heteroatoms selected from the group consisting of N, O, and $S(O)_p$ and substituted with 0–2 $R^d$;

$R^3$ is Q, $C_{1-6}$ alkylene-Q, $C_{2-6}$ alkenylene-Q, $C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rNR^aC(O)NR^a(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, —$(CR^aR^{a1})_rNR^aSO_2(CR^aR^{a1})_s$-Q, or —$(CR^aR^{a1})_rNR^aSO_2NR^a(CR^aR^{a1})_s$-Q;

alternatively, $R^1$ and $R^3$ combine, along with the carbon atom to which they are attached, to form a 4–7 membered carbocyclic or heterocyclic ring consisting of: carbon atoms and 0–3 heteroatoms selected from the group consisting of N, O, and $S(O)_p$ and substituted with 0–2 $R^d$;

alternatively, when $R^1$ and $R^3$ combine to form a carbocyclic or heterocyclic ring, the $R^2$ and $R^4$ combine to form a double bond;

$R^4$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)$ $(CR^aR^{a1})_s$-$Q^1$, —$(CR^aR^{a1})_r$C(O)O$(CR^aR^{a1})_s$-$Q^1$, or —$(CR^aR^{a1})_r$C(O)NR$^a$$(CR^aR^{a1})_s$-$Q^1$, alternatively, $R^3$ and $R^4$ combine, along with the carbon atom to which they are attached, to form a 4–7 membered carbocyclic or heterocyclic ring consisting of: carbon atoms and 0–3 heteroatoms selected from the group consisting of N, O, and S(O)$_p$ and substituted with 0–2 $R^d$;

$R^{4a}$ is Q, $C_{1-6}$ alkylene-Q, $C_{2-6}$ alkenylene-Q, $C_{2-6}$ alkynylene-Q, —$(CR^aR^{a1})_r$O$(CR^aR^{a1})_s$-Q, —$(CR^aR^{a1})_r$NR$^a$$(CR^aR^{a1})_s$-Q, —$(CR^aR^{a1})_r$C(O)$(CR^aR^{a1})_s$-Q, —$(CR^aR^{a1})_r$C(O)O$(CR^aR^{a1})_s$-Q, —$(CR^aR^{a1})_r$C(O)NR$^a$R$^{a1}$, —$(CR^aR^{a1})_r$C(O)NR$^a$OR$^a$, —$(CR^aR^{a1})_r$C(O)NR$^a$$(CR^aR^{a1})_s$-Q, —$(CR^aR^{a1})_r$NR$^a$C(O)$(CR^aR^{a1})_s$-Q, or —$(CR^aR^{a1})_r$SO$_2$NR$^a$$(CR^aR^{a1})_s$-Q;

alternatively, $R^1$ and $R^{4a}$ in Formula I combine, along with the carbon atoms to which they are attached, to form a 4–7 membered carbocyclic or heterocyclic ring consisting of: carbon atoms and 0–3 heteroatoms selected from the group consisting of N, O, and S(O)$_p$ and substituted with 0–3 $R^d$, provided that n is 0;

alternatively, $R^3$ and $R^{4a}$ in Formula I combine, along with the carbon atoms to which they are attached, to form a 4–7 membered carbocyclic or heterocyclic ring consisting of: carbon atoms and 0–3 heteroatoms selected from the group consisting of N, O, and S(O)$_p$ and substituted with 0–2 $R^d$;

$R^a$ is, independently at each occurrence, H, $C_{1-6}$ alkyl, phenyl, or benzyl;

$R^{a1}$ is, independently at each occurrence, H, $C_{1-6}$ alkyl, $C_{2-6}$ alkenyl, $C_{2-6}$ alkynyl, or —$(CH_2)_r$-3–8 membered carbocyclic or heterocyclic ring consisting of carbon atoms and 0–2 ring heteroatoms selected from N, NR$^{a2}$, O, and S(O)$_p$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, NR$^{a2}$, O, and S(O)$_p$;

$R^c$ is, independently at each occurrence, H, OR$^a$, Cl, F, Br, =O, CN, NO$_2$, CF$_3$, CH$_2$F, CHF$_2$, CF$_2$CF$_3$, —$(CR^aR^{a1})_r$NR$^a$R$^{a1}$, —$(CR^aR^{a1})_r$C(O)R$^{a1}$, —$(CR^aR^{a1})_r$C(O)OR$^{a1}$, —$(CR^aR^{a1})_r$C(O)NR$^a$R$^{a1}$, —$(CR^aR^{a1})_r$NR$^a$C(O)R$^{a1}$, —$(CR^aR^{a1})_r$S(O)$_p$R$^{a3}$, —$(CR^aR^{a1})_r$SO$_2$NR$^a$R$^{a1}$, —$(CR^aR^{a1})_r$NR$^a$SO$_2$R$^{a3}$, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, —$(CH_2)_r$-$C_{3-6}$ carbocycle substituted with 0–2 $R^{c1}$, or —$(CH_2)_r$-5–6 membered heterocycle consisting of carbon atoms and 1–4 heteroatoms selected from N, O, and S(O)$_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and S(O)$_p$;

$R^d$ is, independently at each occurrence, $C_{1-6}$ alkyl, OR$^a$, Cl, F, Br, =O, CN, NO$_2$, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, CF$_3$, $C_{3-6}$ carbocycle, or a 5–6 membered heterocycle consisting of carbon atoms and 1–4 heteroatoms selected from N, O, and S(O)$_p$;

$R^e$ is, independently at each occurrence, $C_{1-6}$ alkyl substituted with 0–2 $R^b$, or $C_{1-4}$ alkyl substituted with 0–2 $R^e$; and $R^f$ is, independently at each occurrence, $C_{1-4}$ alkyl, $C_{3-6}$ cycloalkyl, $C_{1-5}$ alkoxy, or phenyl substituted with 0–2 $R^b$.

3. A compound according to claim 2, wherein:

A is —C(O)NHOH or —N(OH)CHO;

U is absent or is O, NR$^{a1}$, C(O), CR$^a$(OH), C(O)NR$^{a1}$, NR$^{a1}$C(O), S(O)$_p$, S(O)$_p$NR$^{a1}$, or NR$^{a1}$S(O)$_p$;

X is absent or is methylene, ethylene, propynylene, or butynylene;

Z is a $C_{5-10}$ carbocycle substituted with 1–2 $R^b$, or a 5–10 membered heterocycle consisting of carbon atoms and 1–4 heteroatoms selected from N, O, and S(O)$_p$, and substituted with 1–2 $R^b$;

$Z^a$ is H, $C_{5-10}$ carbocycle substituted with 1–3 $R^c$, or a 5–10 membered heterocycle consisting of carbon atoms and 1–4 heteroatoms selected from N, O, and S(O)$_p$, and substituted with 1–3 $R^c$;

provided that U, Y, Z, and $Z^a$ do not combine to form a N—N, N—O, O—N, O—O, S(O)$_p$—O, O—S(O)$_p$, or S(O)$_p$—S(O)$_p$ group;

$R^1$ is Q, $C_{1-6}$ alkylene-Q, $C_{2-6}$ alkenylene-Q, $C_{2-6}$ alkynylene-Q, —$(CR^aR^{a1})_r$O$(CR^aR^{a1})_s$-Q, —$(CR^aR^{a1})_r$NR$^a$$(CR^aR^{a1})_s$-Q, —$(CR^aR^{a1})_r$C(O)$(CR^aR^{a1})_s$-Q, —$(CR^aR^{a1})_r$C(O)O$(CR^aR^{a1})_s$-Q, —$(CR^aR^{a1})_r$C(O)NR$^a$R$^{a1}$, —$(CR^aR^{a1})_r$C(O)NR$^a$$(CR^aR^{a1})_s$-Q, —$(CR^aR^{a1})_r$NR$^a$C(O)$(CR^aR^{a1})_s$-Q, —$(CR^aR^{a1})_r$OC(O)NR$^a$$(CR^aR^{a1})_s$-Q, —$(CR^aR^{a1})_r$NR$^a$C(O)O$(CR^aR^{a1})_s$-Q, —$(CR^aR^{a1})_r$S(O)$_p$$(CR^aR^{a1})_s$-Q, —$(CR^aR^{a1})_r$SO$_2$NR$^a$$(CR^aR^{a1})_s$-Q, or —$(CR^aR^{a1})_r$NR$^a$SO$_2$$(CR^aR^{a1})_s$-Q;

Q is, independently at each occurrence, H, a $C_{3-8}$ carbocycle substituted with 0–3 $R^d$, or a 5–10 membered heterocycle consisting of carbon atoms and 1–4 heteroatoms selected from N, O, and S(O)$_p$, and substituted with 0–3 $R^d$;

$R^2$ is $Q^1$, $C_{1-6}$ alkylene-$Q^1$, $C_{2-6}$ alkenylene-$Q^1$, —$(CR^aR^{a1})_r$O$(CR^aR^{a1})_s$-$Q^1$, —$(CR^aR^{a1})_r$NR$^a$$(CR^aR^{a1})_s$-$Q^1$, or —$(CR^aR^{a1})_r$C(O)$(CR^aR^{a1})_s$-$Q^1$;

$Q^1$ is, independently at each occurrence, H, a $C_{5-10}$ carbocycle substituted with 0–2 $R^d$, or a 5–10 membered heterocycle consisting of carbon atoms and 1–4 heteroatoms selected from N, O, and S(O)$_p$, and substituted with 0–2 $R^d$;

$R^3$ is Q, $C_{1-6}$ alkylene-Q, $C_{2-6}$ alkenylene-Q, $C_{2-6}$ alkynylene-Q, —$(CR^aR^{a1})_r$O$(CR^aR^{a1})_s$-Q, —$(CR^aR^{a1})_r$NR$^a$$(CR^aR^{a1})_s$-Q, —$(CR^aR^{a1})_r$C(O)$(CR^aR^{a1})_s$-Q, —$(CR^aR^{a1})_r$NR$^a$C(O)$(CR^aR^{a1})_s$-Q, —$(CR^aR^{a1})_r$NR$^a$C(O)O$(CR^aR^{a1})_s$-Q, —$(CR^aR^{a1})_r$NR$^a$C(O)NR$^a$$(CR^aR^{a1})_s$-Q, —$(CR^aR^{a1})_r$S(O)$_p$$(CR^aR^{a1})_s$-Q, —$(CR^aR^{a1})_r$SO$_2$NR$^a$$(CR^aR^{a1})_s$-Q, or —$(CR^aR^{a1})_r$NR$^a$SO$_2$$(CR^aR^{a1})_s$-Q;

$R^4$ is $Q^1$, $C_{1-6}$ alkylene-$Q^1$, $C_{2-6}$ alkenylene-$Q^1$, —$(CR^aR^{a1})_r$O$(CR^aR^{a1})_s$-$Q^1$, —$(CR^aR^{a1})_r$NR$^a$$(CR^aR^{a1})_s$-$Q^1$, or —$(CR^aR^{a1})_r$C(O)$(CR^aR^{a1})_s$-$Q^1$, $R^{4a}$ is Q, $C_{1-4}$ alkylene-Q, —$(CH_2)_r$O$(CH_2)_s$-Q, —$(CH_2)_r$NR$^a$$(CH_2)_s$-Q, —$(CH_2)_r$C(O)$(CH_2)_s$-Q, —$(CH_2)_r$C(O)$(CH_2)_s$-Q, —$(CH_2)_r$C(O)NR$^a$R$^{a1}$, —$(CH_2)_r$C(O)NR$^a$OR$^a$, —$(CH_2)_r$C(O)NR$^a$$(CH_2)_s$-Q, —$(CH_2)_r$NR$^a$C(O)$(CH_2)_s$-Q, or —$(CH_2)_r$NR$^a$C(O)O$(CH_2)_s$-Q;

$R^{a3}$ is, independently at each occurrence, H, $C_{1-6}$ alkyl, $C_{2-6}$ alkenyl, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^c$ is, independently at each occurrence, H, $OR^a$, Cl, F, Br, =O, $CF_3$, $CH_2F$, $CHF_2$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, $C_{3-6}$ cycloalkyl substituted with 0–1 $R^{c1}$, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

$R^d$ is, independently at each occurrence, $C_{1-6}$ alkyl, $OR^a$, Cl, F, Br, =O, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, $CF_3$, or phenyl;

$R^5$ is, independently at each occurrence, $C_{1-4}$ alkyl substituted with 0–2 $R^b$, or $C_{1-4}$ alkyl substituted with 0–2 $R^e$;

r, at each occurrence, is selected from 0, 1, 2, and 3; and s, at each occurrence, is selected from 0, 1, 2, and 3.

4. A compound according to claim 3, wherein:

A is —C(O)NHOH;

Z is phenyl substituted with 1–2 $R^b$, naphthyl substituted with 1–2 $R^b$, or pyridyl substituted with 1–2 $R^b$;

$Z^a$ is phenyl substituted with 1–3 $R^c$, naphthyl substituted with 1–3 $R^c$, or a heterocycle substituted with 1–3 $R^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, and pyrazolo[1,5-a]pyridinyl;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is selected from Q, $C_{1-6}$ alkylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, or —$(CR^aR^{a1})_rNR^aC(O)O(CR^aR^{a1})_s$-Q;

Q is, independently at each occurrence, H, a $C_{3-6}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

$R^2$ is $Q^1$ or $C_{1-6}$ alkylene-$Q^1$;

$Q^1$ is, independently at each occurrence, H, phenyl substituted with 0–2 $R^d$, or a 5–6 membered heterocycle consisting of carbon atoms and 1–4 heteroatoms selected from N, O, and $S(O)_p$, and substituted with 0–2 $R^d$;

$R^3$ is Q, $C_{1-4}$ alkylene-Q, $C_{2-4}$ alkenylene-Q, $C_{2-4}$ alkynylene-Q, —$(CR^aR^{a1})_rNR^a(CR^aR^{a1})_s$-Q, —$(CR^aR^{a1})_rNR^aC(O)(CR^aR^{a1})_s$-Q, —$(CR^aR^{a1})_rNR^aC(O)O(CR^aR^{a1})_s$-Q, —$(CR^aR^{a1})_rNR^aC(O)NR^a(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q;

$R^4$ is $Q^1$ or $C_{1-6}$ alkylene-$Q^1$;

$R^{4a}$ is Q, —$CH_2$-Q, —$CH_2O(CH_2)_s$-Q, —$CH_2NR^a(CH_2)_s$-Q, —$CH_2C(O)(CH_2)_s$-Q, —$CH_2C(O)O(CH_2)_s$-Q, —$CH_2C(O)NR^aR^{a1}$, —$(CH_2)_rC(O)NR^aOR^a$, —$CH_2C(O)NR^a(CH_2)_s$-Q, —$CH_2NR^aC(O)(CH_2)_s$-Q, or —$CH_2NR^aC(O)O(CH_2)_s$-Q;

$R^{a1}$ is, independently at each occurrence, H, $C_{1-6}$ alkyl, phenyl, or benzyl;

$R^{a3}$ is, independently at each occurrence, H, $C_{1-6}$ alkyl, phenyl, or benzyl;

$R^c$ is, independently at each occurrence, H, $OR^a$, Cl, F, Br, =O, $CF_3$, $CH_2F$, $CHF_2$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$; and alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of: carbon atoms and 0–2 heteroatoms selected from N, O, and $S(O)_p$.

5. A compound according to claim 4, wherein:

U is absent or is O, $NR^{a1}$, C(O), $CR^a(OH)$, $C(O)NR^{a1}$, or $NR^{a1}C(O)$;

X is absent or is methylene or butynylene;

Y is absent or is 0;

Z is phenyl substituted with 1–2 $R^b$;

$Z^a$ is naphthyl substituted with 1–3 $R^c$, or a heterocycle substituted with 1–3 $R^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, pyranyl, pyrazinyl, pyrazolyl, pyridoimidazolyl, pyrrolidinyl, pyrrolyl, quinolinyl, tetrahydroquinolinyl, isoquinolinyl, tetrahydro-isoquinolinyl, imidazolyl, benzimidazolyl, benzothiazinyl, benzofuranyl, benzothiophenyl, benzoxazolyl, benzthiazolyl, benztriazolyl, benzisoxazolyl, benzisothiazolyl, indolyl, indolinyl, indazolyl, isobenzofuranyl, isoindazolyl, isoindolinyl, isoindolyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, and pyrazolo[1,5-a]pyridinyl;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, —$(CR^aR^{a1})_rNR^a(CR^aR^{a1})_s$-Q, or —$(CR^aR^{a1})_rNR^aC(O)O(CR^aR^{a1})_s$-Q;

Q is, independently at each occurrence, H, a $C_{3-6}$ carbocycle substituted with 0–3 $R^d$, or a 5–6 membered heterocycle consisting of carbon atoms and 1–4 heteroatoms selected from N, O, and $S(O)_p$, and substituted with 0–3 $R^d$;

$R^2$ is H or $C_{1-6}$ alkylene-$Q^1$, $R^3$ is Q, $C_{1-4}$ alkylene-Q, $C_{2-4}$ alkenylene-Q, $C_{2-4}$ alkynylene-Q, $-(CH_2)_rNR^a(CH_2)_s$-Q, $-(CH_2)_rNR^aC(O)(CH_2)_s$-Q, $-(CH_2)_rNR^aC(O)O(CR^aR^{a1})_s$-Q, $-(CH_2)_rNR^aC(O)NR^a(CH_2)_s$-Q, $-(CH_2)_rS(O)_p(CH_2)_s$-Q, or $-(CH_2)_rNR^aSO_2(CH_2)_s$-Q;

$R^4$ is H or $C_{1-6}$ alkylene-$Q^1$, $R^{4a}$ is Q, $-CH_2$-Q, $-CH_2O$-Q, $-CH_2NR^a$-Q, $-CH_2C(O)_s$-Q, $-CH_2C(O)O$-Q, $-CH_2C(O)NR^aR^{a1}$, $-C(O)NR^aOR^a$, $-CH_2C(O)NR^a$-Q, or $-CH_2NR^aC(O)O$-Q;

$R^a$ is, independently at each occurrence, H, or $C_{1-4}$ alkyl;

$R^{a1}$ is, independently at each occurrence, H, or $C_{1-4}$ alkyl;

$R^{a3}$ is, independently at each occurrence, H, $C_{1-4}$ alkyl, phenyl, or benzyl;

$R^c$ is, independently at each occurrence, $C_{1-6}$ alkyl, $C_{2-6}$ alkenyl, $C_{2-6}$ alkynyl, $OR^a$, Cl, F, Br, =O, $CF_3$, $CH_2F$, $CHF_2$, $-NR^aR^{a1}$, $-(CR^aR^{a1})_rC(O)R^{a1}$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, or phenyl; and alternatively, when two $R^c$ groups are attached to adjacent carbon atoms, together with the carbon atoms to which they are attached they form a 5–6 membered carbocyclic or heterocyclic ring D substituted with 0–1 $R^{c1}$ and consisting of: carbon atoms and 0–2 heteroatoms selected from N, O, and $S(O)_p$.

6. A compound according to claim 5, wherein:

U is absent or is O, $NR^{a1}$, C(O), or $CR^a(OH)$;

Y is absent;

$R^1$ is H, $C_{1-4}$ alkylene-Q, $-(CH_2)_rNR^a(CH_2)_s$-Q, or $-(CH_2)_rNR^aC(O)O(CR^aR^{a1})_s$-Q;

$R^2$ is H, $CH_3$, $CH_2CH_3$, $CH_2CH_2CH_3$, or $CH(CH_3)_2$;

$R^3$ is Q, $C_{1-4}$ alkylene-Q, $-(CH_2)_rNR^a(CH_2)_s$-Q, $-(CH_2)_rNR^aC(O)(CH_2)_s$-Q, $-(CH_2)_rNR^aC(O)O(CR^aR^{a1})_s$-Q, $-(CH_2)_rNR^aC(O)NR^a(CH_2)_s$-Q, $-(CH_2)_rS(CH_2)_s$-Q, or $-(CH_2)_rNR^aSO_2(CH_2)_s$-Q;

$R^4$ is H, $CH_3$, $CH_2CH_3$, $CH_2CH_2CH_3$, or $CH(CH_3)_2$;

$R^{4a}$ is Q, $-CH_2$-Q, $-CH_2O$-Q, $-CH_2NR^a$-Q, $-CH_2C(O)_s$-Q, $-CH_2C(O)O$-Q, $-CH_2C(O)NR^aR^{a1}$, $-C(O)NR^aOR^a$, or $-CH_2C(O)NR^a$-Q;

r, at each occurrence, is selected from 0, 1, and 2; and s, at each occurrence, is selected from 0, 1, and 2.

7. A compound according to claim 6, wherein:

U is O, $NR^{a1}$, or $CR^a(OH)$;

$Z^a$ is naphthyl substituted with 1–3 $R^c$, or a heterocycle substituted with 1–3 $R^c$ and selected from pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, pyrazolyl, and pyrazolo[1,5-a]pyridinyl;

$R^1$ is H, $CH_3$, $CH_2CH_3$, $CH_2CH_2CH_3$, $CH(CH_3)_2$, $NH_2$, or $-NHC(O)OC(CH_3)_3$;

$R^2$ is H or $CH_3$;

$R^3$ is Q, $C_{1-4}$ alkylene-Q, $-NR^a(CH_2)_s$-Q, $-NR^aC(O)(CH_2)_s$-Q, $-NR^aC(O)O(CR^aR^{a1})_s$-Q, $-NR^aC(O)NR^a(CH_2)_s$-Q, $-S(CH_2)_s$-Q, or $-NR^aSO_2(CH_2)_s$-Q;

$R^{4a}$ is Q, $-CH_2$-Q, $-CH_2O$-Q, $-CH_2NR^a$-Q, or $-C(O)NR^aOR^a$;

Q is, independently at each occurrence, H, phenyl substituted with 0–3 $R^d$, or a 5–6 membered heterocycle consisting of carbon atoms and 1–2 heteroatoms selected from N, O, and $S(O)_p$, and substituted with 0–3 $R^d$;

$R^b$ is, independently at each occurrence, H, $C_{1-6}$ alkyl, $OR^a$, Cl, F, Br, $-NR^aR^{a1}$, $-C(O)R^a$, $-C(O)OR^a$, $-C(O)NR^aR^{a1}$, $-S(O)_2NR^aR^{a1}$, $-NR^aS(O)_2R^{a3}$, $-S(O)_pR^{a3}$, or $CF_3$;

$R^c$ is, independently at each occurrence, $C_{1-6}$ alkyl, $C_{2-6}$ alkenyl, $C_{2-6}$ alkynyl, $OR^a$, Cl, F, Br, =O, $CF_3$, $-NR^aR^{a1}$, $-(CR^aR^{a1})_rC(O)R^{a1}$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, or $-(CR^aR^{a1})_rNR^aSO_2R^{a3}$; and alternatively, when two $R^c$ groups are attached to adjacent carbon atoms, together with the carbon atoms to which they are attached they form a 5–6 membered saturated ring consisting of: carbon atoms and 0–1 heteroatoms selected from N, O, and $S(O)_p$.

8. A compound according to claim 1, wherein the compound is selected from the group:

N-hydroxy-2-{3-[4-(2-methyl-quinolin-4-ylmethoxy)-phenyl]-4,5-dihydro-isoxazol-5-yl}-acetamide;

N-hydroxy-2-{3-[4-(2-methyl-quinolin-4-ylmethoxy)-phenyl]-4,5-dihydro-isoxazol-5-yl}-propionamide;

N-hydroxy-2-{3-[4-(2-methyl-quinolin-4-ylmethoxy)-phenyl]-5-morpholin-4-ylmethyl-4,5-dihydro-isoxazol-5-yl}-acetamide;

N-hydroxy-2-{3-[4-(2-methyl-quinolin-4-ylmethoxy)-phenyl]-5-piperazin-1-ylmethyl-4,5-dihydro-isoxazol-5-yl}-acetamide;

2-{5-dimethylaminomethyl-3-[4-(2-methyl-quinolin-4-ylmethoxy)-phenyl]-4,5-dihydro-isoxazol-5-yl}-N-hydroxy-acetamide;

N-hydroxy-3-{3-[4-(2-methyl-quinolin-4-ylmethoxy)-phenyl]-4,5-dihydro-isoxazol-5-yl}-propionamide;

N-hydroxy-3-methyl-3-{3-[4-(2-methyl-quinolin-4-ylmethoxy)-phenyl]-4,5-dihydro-isoxazol-5-yl}-butyramide;

(1-hydroxycarbamoyl-2-{3-[4-(2-methyl-quinolin-4-ylmethoxy)-phenyl]-4,5-dihydro-isoxazol-5-yl}-ethyl)-carbamic acid tert-butyl ester;

2-amino-N-hydroxy-3-{3-[4-(2-methyl-quinolin-4-ylmethoxy)-phenyl]-4,5-dihydro-isoxazol-5-yl}-propionamide;

3-amino-N-hydroxy-3-{3-[4-(2-methyl-quinolin-4-ylmethoxy)-phenyl]-4,5-dihydro-isoxazol-5-yl}-propionamide;

N-hydroxy-3-{3-[4-(2-methyl-quinolin-4-ylmethoxy)-phenyl]-4,5-dihydro-isoxazol-5-yl}-3-methylsulfanyl-propionamide;

N-hydroxy-3-{3-[4-(2-methyl-quinolin-4-ylmethoxy)-phenyl]-4,5-dihydro-isoxazol-5-yl}-3-morpholin-4-yl-propionamide;

3-amino-N-hydroxy-3-{3-[4-(2-methyl-quinolin-4-ylmethoxy)-phenyl]-4,5-dihydro-isoxazol-5-yl}-butyramide;

furan-2-carboxylic acid (2-hydroxycarbamoyl-1-{3-[4-(2-methyl-quinolin-4-ylmethoxy)-phenyl]-4,5-dihydro-isoxazol-5-yl}-ethyl)-amide;

N-hydroxy-3-{3-[4-(2-methyl-quinolin-4-ylmethoxy)-phenyl]-4,5-dihydro-isoxazol-5-yl}-3-pyrrolidin-1-yl-propionamide;

3-acetylamino-N-hydroxy-3-{3-[4-(2-methyl-quinolin-4-ylmethoxy)-phenyl]-4,5-dihydro-isoxazol-5-yl}-propionamide;

3-dimethylamino-N-hydroxy-3-{3-[4-(2-methyl-quinolin-4-ylmethoxy)-phenyl]-4,5-dihydro-isoxazol-5-yl}-propionamide;

3-(3-ethyl-ureido)-N-hydroxy-3-{3-[4-(2-methyl-quinolin-4-ylmethoxy)-phenyl]-4,5-dihydro-isoxazol-5-yl}-propionamide;

N-hydroxy-3-methanesulfonylamino-3-{3-[4-(2-methyl-quinolin-4-ylmethoxy)-phenyl]-4,5-dihydro-isoxazol-5-yl}-propionamide;

3-[(furan-2-ylmethyl)-amino]-N-hydroxy-3-{3-[4-(2-methyl-quinolin-4-ylmethoxy)-phenyl]-4,5-dihydro-isoxazol-5-yl}-propionamide;

3-benzylamino-N-hydroxy-3-{3-[4-(2-methyl-quinolin-4-ylmethoxy)-phenyl]-4,5-dihydro-isoxazol-5-yl}-propionamide;

(2-hydroxycarbamoyl-1-{3-[4-(2-methyl-quinolin-4-ylmethoxy)-phenyl]-4,5-dihydro-isoxazol-5-yl}-ethyl)-carbamic acid isobutyl ester;

N-hydroxy-3-{5-methyl-3-[4-(2-methyl-quinolin-4-ylmethoxy)-phenyl]-4,5-dihydro-isoxazol-5-yl}-propionamide;

N-hydroxy-3-{5-hydroxymethyl-3-[4-(2-methyl-quinolin-4-ylmethoxy)-phenyl]-4,5-dihydro-isoxazol-5-yl}-propionamide;

5-(2-hydroxycarbamoyl-ethyl)-3-[4-(2-methyl-quinolin-4-ylmethoxy)-phenyl]-4,5-dihydro-isoxazole-5-carboxylic acid methyl ester;

5-(2-hydroxycarbamoyl-ethyl)-3-[4-(2-methyl-quinolin-4-ylmethoxy)-phenyl]-4,5-dihydro-isoxazole-5-carboxylic acid hydroxyamide;

2-{3-[4-(2-methyl-quinolin-4-ylmethoxy)-phenyl]-4,5-dihydro-isoxazol-5-yl}-cyclopent-1-enecarboxylic acid hydroxyamide;

cis-2-{3-[4-(2-methyl-quinolin-4-ylmethoxy)-phenyl]-4,5-dihydro-isoxazol-5-yl}-cyclopentanecarboxylic acid hydroxyamide;

cis-4-{3-[4-(2-methyl-quinolin-4-ylmethoxy)-phenyl]-4,5-dihydro-isoxazol-5-yl}-pyrrolidine-3-carboxylic acid hydroxyamide;

cis-4-{3-[4-(2-methyl-quinolin-4-ylmethoxy)-phenyl]-4,5-dihydro-isoxazol-5-yl}-tetrahydro-furan-3-carboxylic acid hydroxyamide;

N-hydroxy-2-{3-[4-(2-methyl-quinolin-4-ylmethoxy)-phenyl]-1-oxa-2-aza-spiro[4.5]dec-2-en-6-yl}-acetamide;

N-hydroxy-2-{3-[4-(2-methyl-quinolin-4-ylmethoxy)-phenyl]-1,8-dioxa-2-aza-spiro[4.5]dec-2-en-6-yl}-acetamide;

6-hydroxycarbamoylmethyl-3-[4-(2-methyl-quinolin-4-ylmethoxy)-phenyl]-1-oxa-2,8-diaza-spiro[4.5]dec-2-ene-8-carboxylic acid tert-butyl ester;

N-hydroxy-2-{3-[4-(2-methyl-quinolin-4-ylmethoxy)-phenyl]-1-oxa-2,8-diaza-spiro[4.5]dec-2-en-6-yl}-acetamide;

N-hydroxy-2-{8-methyl-3-[4-(2-methyl-quinolin-4-ylmethoxy)-phenyl]-1-oxa-2,8-diaza-spiro[4.5]dec-2-en-6-yl}-acetamide;

2-{8-acetyl-3-[4-(2-methyl-quinolin-4-ylmethoxy)-phenyl]-1-oxa-2,8-diaza-spiro[4.5]dec-2-en-6-yl}-N-hydroxy-acetamide;

7-methyl-3-[4-(2-methyl-quinolin-4-ylmethoxy)-phenyl]-6-oxo-1-oxa-2,7-diaza-spiro[4.4]non-2-ene-9-carboxylic acid hydroxyamide;

7-methyl-3-[4-(2-methyl-quinolin-4-ylmethoxy)-phenyl]-6-oxo-1-oxa-2,7-diaza-spiro[4.5]dec-2-ene-10-carboxylic acid hydroxyamide;

N-hydroxy-2-(4-{3-[4-(2-methyl-quinolin-4-ylmethoxy)-phenyl]-4,5-dihydro-isoxazol-5-yl}-tetrahydro-pyran-4-yl)-acetamide;

2-(1-acetyl-4-{3-[4-(2-methyl-quinolin-4-ylmethoxy)-phenyl]-4,5-dihydro-isoxazol-5-yl}-piperidin-4-yl)-N-hydroxy-acetamide;

3-hydroxycarbamoylmethyl-3-{3-[4-(2-methyl-quinolin-4-ylmethoxy)-phenyl]-4,5-dihydro-isoxazol-5-yl}-pyrrolidine-1-carboxylic acid tert-butyl ester;

N-hydroxy-2-(3-{3-[4-(2-methyl-quinolin-4-ylmethoxy)-phenyl]-4,5-dihydro-isoxazol-5-yl}-pyrrolidin-3-yl)-acetamide; and N-hydroxy-2-(1-methyl-3-{3-[4-(2-methyl-quinolin-4-ylmethoxy)-phenyl]-4,5-dihydro-isoxazol-5-yl}-pyrrolidin-3-yl)-acetamide;

or a stereoisomer or pharmaceutically acceptable salt form thereof.

9. A pharmaceutical composition, comprising: a pharmaceutically acceptable carrier and a therapeutically effective amount of a compound according to claim 1 or a pharmaceutically acceptable salt form thereof.

10. A method for treating an inflammatory disorder, comprising: administering to a patient in need thereof a therapeutically effective amount of a compound according to claim 1 or a pharmaceutically acceptable salt form thereof.

11. A method of treating according to claim 10, wherein the inflammatory disorder is selected from allergy, allergic asthma, asthma, atopic dermatitis, autoimmune hepatitis, Bechet's disease, cachexia, chronic obstruction pulmonary disease, Crohn's disease, gingivitis, gout, infectious arthritis, multiple sclerosis, osteoarthritis, periodontitis, psoriasis, psoriatic arthritis, rheumatic fever, rheumatoid arthritis, and skin inflammatory diseases.

12. A compound according to claim 2, wherein:

A is —C(O)NHOH or —N(OH)CHO;

U is absent or is O, $NR^{a1}$, C(O), $CR^a(OH)$, $C(O)NR^{a1}$, $NR^{a1}C(O)$, $S(O)_p$, $S(O)_pNR^{a1}$, or $NR^{a1}S(O)_p$;

X is absent or is methylene, ethylene, propynylene, or butynylene;

Z is a $C_{5-10}$ carbocycle substituted with 1–2 $R^b$, or a 5–10 membered heterocycle consisting of carbon atoms and 1–4 heteroatoms selected from N, O, and $S(O)_p$, and substituted with 1–2 $R^b$;

$Z^a$ is H, $C_{5-10}$ carbocycle substituted with 1–3 $R^c$, or a 5–10 membered heterocycle consisting of carbon atoms and 1–4 heteroatoms selected from N, O, and $S(O)_p$, and substituted with 1–3 $R^c$;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, $C_{2-6}$ alkenylene-Q, $C_{2-6}$ alkynylene-Q, $—(CR^aR^{a1})_rO(CR^aR^{a1})_s$-Q, $—(CR^aR^{a1})_rNR^a(CR^aR^{a1})_s$-Q, $—(CR^aR^{a1})_rC(O)(CR^aR^{a1})_s$-Q, $—(CR^aR^{a1})_rC(O)O(CR^aR^{a1})_s$-Q, $—(CR^aR^{a1})_rC(O)NR^aR^{a1}$, $—(CR^aR^{a1})_rC(O)NR^a(CR^aR^{a1})_s$-Q, $—(CR^aR^{a1})_rNR^aC(O)(CR^aR^{a1})_s$-Q, $—(CR^aR^{a1})_rOC(O)NR^a(CR^aR^{a1})_s$-Q, $—(CR^aR^{a1})_rNR^aC(O)O(CR^aR^{a1})_s$-Q, $—(CR^aR^{a1})_rS(O)_p(CR^aR^{a1})_s$-Q, $—(CR^aR^{a1})_rSO_2NR^a(CR^aR^{a1})_s$-Q, or $—(CR^aR^{a1})_rNR^aSO_2(CR^aR^{a1})_s$-Q;

Q is, independently at each occurrence, H, a $C_{3-8}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

R² is Q¹, C$_{1-6}$ alkylene-Q¹, C$_{2-6}$ alkenylene-Q¹, —(CR$^a$R$^{a1}$)$_r$O(CR$^a$R$^{a1}$)$_s$-Q¹, —(CR$^a$R$^{a1}$)$_r$NR$^a$(CR$^a$R$^{a1}$)$_s$-Q¹, or —(CR$^a$R$^{a1}$)$_r$C(O)(CR$^a$R$^{a1}$)$_s$-Q¹;

Q¹ is, independently at each occurrence, H, a C$_{5-10}$ carbocycle substituted with 0–2 R$^d$, or a 5–10 membered heterocycle consisting of carbon atoms and 1–4 heteroatoms selected from N, O, and S(O)$_p$, and substituted with 0–2 R$^d$;

R³ is Q, C$_{1-6}$ alkylene-Q, C$_{2-6}$ alkenylene-Q, C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$NR$^a$C(O)O(CR$^a$R$^{a1}$)$_s$-Q, —(CR$^a$R$^{a1}$)$_r$NR$^a$C(O)NR$^a$(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_r$NR$^a$SO$_2$(CR$^a$R$^{a1}$)$_s$-Q;

alternatively, R¹ and R³ combine, along with the carbon atom to which they are attached, to form a 5–6 membered carbocyclic or heterocyclic ring consisting of: carbon atoms and 0–2 heteroatoms selected from the group consisting of N, O, and S(O)$_p$ and substituted with 0–2 R$^d$;

alternatively, when R¹ and R³ combine to form a carbocyclic or heterocyclic ring, the R² and R⁴ combine to form a double bond;

R⁴ is Q¹, C$_{1-6}$ alkylene-Q¹, C$_{2-6}$ alkenylene-Q¹, —(CR$^a$R$^{a1}$)$_r$O(CR$^a$R$^{a1}$)$_s$-Q¹, —(CR$^a$R$^{a1}$)$_r$NR$^a$(CR$^a$R$^{a1}$)$_s$-Q¹, or —(CR$^a$R$^{a1}$)$_r$C(O)(CR$^a$R$^{a1}$)$_s$-Q¹, alternatively, R³ and R⁴ combine, along with the carbon atom to which they are attached, to form a 5–6 membered carbocyclic or heterocyclic ring consisting of: carbon atoms and 0–2 heteroatoms selected from the group consisting of N, O, and S(O)$_p$ and substituted with 0–2 R$^d$;

R$^{4a}$ is Q, C$_{1-4}$ alkylene-Q, —(CH$_2$)$_r$O(CH$_2$)$_s$-Q, —(CH$_2$)$_r$NR$^a$(CH$_2$)$_s$-Q, —(CH$_2$)$_r$C(O)(CH$_2$)$_s$-Q, —(CH$_2$)$_r$C(O)(CH$_2$)$_s$-Q, —(CH$_2$)$_r$C(O)NR$^a$R$^{a1}$, —(CH$_2$)$_r$C(O)NR$^a$OR$^a$, —(CH$_2$)$_r$C(O)NR$^a$(CH$_2$)$_s$-Q, —(CH$_2$)$_r$NR$^a$C(O)(CH$_2$)$_s$-Q, or —(CH$_2$)$_r$NR$^a$C(O)O(CH$_2$)$_s$-Q;

alternatively, R¹ and R$^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and S(O)$_p$ and substituted with 0–3 R$^d$, provided that n is 0;

alternatively, R³ and R$^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and S(O)$_p$ and substituted with 0–2 R$^d$;

R$^{a3}$ is, independently at each occurrence, H, C$_{1-6}$ alkyl, C$_{2-6}$ alkenyl, or —(CH$_2$)$_r$-3–8 membered carbocyclic or heterocyclic ring consisting of carbon atoms and 0–2 ring heteroatoms selected from N, NR$^{a2}$, O, and S(O)$_p$, and substituted with 0–3 R$^{c1}$;

R$^c$ is, independently at each occurrence, H, OR$^a$, Cl, F, Br, =O, CF$_3$, CH$_2$F, CHF$_2$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, C$_{3-6}$ cycloalkyl substituted with 0–1 R$^{c1}$, phenyl substituted with 0–2 R$^{c1}$, or 5–6 membered heterocycle consisting of carbon atoms and 1–4 heteroatoms selected from N, O, and S(O)$_p$, and substituted with 0–2 R$^{c1}$;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of: carbon atoms and 0–2 heteroatoms selected from N, O, and S(O)$_p$;

R$^d$ is, independently at each occurrence, C$_{1-6}$ alkyl, OR$^a$, Cl, F, Br, =O, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, CF$_3$, or phenyl;

R⁵ is, independently at each occurrence, C$_{1-4}$ alkyl substituted with 0–2 R$^b$, or C$_{1-4}$ alkyl substituted with 0–2 R$^e$;

r, at each occurrence, is selected from 0, 1, 2, and 3; and s, at each occurrence, is selected from 0, 1, 2, and 3.

13. A compound according to claim 12, wherein:

A is —C(O)NHOH;

Z is phenyl substituted with 1–2 R$^b$, naphthyl substituted with 1–2 R$^b$, or pyridyl substituted with 1–2 R$^b$;

Z$^a$ is phenyl substituted with 1–3 R$^c$, naphthyl substituted with 1–3 R$^c$, or a heterocycle substituted with 1–3 R$^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, and pyrazolo[1,5-a]pyridinyl;

provided that U, Y, Z, and Z$^a$ do not combine to form a N—N, N—O, O—N, O—O, S(O)$_p$—O, O—S(O)$_p$, or S(O)$_p$—S(O)$_p$ group;

R¹ is selected from Q, C$_{1-6}$ alkylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, or —(CR$^a$R$^{a1}$)$_r$NR$^a$C(O)O(CR$^a$R$^{a1}$)$_s$-Q;

Q is, independently at each occurrence, H, a C$_{3-6}$ carbocycle substituted with 0–3 R$^d$, or a 5–10 membered heterocycle consisting of carbon atoms and 1–4 heteroatoms selected from N, O, and S(O)$_p$, and substituted with 0–3 R$^d$;

R² is Q¹ or C$_{1-6}$ alkylene-Q¹;

Q¹ is, independently at each occurrence, H, phenyl substituted with 0–2 R$^d$, or a 5–6 membered heterocycle consisting of carbon atoms and 1–4 heteroatoms selected from N, O, and S(O)$_p$, and substituted with 0–2 R$^d$;

R³ is Q, C$_{1-4}$ alkylene-Q, C$_{2-4}$ alkenylene-Q, C$_{2-4}$ alkynylene-Q, —(CR$^a$R$^{a1}$)$_r$NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$NR$^a$C(O)O(CR$^a$R$^{a1}$)$_s$-Q, —(CR$^a$R$^{a1}$)$_r$NR$^a$C(O)NR$^a$(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_r$NR$^a$SO$_2$(CR$^a$R$^{a1}$)$_s$-Q;

alternatively, R¹ and R³ combine, along with the carbon atom to which they are attached, to form a 5–6 membered carbocyclic or heterocyclic ring consisting of:

carbon atoms and 0–2 heteroatoms selected from the group consisting of N, O, and $S(O)_p$ and substituted with 0–2 $R^d$;

alternatively, when $R^1$ and $R^3$ combine to form a carbocyclic or heterocyclic ring, the $R^2$ and $R^4$ combine to form a double bond;

$R^4$ is $Q^1$ or $C_{1-6}$ alkylene-$Q^1$;

alternatively, $R^3$ and $R^4$ combine, along with the carbon atom to which they are attached, to form a 5–6 membered carbocyclic or heterocyclic ring consisting of: carbon atoms and 0–2 heteroatoms selected from the group consisting of N, O, and $S(O)_p$ and substituted with 0–2 $R^d$;

$R^{4a}$ is Q, —$CH_2$-Q, —$CH_2O(CH_2)_s$-Q, —$CH_2NR^a(CH_2)_s$-Q, —$CH_2C(O)(CH_2)_s$-Q, —$CH_2C(O)O(CH_2)_s$-Q, —$CH_2C(O)NR^aR^{a1}$, —$(CH_2)_rC(O)NR^aOR^a$, —$CH_2C(O)NR^a(CH_2)_s$-Q, —$CH_2NR^aC(O)(CH_2)_s$-Q, or —$CH_2NR^aC(O)O(CH_2)_s$-Q;

alternatively, $R^1$ and $R^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and $S(O)_p$ and substituted with 0–3 $R^d$, provided that n is 0;

alternatively, $R^3$ and $R^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and $S(O)_p$ and substituted with 0–2 $R^d$;

$R^{a1}$ is, independently at each occurrence, H, $C_{1-6}$ alkyl, phenyl, or benzyl;

$R^{a3}$ is, independently at each occurrence, H, $C_{1-6}$ alkyl, phenyl, or benzyl;

$R^c$ is, independently at each occurrence, H, $OR^a$, Cl, F, Br, =O, $CF_3$, $CH_2F$, $CHF_2$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$; and alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of: carbon atoms and 0–2 heteroatoms selected from N, O, and $S(O)_p$.

14. A compound according to claim 13, wherein:

U is absent or is O, $NR^{a1}$, C(O), $CR^a(OH)$, $C(O)NR^{a1}$, or $NR^{a1}C(O)$;

X is absent or is methylene or butynylene;

Y is absent or is O;

Z is phenyl substituted with 1–2 $R^b$;

$Z^a$ is naphthyl substituted with 1–3 $R^c$, or a heterocycle substituted with 1–3 $R^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, pyranyl, pyrazinyl, pyrazolyl, pyridoimidazolyl, pyrrolidinyl, pyrrolyl, quinolinyl, tetrahydroquinolinyl, isoquinolinyl, tetrahydro-isoquinolinyl, imidazolyl, benzimidazolyl, benzothiazinyl, benzofuranyl, benzothiophenyl, benzoxazolyl, benzthiazolyl, benztriazolyl, benzisoxazolyl, benzisothiazolyl, indolyl, indolinyl, indazolyl, isobenzofuranyl, isoindazolyl, isoindolinyl, isoindolyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, and pyrazolo[1,5-a]pyridinyl;

provided that U, Y, Z, and $Z^a$ do not combine to form a N—N, N—O, O—N, O—O, $S(O)_p$—O, O—$S(O)_p$, or $S(O)_p$—$S(O)_p$ group;

$R^1$ is Q, $C_{1-6}$ alkylene-Q, —$(CR^aR^{a1})_rNR^a(CR^aR^{a1})_s$-Q, or —$(CR^aR^{a1})_rNR^aC(O)O(CR^aR^{a1})_s$-Q;

Q is, independently at each occurrence, H, a $C_{3-6}$ carbocycle substituted with 0–3 $R^d$, or a 5–6 membered heterocycle consisting of carbon atoms and 1–4 heteroatoms selected from N, O, and $S(O)_p$, and substituted with 0–3 $R^d$;

$R^2$ is H or $C_{1-6}$ alkylene-$Q^1$, $R^3$ is Q, $C_{1-4}$ alkylene-Q, $C_{2-4}$ alkenylene-Q, $C_{2-4}$ alkynylene-Q, —$(CH_2)_rNR^a(CH_2)_s$-Q, —$(CH_2)_rNR^aC(O)(CH_2)_s$-Q, —$(CH_2)_rNR^aC(O)O(CR^aR^{a1})_s$-Q, —$(CH_2)_rNR^aC(O)NR^a(CH_2)_s$-Q, —$(CH_2)_rS(O)_p(CH_2)_s$-Q, or —$(CH_2)_rNR^aSO_2(CH_2)_s$-Q;

$R^4$ is H or $C_{1-6}$ alkylene-$Q^1$, alternatively, $R^3$ and $R^4$ combine, along with the carbon atom to which they are attached, to form a 5–6 membered carbocyclic or heterocyclic ring consisting of: carbon atoms and 0–2 heteroatoms selected from the group consisting of N, O, and $S(O)_p$ and substituted with 0–2 $R^d$;

$R^{4a}$ is Q, —$CH_2$-Q, —$CH_2O$-Q, —$CH_2NR^a$-Q, —$CH_2C(O)_s$-Q, —$CH_2C(O)O$-Q, —$CH_2C(O)NR^aR^{a1}$, —$C(O)NR^aOR^a$, —$CH_2C(O)NR^a$-Q, or —$CH_2NR^aC(O)O$-Q;

alternatively, $R^1$ and $R^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and $S(O)_p$ and substituted with 0–3 $R^d$, provided that n is 0;

alternatively, $R^3$ and $R^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and $S(O)_p$ and substituted with 0–2 $R^d$;

$R^a$ is, independently at each occurrence, H, or $C_{1-4}$ alkyl;

$R^{a1}$ is, independently at each occurrence, H, or $C_{1-4}$ alkyl;

$R^{a3}$ is, independently at each occurrence, H, $C_{1-4}$ alkyl, phenyl, or benzyl;

$R^c$ is, independently at each occurrence, $C_{1-6}$ alkyl, $C_{2-6}$ alkenyl, $C_{2-6}$ alkynyl, $OR^a$, Cl, F, Br, =O, $CF_3$, $CH_2F$, $CHF_2$, —$NR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, or phenyl; and alternatively, when two $R^c$ groups are attached to adjacent carbon atoms, together with the carbon atoms to which they are attached they form a 5–6 membered carbocyclic or heterocyclic ring D substituted with 0–1 $R^{c1}$ and consisting of: carbon atoms and 0–2 heteroatoms selected from N, O, and $S(O)_p$.

15. A compound according to claim 14, wherein:

U is absent or is O, $NR^{a1}$, C(O), or $CR^a(OH)$;

Y is absent;

$R^1$ is H, $C_{1-4}$ alkylene-Q, —$(CH_2)_rNR^a(CH_2)_s$-Q, or —$(CH_2)_rNR^aC(O)O(CR^aR^{a1})_s$-Q;

$R^2$ is H, $CH_3$, $CH_2CH_3$, $CH_2CH_2CH_3$, or $CH(CH_3)_2$;

$R^3$ is Q, $C_{1-4}$ alkylene-Q, —(CH$_2$)$_r$NR$^a$(CH$_2$)$_s$-Q, —(CH$_2$)$_r$NR$^a$C(O)(CH$_2$)$_s$-Q, —(CH$_2$)$_r$NR$^a$C(O)O (CR$^a$R$^{a1}$)$_s$-Q, —(CH$_2$)$_r$NR$^a$C(O)NR$^a$(CH$_2$)$_s$-Q, —(CH$_2$)$_r$S(CH$_2$)$_s$-Q, or —(CH$_2$)$_r$NR$^a$SO$_2$(CH$_2$)$_s$-Q;

$R^4$ is H, CH$_3$, CH$_2$CH$_3$, CH$_2$CH$_2$CH$_3$, or CH(CH$_3$)$_2$;

alternatively, $R^3$ and $R^4$ combine, along with the carbon atom to which they are attached, to form a 5–6 membered carbocyclic or heterocyclic ring consisting of: carbon atoms and 0–2 heteroatoms selected from the group consisting of N, O, and S(O)$_p$ and substituted with 0–2 R$^d$;

$R^{4a}$ is Q, —CH$_2$-Q, —CH$_2$O-Q, —CH$_2$NR$^a$-Q, —CH$_2$C(O)$_s$-Q, —CH$_2$C(O)O-Q, —CH$_2$C(O)NR$^a$R$^{a1}$, —C(O)NR$^a$OR$^a$, or —CH$_2$C(O)NR$^a$-Q;

alternatively, $R^1$ and $R^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and S(O)$_p$ and substituted with 0–3 R$^d$, provided that n is 0;

alternatively, $R^3$ and $R^{4a}$ in Formula I combine, along with the carbon atoms to which they are attached, to form a 5–6 membered carbocyclic or heterocyclic ring consisting of: carbon atoms and 0–2 heteroatoms selected from the group consisting of N, O, and S(O)$_p$ and substituted with 0–2 R$^d$;

r, at each occurrence, is selected from 0, 1, and 2; and s, at each occurrence, is selected from 0, 1, and 2.

16. A compound according to claim 15, wherein:

U is O, NR$^{a1}$, or CR$^a$(OH);

$Z^a$ is naphthyl substituted with 1–3 R$^c$, or a heterocycle substituted with 1–3 R$^c$ and selected from pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chomen-4-yl, 2H-chomen-4-yl, pyrazolyl, and pyrazolo[1,5-a]pyridinyl;

$R^b$ is, independently at each occurrence, H, C$_{1-6}$ alkyl, OR$^a$, Cl, F, Br, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, or CF$_3$;

$R^c$ is, independently at each occurrence, C$_{1-6}$ alkyl, C$_{2-6}$ alkenyl, C$_{2-6}$ alkynyl, OR$^a$, Cl, F, Br, =O, CF$_3$, —NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, or —(CR$^a$R$^{a1}$)$_r$NR$^a$SO$_2$R$^{a3}$; and alternatively, when two R$^c$ groups are attached to adjacent carbon atoms, together with the carbon atoms to which they are attached they form a 5–6 membered saturated ring consisting of: carbon atoms and 0–1 heteroatoms selected from N, O, and S(O)$_p$.

17. A pharmaceutical composition, comprising: a pharmaceutically acceptable carrier and a therapeutically effective amount of a compound according to claim 2 or a pharmaceutically acceptable salt form thereof.

18. A pharmaceutical composition, comprising: a pharmaceutically acceptable carrier and a therapeutically effective amount of a compound according to claim 3 or a pharmaceutically acceptable salt form thereof.

19. A pharmaceutical composition, comprising: a pharmaceutically acceptable carrier and a therapeutically effective amount of a compound according to claim 4 or a pharmaceutically acceptable salt form thereof.

20. A pharmaceutical composition, comprising: a pharmaceutically acceptable carrier and a therapeutically effective amount of a compound according to claim 5 or a pharmaceutically acceptable salt form thereof.

21. A pharmaceutical composition, comprising: a pharmaceutically acceptable carrier and a therapeutically effective amount of a compound according to claim 6 or a pharmaceutically acceptable salt form thereof.

22. A pharmaceutical composition, comprising: a pharmaceutically acceptable carrier and a therapeutically effective amount of a compound according to claim 7 or a pharmaceutically acceptable salt form thereof.

23. A pharmaceutical composition, comprising: a pharmaceutically acceptable carrier and a therapeutically effective amount of a compound according to claim 8 or a pharmaceutically acceptable salt form thereof.

24. A pharmaceutical composition, comprising: a pharmaceutically acceptable carrier and a therapeutically effective amount of a compound according to claim 12 or a pharmaceutically acceptable salt form thereof.

25. A pharmaceutical composition, comprising: a pharmaceutically acceptable carrier and a therapeutically effective amount of a compound according to claim 13 or a pharmaceutically acceptable salt form thereof.

26. A pharmaceutical composition, comprising: a pharmaceutically acceptable carrier and a therapeutically effective amount of a compound according to claim 14 or a pharmaceutically acceptable salt form thereof.

27. A pharmaceutical composition, comprising: a pharmaceutically acceptable carrier and a therapeutically effective amount of a compound according to claim 15 or a pharmaceutically acceptable salt form thereof.

28. A pharmaceutical composition, comprising: a pharmaceutically acceptable carrier and a therapeutically effective amount of a compound according to claim 16 or a pharmaceutically acceptable salt form thereof.

* * * * *